US009534042B2

(12) United States Patent
Kurosawa et al.

(10) Patent No.: US 9,534,042 B2
(45) Date of Patent: Jan. 3, 2017

(54) INFLUENZA VIRUS-NEUTRALIZING ANTIBODY AND SCREENING METHOD THEREFOR

(75) Inventors: Yoshikazu Kurosawa, Aichi (JP); Yoshitaka Iba, Aichi (JP); Nobuko Ohshima, Aichi (JP); Yoshinobu Okuno, Osaka (JP)

(73) Assignees: Fujita Health University, Aichi (JP); The Research Foundation for Microbial Diseases of Osaka University, Osaka (JP)

(*) Notice: Subject to any disclaimer, the term of this patent is extended or adjusted under 35 U.S.C. 154(b) by 120 days.

(21) Appl. No.: 13/198,147

(22) Filed: Aug. 4, 2011

(65) Prior Publication Data

US 2012/0058124 A1 Mar. 8, 2012

Related U.S. Application Data

(60) Provisional application No. 61/380,051, filed on Sep. 3, 2010, provisional application No. 61/452,785, filed on Mar. 15, 2011.

(51) Int. Cl.
| | |
|---|---|
| *C07K 16/28* | (2006.01) |
| *C07K 16/10* | (2006.01) |
| *A61K 39/395* | (2006.01) |
| *A61K 47/48* | (2006.01) |
| *C07K 16/30* | (2006.01) |
| *A61K 39/00* | (2006.01) |

(52) U.S. Cl.
CPC ..... *C07K 16/1018* (2013.01); *A61K 2039/505* (2013.01); *C07K 2317/21* (2013.01); *C07K 2317/33* (2013.01); *C07K 2317/34* (2013.01); *C07K 2317/52* (2013.01); *C07K 2317/55* (2013.01); *C07K 2317/76* (2013.01); *C07K 2319/00* (2013.01)

(58) Field of Classification Search
CPC .................... A61K 2039/505; A61K 39/3955; C07K 2317/92; C07K 2317/76
USPC ........................................................ 424/159
See application file for complete search history.

(56) References Cited

FOREIGN PATENT DOCUMENTS

| | | | |
|---|---|---|---|
| EP | 1264885 | A1 | 12/2002 |
| WO | 01/62907 | A1 | 8/2001 |
| WO | 2007/134327 | A2 | 11/2007 |
| WO | 2008/028946 | A2 | 3/2008 |
| WO | WO2008118487 | * | 10/2008 |
| WO | 2009/079259 | A2 | 6/2009 |
| WO | 2009/115972 | A1 | 9/2009 |
| WO | 2009-121004 | A2 | 10/2009 |
| WO | 2010/010466 | A2 | 1/2010 |
| WO | 2010/010467 | A2 | 1/2010 |
| WO | WO2010010467 | * | 1/2010 |

OTHER PUBLICATIONS

Yoshida et al., Cross-protective potential of a novel monoclonal antibody directed against antigenic site B of the hemagglutinin of influenza A viruses, 2009, PLOS Pathogens, 5(3):1-9.*
Casset et al. "A peptide mimetic of an anti-CD4 monoclonal antibody by rational design", 2003, Biochemical and Biophysical Research Communication, 307:198-205.*
MacCallum et al., "Antibody-antigen interactions: Contact analysis and binding site topography", 1996, JMB, 262, 732-745.*
Rudikoff et al, "Single amino acid substitution altering antigen-binding specificity", 1982, PNAS, 79:1979-1983.*
Paul, Fundamental Immunology, 3rd edition, 1993:292-295. PDF pp. 1-6.*
Okuno, Yoshinobu, "Analysis of the properties of a human monoclonal antibody generated using an influenza vaccine strain as an antigen," Health and Labour Sciences Research Grant Collaborative Research Report, pp. 8-20 (2007).
Ekiert, Damian C. et al., "Antibody Recognition of a Highly Conserved Influenza Virus Epitope," Science, vol. 324:246-251 (2009).
Kashyap, Arun K. et al., "Combinatorial antibody libraries from survivors of the Turkish H5N1 avian influenza outbreak reveal virus neutralization strategies," PNAS, vol. 105(16):5986-5991 (2008).
Okada, Jun et al., "Monoclonal antibodies in man that neutralized H3N2 influenza viruses were classified into three groups with distinct strain specificity: 1968-1973, 1977-1993 and 1997-2003," Virology, vol. 397:322-330 (2010).
Sui, Jianhua et al., "Structural and functional bases for broad-spectrum neutralization of avian and human influenza A viruses," Nature Structural & Molecular Biology, vol. 16(3):265-273 (2009).
Throsby, Mark et al., "Heterosubtypic Neutralizing Monoclonal Antibodies Cross-Protective against H5N1 and H1N1 Recovered from Human IgM+ Memory B Cells," PLOS One , vol. 3(12):e3942, 1-15 (2008).
Underwood, P.A., "Mapping of Antigenic Changes in the Haemagglutinin of Hong Kong Influenza (H3N2) Strains using a Large Panel of Monoclonal Antibodies," J. gen. Virol., vol. 62:153-169 (1982).
Wiley, D.C. et al., "Structural identification of the antibody-binding sites of Hong Kong influenza haemagglutinin and their involvement in antigenic variation," Nature, vol. 289:373-378 (1981).

Yamashita, Akifumi et al., "Highly conserved sequences for human neutralization epitope on hemagglutinin of influenza A viruses H3N2, H1N1 and H5N1: Implication for human monoclonal antibody recognition," Biochemical and Biophysical Research Communications, vol. 393:614-618 (2010).

Yoshida, Reiko et al., "Cross-Protective Potential of a Novel Monoclonal Antibody Directed against Antigenic Site B of the Hemagglutinin of Influenza A Viruses," PLOS Pathogens, vol. 5(3):e1000350, 1-9 (2009).

(Continued)

*Primary Examiner* — Janet L Andres
*Assistant Examiner* — Barry A Chestnut
(74) *Attorney, Agent, or Firm* — Nelson Mullins Riley & Scarborough LLP; Jane E. Remillard, Esq.; Jill Gorny Sloper, Esq.

(57) ABSTRACT

Provided is an anti-influenza virus antibody that exhibits neutralizing activity beyond the barrier of the two groups of influenza viruses categorized according to the conservativeness of hemagglutinin amino acids, a method of producing the same, and a test method for determining whether the subject carries the neutralizing antibody.

2 Claims, 28 Drawing Sheets
(17 of 28 Drawing Sheet(s) Filed in Color)

(56) References Cited

OTHER PUBLICATIONS

International Search Report for Application No. PCT/JP2011/070544, dated Dec. 13, 2011.
Corti, Davide et al., "A Neutralizing Antibody Selected from Plasma Cells That Binds to Group 1 and Group 2 Influenza A Hemagglutinins," Science, vol. 333:850-856 (2011).
Ekiert, Damian C. et al., "Broadly neutralizing antibodies against influenza virus and prospects for universal therapies," Current Opinion in Virology, vol. 2:134-141 (2012).
Han, Thomas et al., "Structural basis of influenza virus neutralization," Annals of the New York Academy of Sciences, vol. 1217:178-190 (2011).
Wang, Taia T. et al., "Universal epitopes of influenza virus hemagglutinins?" Nature Structure & Molecular Biology, vol. 16(3):233-234 (2009).
Supplementary European Search Report for Application No. 11822003, 2 pages, dated Jan. 22, 2014.
Chinese Office Action, Chinese Application No. 201180053180.4, dated Sep. 22, 2015, 8 pages.
Japanese Office Action, Japanese Patent Application No. 2012-531989, dated Sep. 15, 2015, 7 pages.
Japanese Office Action dated Feb. 2, 2016 issued in the corresponding Japanese Patent Application No. 2012-531989 with its English Language Excerption, 3 pages.

\* cited by examiner

FIG.1-1

| Group | Clone | Number of clones isolated | Isolated viral strains | A/Aichi/2 68 (H3N) | A/Fukuoka/ 1/70 (H3N2) | A/Tokyo/ 6/73 (H3N2) | A/Yamanashi/ 2/77 (H3N2) | A/Niigata/ 102/81 (H3N2) | A/Fukuoka/ C29/85 (H3N2) | A/Guizhou/ 54/89 (H3N2) | A/Kitakyusyu/ 159/93 (H3N2) | A/Sydney/ 5/97 (H3N2) | A/Panama/ 2007/99 (H3N2) | A/Wyoming/ 3/2003 (H3N2) | A/New York/ 55/2004 (H3N2) | A/New Caledonia/ 20/99 (H1N1) | WB |
|---|---|---|---|---|---|---|---|---|---|---|---|---|---|---|---|---|---|
| 1 | F045-153 | 1 | Tok93 | 1.372 | 1.345 | 3.025 | 0.535 | 0.474 | 0.264 | 0.481 | 0.113 | 0.127 | 0.157 | 0.272 | 0.228 | 0.204 | HA |
| 2 | F045-080 | 3 | Tok93 | 0.940 | 1.119 | 2.716 | 0.198 | 0.175 | 0.030 | 0.194 | 0.027 | 0.026 | 0.039 | 0.126 | 0.108 | 0.020 | HA |
| 3 | F045-194 | 1 | Tok93 | 1.108 | 1.126 | 1.057 | 0.837 | 0.393 | 0.213 | 0.532 | 0.105 | 0.218 | 0.266 | 0.444 | 0.236 | 0.076 | HA |
| 4 | F045-111 | 7 | Tok93 | 0.215 | 0.126 | 1.308 | 1.471 | 0.443 | -0.006 | 0.008 | 0.000 | 0.010 | 0.012 | 0.029 | 0.015 | 0.012 | HA |
|  | F045-158 | 1 | Tok93 | 0.773 | 1.139 | 2.452 | 1.734 | 0.319 | 0.190 | 0.256 | 0.088 | 0.086 | 0.124 | 0.181 | 0.174 | 0.559 |  |
| 5 | F045-059 | 4 | Tok93 | 0.111 | 0.318 | 2.575 | 0.140 | 0.131 | 0.028 | 0.131 | 0.024 | 0.025 | 0.034 | 0.097 | 0.062 | 0.027 | HA |
| 6 | F045-094 | 2 | Tok93 | 1.072 | 0.731 | 1.885 | 2.903 | 0.756 | 1.045 | 0.297 | 0.082 | 0.100 | 0.138 | 0.208 | 0.179 | 0.371 | HA |
| 7 | F045-171 | 3 | Tok93 | 0.719 | 0.907 | 2.308 | 1.911 | 0.568 | 0.413 | 0.319 | 0.082 | 0.089 | 0.113 | 0.207 | 0.146 | 0.151 |  |
| 8 | F045-087 | 2 | Tok93 | 0.201 | 0.413 | 1.463 | 2.205 | 1.024 | 1.810 | 0.265 | 0.065 | 0.072 | 0.091 | 0.121 | 0.139 | 0.142 | ? |
| 9 | F045-073 | 1 | Tok93 | 1.185 | 1.281 | 1.783 | 0.572 | 0.312 | 0.217 | 0.234 | 0.263 | 0.173 | 0.181 | 0.220 | 0.200 | 0.091 | HA |
|  | F045-079 | 1 | Tok93 | 1.005 | 0.656 | 2.661 | 0.512 | 0.441 | 0.211 | 0.349 | 0.083 | 0.125 | 0.095 | 0.194 | 0.140 | 0.172 |  |
| 10 | F045-046 | 26 | Aic68, Fuk70, Tok73 | 2.539 | 1.969 | 3.396 | 3.711 | 2.779 | 0.169 | 0.131 | 0.077 | 0.341 | 0.110 | 0.113 | 0.092 | 0.071 | HA |
|  | F044-056 | 7 | Fuk70, Tok73 | 1.108 | 1.475 | 1.059 | 1.648 | 1.081 | 0.113 | 0.123 | 0.145 | 0.322 | 0.153 | 0.101 | 0.088 | 0.080 |  |
|  | F045-066 | 1 | Tok93 | 1.417 | 1.067 | 1.720 | 2.121 | 1.265 | 0.069 | 0.070 | 0.050 | 0.643 | 0.048 | 0.050 | 0.060 | 0.051 |  |
|  | F045-067 | 1 | Tok93 | 1.999 | 1.026 | 1.874 | 2.334 | 1.084 | 0.093 | 0.064 | 0.050 | 1.270 | 0.052 | 0.051 | 0.080 | 0.052 |  |
|  | F045-076 | 1 | Tok93 | 1.545 | 1.089 | 2.554 | 2.906 | 1.011 | 0.113 | 0.096 | 0.054 | 2.102 | 0.082 | 0.090 | 0.107 | 0.048 |  |
| 11 | F022-360 | 14 | Aic68, Tok73, Kit93 | 2.999 | 2.513 | 2.783 | 2.489 | 2.386 | 0.513 | 0.492 | 2.065 | 3.269 | 1.667 | 0.111 | 0.080 | 0.491 | HA |
|  | F026-116 | 1 | kit93 | 1.057 | 0.637 | 1.002 | 1.756 | 1.120 | 0.270 | 0.287 | 1.597 | 0.555 | 1.092 | 0.131 | 0.129 | 0.246 |  |
|  | F026-245 | 1 | kit93 | 1.401 | 0.918 | 1.269 | 2.005 | 1.448 | 0.356 | 0.416 | 1.824 | 0.844 | 1.312 | 0.169 | 0.152 | 0.318 |  |
|  | F026-427 | 2 | kit93 | 2.828 | 1.975 | 3.027 | 2.689 | 1.614 | 0.538 | 0.682 | 2.725 | 1.270 | 1.865 | 0.130 | 0.450 | 0.969 | HA |
|  | F026-146 | 12 | kit93 | 2.147 | 2.277 | 1.866 | 2.470 | 2.382 | 1.112 | 1.168 | 2.120 | 2.102 | 2.393 | 0.608 | 0.647 | 0.906 | HA |
|  | F045-092 | 14 | Tok73 | 3.029 | 3.020 | 2.852 | 2.739 | 2.810 | 2.319 | 2.016 | 2.084 | 3.289 | 3.117 | 1.391 | 2.561 | 1.428 | HA |
| 12 | F075-013 | 14 | Fuk85 | 0.132 | 0.204 | 0.124 | 0.447 | 0.431 | 2.270 | 0.171 | 0.073 | 0.101 | 0.107 | 0.116 | 0.084 | 0.094 |  |
|  | F075-117 | 1 | Fuk85 | 0.117 | 0.118 | 0.075 | 0.308 | 0.301 | 2.563 | 0.130 | 0.055 | 0.073 | 0.062 | 0.202 | 0.069 | 0.097 |  |
| 13 | F077-022 | 1 | Fuk85 | 0.097 | 0.088 | 0.066 | 0.141 | 0.121 | 1.667 | 0.116 | 0.087 | 0.093 | 0.079 | 0.095 | 0.071 | 0.086 |  |
|  | F077-011 | 1 | Fuk85 | 0.131 | 0.180 | 0.120 | 0.267 | 0.212 | 1.605 | 0.214 | 0.095 | 0.130 | 0.132 | 0.145 | 0.101 | 0.127 |  |
| 14 | F018-083 | 1 | Pan99 | 0.131 | 0.159 | 0.052 | 0.156 | 0.38 | 0.032 | 0.172 | 0.032 | 1.950 | 3.060 | 0.898 | 0.274 | 0.030 | HA |

FIG.1-2

| | | | | | | | | | | | | | | | | |
|---|---|---|---|---|---|---|---|---|---|---|---|---|---|---|---|---|
| 15 | F006-110 | 1 | Wyo03 | 0.056 | 0.059 | 0.029 | 0.112 | 0.421 | 0.022 | 0.064 | 0.263 | 2.659 | 2.773 | 2.160 | 0.111 | 0.105 | HA |
| | F006-131 | 1 | Wyo03 | 0.046 | 0.061 | 0.022 | 0.072 | 0.081 | 0.033 | 0.071 | 0.030 | 2.687 | 2.819 | 2.195 | 0.035 | 0.046 | |
| 16 | F006-015 | 1 | Wyo03 | 0.037 | 0.078 | 0.034 | 0.090 | 0.099 | 0.030 | 0.112 | 0.021 | 0.025 | 0.031 | 1.799 | 0.026 | 0.022 | |
| 17 | F006-107 | 1 | Wyo 03 | 0.083 | 0.116 | 0.124 | 0.241 | 0.235 | 0.140 | 0.155 | 0.086 | 0.074 | 0.075 | 1.251 | 0.088 | 0.073 | |
| 18 | F006-148 | 1 | Wyo03 | 0.134 | 0.183 | 0.067 | 0.195 | 0.200 | 0.050 | 0.181 | 0.040 | 0.061 | 0.043 | 1.833 | 0.075 | 0.038 | |
| 19 | F006-101 | 21 | Wyo03, NY04 | 0.102 | 0.126 | 0.149 | 0.176 | 0.195 | 0.180 | 0.141 | 0.105 | 0.075 | 0.080 | 1.706 | 1.024 | 0.075 | |
| | F006-108 | 4 | Wyo03 | 0.116 | 0.168 | 0.152 | 0.222 | 0.273 | 0.163 | 0.197 | 0.109 | 0.088 | 0.084 | 1.841 | 1.121 | 0.091 | |
| | F006-121 | 1 | Wyo03 | 0.220 | 0.267 | 0.133 | 0.269 | 0.239 | 0.170 | 0.215 | 0.077 | 0.097 | 0.098 | 2.361 | 1.879 | 0.151 | |
| 20 | F006-141 | 2 | Wyo03 | 0.167 | 0.253 | 0.115 | 0.247 | 0.265 | 0.053 | 0.214 | 0.045 | 0.041 | 0.063 | 1.681 | 1.011 | 0.053 | |
| 21 | F006--012 | 2 | Wyo03 | 0.449 | 1.748 | 1.174 | 1.017 | 1.171 | 0.926 | 1.103 | 0.169 | 1.508 | 0.717 | 1.791 | 0.710 | 0.063 | |
| 22 | F005-126 | 49 | Aic68, Fuk70, Tok73 | 1.659 | 2.383 | 1.231 | 1.953 | 2.126 | 1.200 | 1.294 | 1.726 | 1.404 | 1.901 | 1.265 | 1.660 | 0.135 | HA |
| | F022-177 | 1 | Aic68 | 3.093 | 3.306 | 2.214 | 2.859 | 2.992 | 2.761 | 2.000 | 1.500 | 3.204 | 3.349 | 1.634 | 1.737 | 0.208 | |
| | F044-152 | 1 | Fuk70 | 2.522 | 3.344 | 1.130 | 1.854 | 1.850 | 1.532 | 1.211 | 0.754 | 1.943 | 2.189 | 1.518 | 1.407 | 0.198 | |
| 23 | F006-138 | 1 | Wyo03 | 0.904 | 0.544 | 0.254 | 0.694 | 1.094 | 0.337 | 1.168 | 0.192 | 0.815 | 0.442 | 2.498 | 0.211 | 0.227 | |

Aic68 A/Aichi/2/68
Fuk70 A/Fukuoka/1/70
Tok73 A/Tokyo/6/73
Fuk85 A/Fukuoka/C29/85
Kit93 A/Kitakyushu/195/93
Pan99 A/Panama/2007/99
Wyo03 A/Wyoming/3/2003
NY04 A/New York/55/2004

| Name of representative clone | Viral strains used for screening | Number of clones isolated in screening for each viral strain | Number of clones with the same VH sequence | Total number of isolated clones |
|---|---|---|---|---|
| F022-360 | Aic68 | 2 | 15 | 41 |
| | Tok73 | 1 | | |
| | Kit93 | 12 | | |
| F026-427 | Kit93 | 2 | 2 | |
| F026-245 | Kit93 | 2 | 2 | |
| F028-116 | Kit93 | 1 | 1 | |
| F026-146 | Aic68 | 1 | 20 | |
| | Tok73 | 2 | | |
| | Kit93 | 17 | | |
| F045-092 | Tok73 | 1 | 1 | |

H3N2 influenza virus strains
Aic68 : A/Aichi2/68
Tok73 : A/Tokyo/6/73
Kit93 : A/Kitakyushu/159/93

The number of clones having the same VH sequence is shown on the basis of the VH amino acid sequence of each clone.
The groups are divided according to similarity of the VH amino acid sequence of each clone.

FIG. 4

VH amino acid sequences

| Representative clone | Germline | Identity (%) to Germline FR1-FR3 | Primer | FR1 | CDR1 | FR2 | CDR2 | FR3 | CDR3 | FR4 |
|---|---|---|---|---|---|---|---|---|---|---|
|  | IGHV1-69*01 | - | QVQLVQSGAE | VKKPGSSVKVSCKASGGTFS | SYAIS | WVRQAPGQGLEWMG | GIIPIFGTANYAQKFQG | RVTITADESTSTAYMELSSLRSEDTAVYYCAR |  |  |
| F022-360 | IGHV1-69*01 | 90.9 | QVQLVQSGAE | VKKPGSSVKVSCKASGGTFH | KYAIN | WVRQAPGKGLEWMG | GIIPFFGTTNYAQKFQG | RVTITADETTRTAYMELSSLRSEDTAVYYCAR | PSRNESPYCLDCAAKDYYYGLDV | WGQGTTVTVSS |
| F026-427 | IGHV1-69*01 | 89.8 | QVQLVQSGAE | VKKPGSSVYVSCKASGGGFS | KYAIN | WVRQAPGGGLEWMG | GIIPFFGTTNYAQKFQG | RVTITADASTSTAYAMASSLISEDTAVYYCAR | PSRNESPYCLDCAAKDYYYGLDV | WGQGTTVTVSS |
| F026-245 | IGHV1-69*01 | 92.0 | QVQLVQSGAE | VKKPGSSVKVSCKASGGTFS | KYAIN | WVRQAPGQGLEWMG | GIIPFFGTTNYAQKFQG | RLTITADASTRTAYMELSLRSEDTAVYYCAR | PSITEIQYCLDCAAKDYYYGLDV | WGQGTTVTVSS |
| F026-116 | IGHV1-69*01 | 90.9 | QVQLVQSGAE | VKKPGSSVKVSCKASGGTFS | KYAIN | WVRQAPGQGLEWMG | GIIPFFGTTNYAQKFQG | RLTITADASTRTAYMELSSLRSEDTAVYYCAR | PSITESQYCLDCAAKDYYYGLDV | WGQGTTVTVSS |
| F026-146 | IGHV1-69*01 | 92.0 | QVQLVQSGAE | VKKPGSSVKVSCKASGGTFS | KYAIN | WVRQAPGQGLEWMG | GIIPFFGTTNYAQKFQG | RLTITADASTRTAYMELSSLRSEDTAVYYCAR | PSITESQYCLDCAAKDYYYGLDV | WGQGTAVTVSS |
| F045-092 | IGHV1-69*01 | 85.2 | EVQLVESGAE | VKKPGSSVKVSCKASG..TFY | KYAIN | WVRQAPGQGLEWMG | GIIPFFGTTNYAQKFQG | RLTITADGSTNTAYMQLDSLRSEDTAVYYCAG | PSITESHYCLDCAAKDYYYGLDV | WGQGTTVTVSS |

VH: Different amino acids compared with the germline are highlighted in different colors; however, for CDR3 and FR4, amino acids differing among the sequences are highlighted in different colors.

VL amino acid sequences (combinations with VH)

| Representative clone | Germline | Identity (%) to Germline | Primer | FR1 | CDR1 | FR2 | CDR2 | FR3 | CDR3 | FR4 |
|---|---|---|---|---|---|---|---|---|---|---|
|  | IGLV1-47*01 | 98.0 | QSVLTQPPSA | SGTPGQRVTISC | SGSSSNIGSNYVY | WYQQLPGTAPKLLIY | RNNQRPS | GVPDRFSGSKSGTSASLAISGLRSEDEADYYC | AAWDDSLSGAV | FGGGTQLTVLG |
|  | IGLV1-51*01 | 100.0 | QSVLTQPPSV | SAAPGQRVTISC | SGSSSNIGNNYVS | WYQQLPGTAPKLLIY | DNNKRPS | GPPDRFSGSKSGTSATLGITGLQTGREDEADYYC | GTWDSSLSASV | FGGGTKLTVLG |
|  | IGLV1-51*01 | 95.9 | QSVLTQPPSV | SAAPGQKVTISC | SGETSSNIGDMYVS | WYQQLPGTAPKLLIY | ENNQRPS | GPPDRFSGSKSGTSATLGITGLQTGQEDEADYYC | GTWDSSLSAVA | FGGGTKLTVLR |
| F022-360 | IGLV1-44*01 |  | QSVLTQPPSA | SGTPGQRVTISC | SGSSSNIGSNTVN | WYQQLPGTAPKLLIY | SNNQRPS | GVPDRFSGSKSGTSASLAISGLASGLQSEDEADYYC | AAWDDSLNGVV | FGGGTKLTVLG |
|  | IGLV1-44*01 | 100.0 | QSVLTQPPSA | SGTPGQRVTISC | SGSSSNIGSNTVN | WYQQLPGTAPKLLIY | SNNQRPS | GVPDRFSGSKSGTSASLAISGLASGLQSEDEADYYC | AAWDDSLNGVV | FGGGTQLTVLG |
|  | IGLV1-44*01 | 100.0 | QSVLTQPPSA | SGTPGQRVTISC | SGSSSNIGSNTVN | WYQQLPGTAPKLLIY | SNNQRPS | GVPDRFSGSKSGTSASLAISGLASGLQSEDEADYYC | AAWDDSLNGVV | FGGGTKLTVLG |
|  | IGLV1-44*01 | 95.9 | QSVLTQPPSA | SGTPGQRVTISC | SGCTSSNIGSNTVN | WYQQLPGTAPKLLSY | RNNQRPS | GVPDRFSGSKSGTSASLAISGLASGLQSEDEADYYC | AAWDDSLNGVV | FGGGTKLTVLG |
| F026-427 | IGLV1-44*01 | 99.0 | QSVLTQPPSA | SGTPGQRVTISC | SGSSSNIGSNTVN | WYQQLPGTAPKLLIY | SNNQRPS | GAPDRFSGSKSGTSASLAISGLASGLQSEDEADYYC | AAWDDSLNGVV | FGTGTKLTVLG |
| F026-116 | IGLV1-51*01 | 90.7 | QSVLTQPPSV | SAAPGQKVTISC | SGSSSNIGNNYVS | WYQQLPGTAPKLLIY | RGNKRPS | GVSDRFSGSKSGSSATLGITGLQTGQEDEADYYC | GTWDRLEVVL | FGGGTRLTVLS |
| F026-146 | IGLV1-44*01 | 96.9 | QSVLTQPPSA | SGTPGQRVTISC | SGSASNIGSNTVN | WYQQLPGTAPKLLIY | TNNGRPS | GVPDRFSGSKSGTSASLAISGLQSEDEADYYC | ASWDDSLNGVV | FGGGTKLTVLG |
| F045-092 | IGLV1-44*01 | 96.8 | QSVLTQPPSA | SGTPGQSVTISC | SGSSSNIGSNTVN | WYQHLPGRAPKLLIY | SENQRSS | GVPDRFSGSKSGTSASLAISGLRSEDDADYYC | ASWDDSLNGVV | FGGGTKLTVLG |

VL: Different amino acids compared with sequences exhibiting 100% identity to the germline IGLV1-44*01 are highlighted in different colors.
The sequence highlighted in grey is the VL sequence of the F022360 clone itself.
Of 15 clones with the same VH sequence as F022-360, 12 have their VL sequences already identified; as a result, the existence of combinations with 7 VL sequences was found.
For clones with VH sequences other than F022-360, only the VL sequences of the indicated clones have been identified.
The VL sequence of F022-425 remains unidentified.

FIG. 5

VH amino acid sequences

| Name of clone | Name of journal in which the clone was reported | Primer | FR1 | CDR1 | FR2 | CDR2 | FR3 | CDR3 | FR4 |
|---|---|---|---|---|---|---|---|---|---|
| IGHV1-69*01 | - | QVQLVQSGAE | VKKPGSSVKVSCKASGGTFS | SYAIS | WVRQAPGQGLEWMG | GIIPIFGTANYAQKFQG | RVTITADESTSTAYMELSSLRSEDTAVYYCAR | | WGQGTLVTVSS |
| F10 | | | ----------TS-EV---- | -F--- | ----L---- | --S-M---- | ----G--R---D-R---- | SPSYTCSGGTCYEDH | -------- |
| D8 | 2009 Nat.Struct.Mol.Biol. | | | A--FT | | ---GM---- | --------T------L-- | GLYYESSFDY | -------- |
| A66 | | | ----------P------- | MT-FT | --L----- | ---S---R--K-- | --------N---T--K-- | TLSSYGPNNGAF-AI | -------- |
| GR5261 | 2009 Sience | E--------E----- | ----------P-R---- | ---- | -----P--- | ---TK--P---- | ---DFAG--V---------M--- | HMGYQVRETMDV | ---M---- |
| 17 | | E----------- | -------R--T-------- | ---VT | | ---GM---T-- | -I----EM-------------- | GSYYYETTLSDY | ---R---- |
| 30# | | E----------- | -------R--T-------- | ---VT | | ---GM---T-- | -I----EM-------------- | GSYYYETTLSDY | ---K---- |
| 50# | 2008 PNAS | E----------- | ----------TT------- | ---VT | | ---GM---T-- | ------EM-------------- | GSYYYESSLSDY | -------- |
| 27 | | E----------- | ---Q------T-------- | ---VT | | A--GM---T-- | -L----EL-------------- | GSYYYESSLSDY | -------- |
| 33# | | E----------- | ----------T-------- | ---VT | | A--GM---T-- | ------EL-------D------ | GSYYYESSLSDY | ---K---- |
| 41* | | E----------- | ----------T-------- | ---VT | | A--GM---T-- | -L----EL-------------- | GSYYYESSLSDY | ---K--M- |
| F022-360 | | ---Q-------- | ----------------N | K---N | | ----F----T-- | -----------I-R-------- | PSINESPYCLDCAAKDYYYGLDV | ---T---- |
| F026-427 | | | ----T-------S---- | K---N | ---K--- | ----F----T-- | -----A---------S------ | PSINESPYCLDCAAKDYYYGLDV | ---T---- |
| F026-245 | Clones isolated by N library screening | | ----------------- | K---N | ---A--- | ----F----T-- | -----A---A--R-------- | PSITETRQVCLDCAAKDYYYGLDV | ---T---- |
| F026-116 | | | ----------------- | K---N | | ----F----T-- | -I---A---A--R-------- | PSITESQVCLDCAAKDYYYGLDV | ---T---- |
| F026-146 | | E--------E----- | ----T----T-------- | K---N | | ----F----T-- | -I---A---A--R-------- | PSITESQVCLDCAAKDYYYGLDV | ---M---- |
| F045-092 | | E--------E----- | -------R-----Y---- | K---N | | ----F----T-- | -I---G---N---Q--D-----G | PSITESHVCLDCAAKDYYYGLDV | ---T---- |

FIG. 8

| Antibody | HIU | | | | | | |
|---|---|---|---|---|---|---|---|
| | H3N2 | | | | H1N1 | | |
| | Aic68 | Yam77 | Kit93 | Pan99 | NC99 | SI 06 | H1N1pdm |
| F026-427PP | 2 | <2 | 8 | <2 | <2 | <2 | <2 |
| F045-092PP | 2 | <2 | 8 | 64 | <2 | <2 | <2 |
| F026-427IgG | 256 | 32 | 256 | 64 | <2 | 2 | <2 |
| F045-092IgG | 512 | 128 | 256 | 512 | 16 | 32 | <2 |

Influenza virus strains used for HI activity determination
Aic68: A/Aichi/2/68
Yam77: A/Yamanashi/2/77
Kit93: A/Kitakyushu/159/93
Pan99: A/Panama/2007/99
NC99: A/New Caledonia/20/1999
SI06: A/Solomon Islands/3/2006
H1N1pdm: A/California/7/2009 (H1N1)

FIG. 9

| (µg/mL) | Aic/68 | | Yam/77 | | Kit/93 | | NC/99 | |
|---|---|---|---|---|---|---|---|---|
| | 250 | 100 | 250 | 100 | 250 | 100 | 250 | 100 |
| F005-126 | 99 | 98.1 | 94.2 | 84.3 | 91.5 | 78.7 | 0 | 0 |
| F022-360 | 100 | 100 | 98.4 | 90 | 100 | 100 | 18.1 | 44.6 |
| F026-146 | 99 | 100 | 98.4 | 97.5 | 100 | 100 | 53 | 8.6 |
| F026-427 | 100 | 100 | 100 | 91.7 | 100 | 100 | 61.6 | 0 |
| F045-092 | 100 | 100 | 100 | 97.5 | 100 | 100 | 41 | 0 |

15-<30
30-<50
50-100

F005-126, a clone belonging to Group 22, was also subjected to the determination.

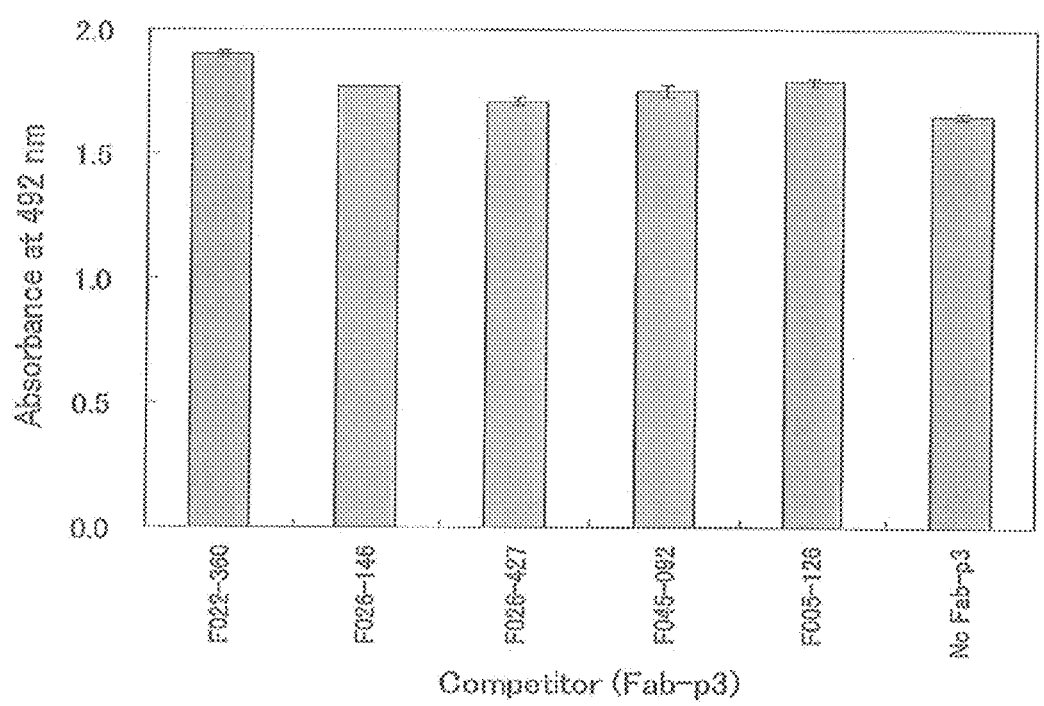

FIG. 15-1
F026-427PP
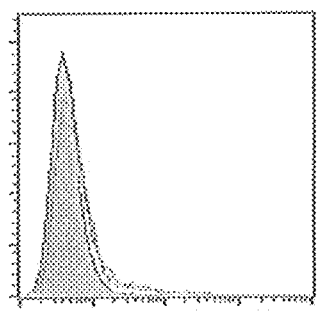
F045-092PP
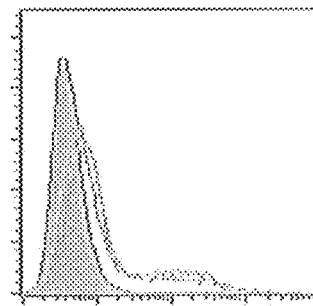
F003-137PP
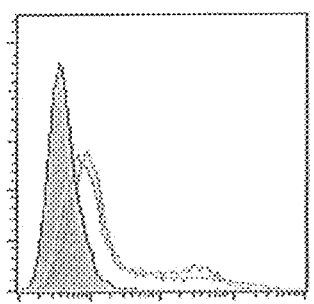
F49
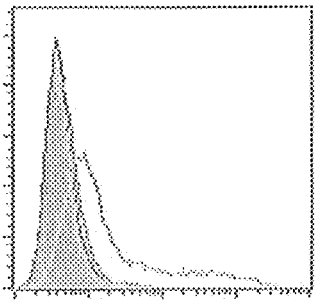
Anti-V5 antibody
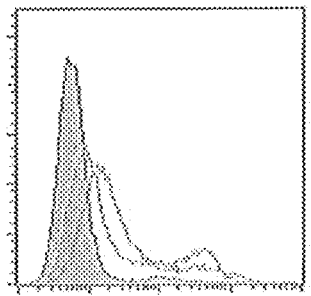

FIG. 15-2
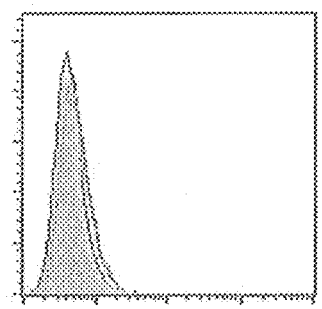
F026-427PP
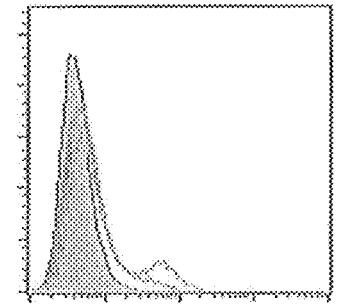
F045-092PP
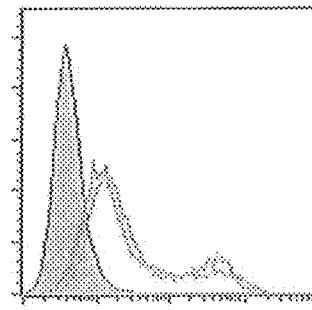
F019-102PP
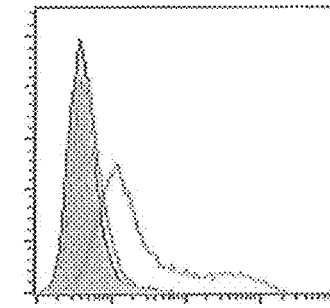
F49
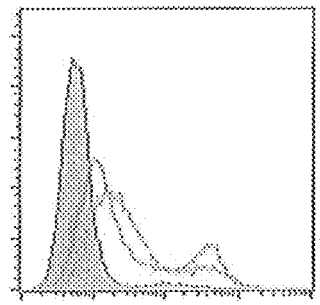
Anti-V5 antibody

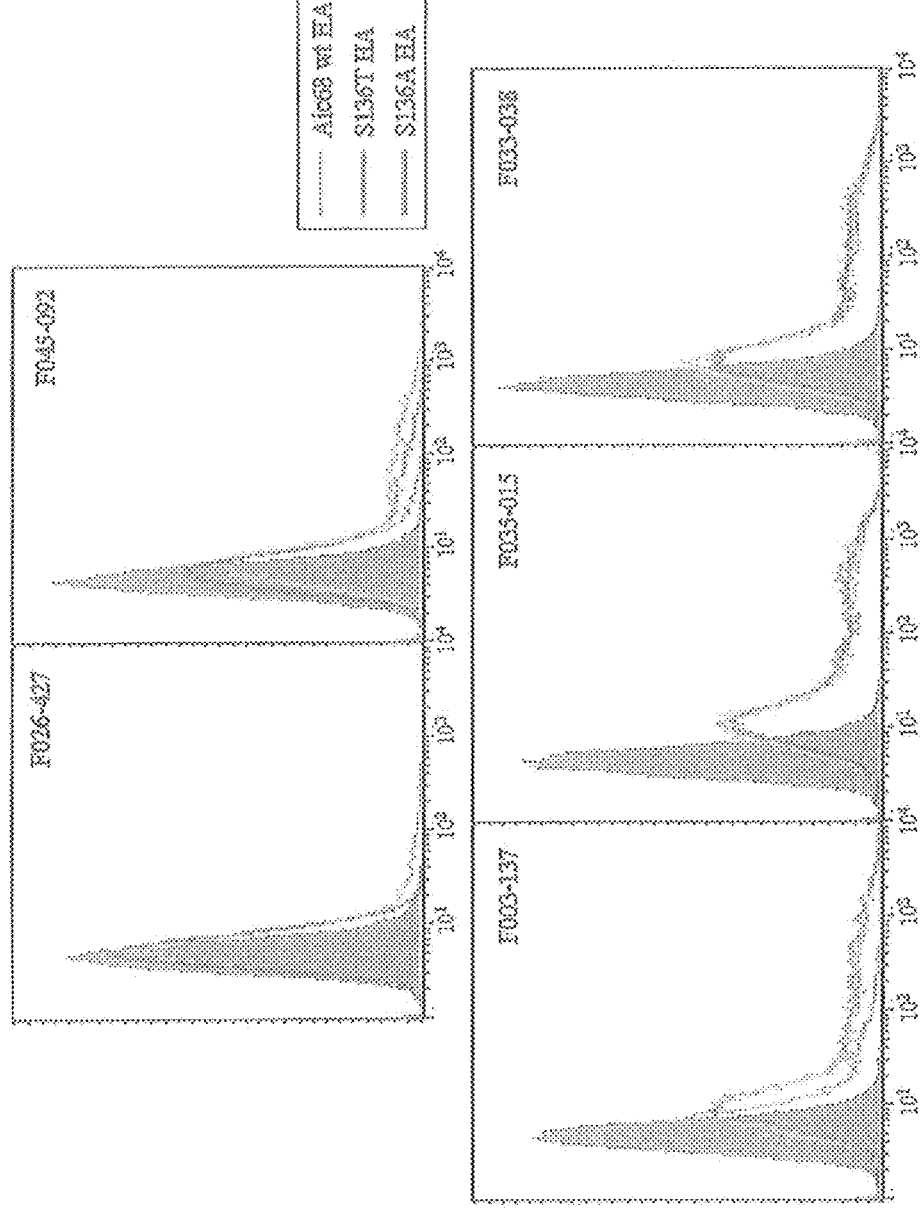

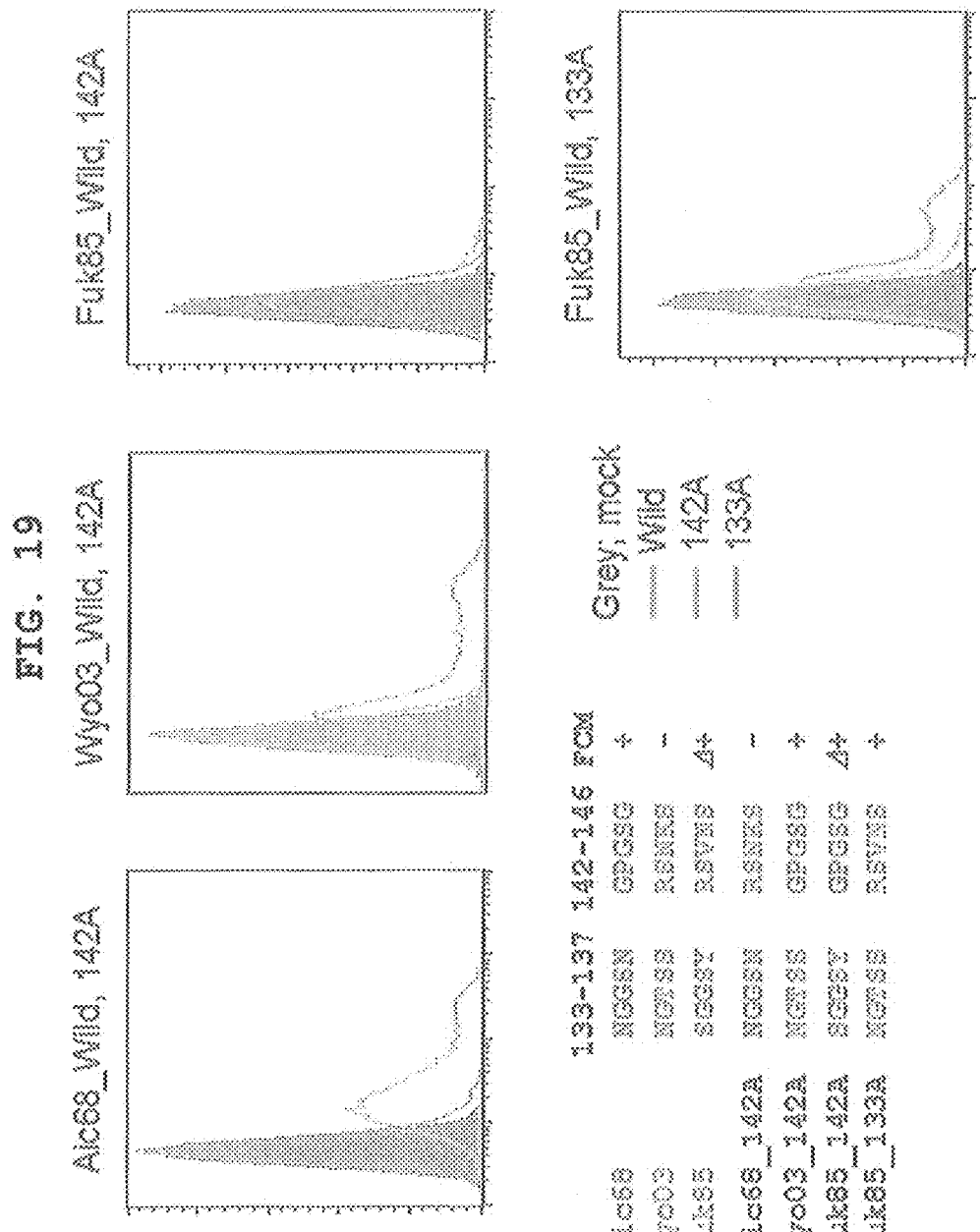

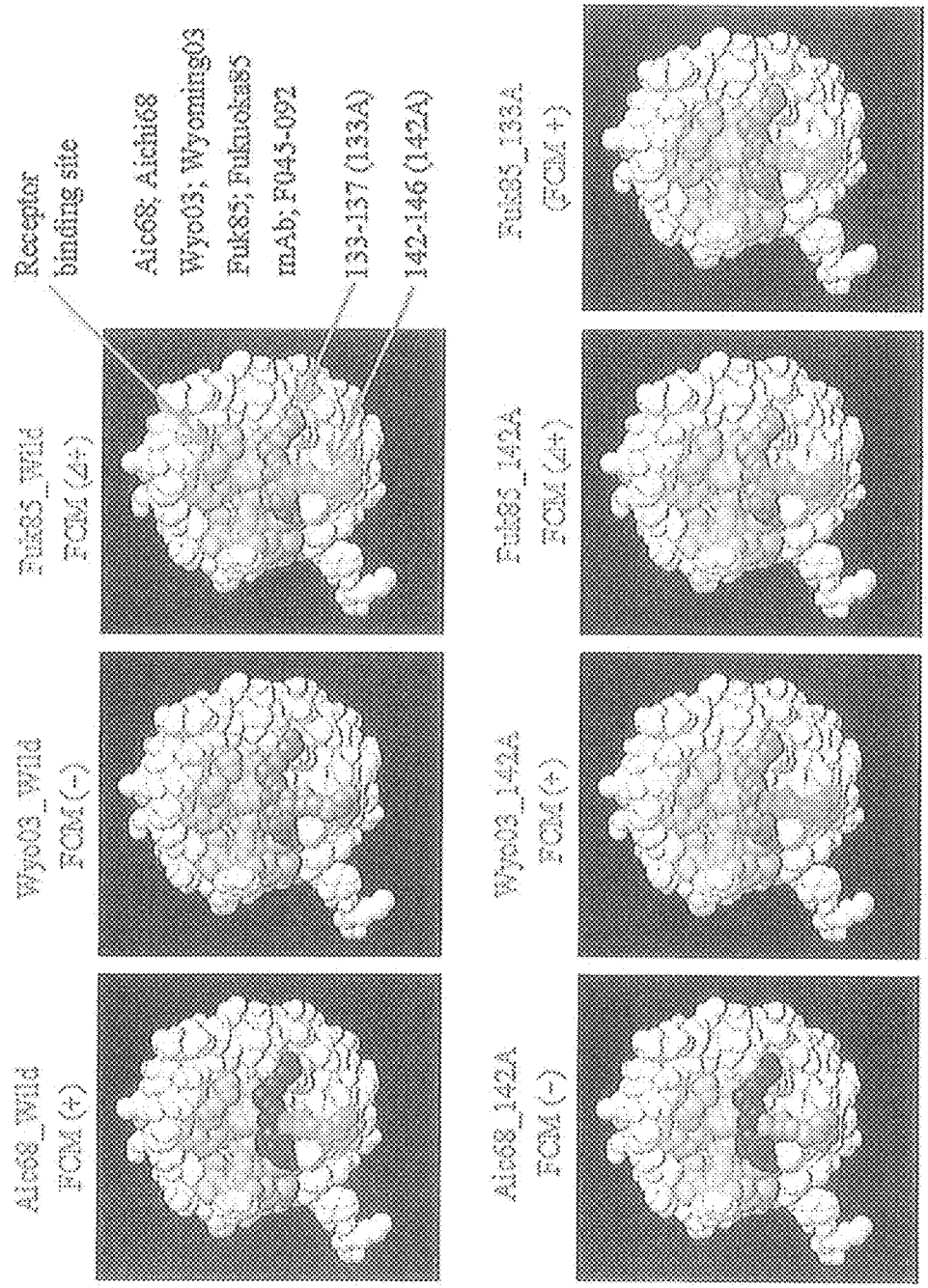

FIG. 21

Orange: amino acids in receptor-binding region
Pink: amino acids used to generate chimeras by EMAC method
Number: amino acid numbers; of the amino acids used to generate chimeras, even those involved in the receptor-binding region are shown in blue.

SEQUENCE LISTING

<160> NUMBER OF SEQ ID NOS: 88

<210> SEQ ID NO 1
<211> LENGTH: 5

```
<212> TYPE: PRT
<213> ORGANISM: Homo sapiens

<400> SEQUENCE: 1

Lys Tyr Ala Ile Asn
1               5

<210> SEQ ID NO 2
<211> LENGTH: 17
<212> TYPE: PRT
<213> ORGANISM: Homo sapiens

<400> SEQUENCE: 2

Gly Ile Ile Pro Phe Phe Gly Thr Thr Asn Tyr Ala Gln Lys Phe Gln
1               5                   10                  15

Gly

<210> SEQ ID NO 3
<211> LENGTH: 19
<212> TYPE: PRT
<213> ORGANISM: Homo sapiens

<400> SEQUENCE: 3

Val Lys Lys Pro Gly Ser Ser Val Lys Val Ser Cys Arg Ala Ser Gly
1               5                   10                  15

Thr Phe Tyr

<210> SEQ ID NO 4
<211> LENGTH: 98
<212> TYPE: PRT
<213> ORGANISM: Homo sapiens

<400> SEQUENCE: 4

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Asn Lys Tyr
                20                  25                  30

Ala Ile Asn Trp Val Arg Gln Ala Pro Gly Lys Gly Leu Glu Trp Met
            35                  40                  45

Gly Gly Ile Ile Pro Phe Phe Gly Thr Thr Asn Tyr Ala Gln Lys Phe
        50                  55                  60

Gln Gly Arg Val Thr Ile Thr Ala Asp Glu Thr Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 5
<211> LENGTH: 98
<212> TYPE: PRT
<213> ORGANISM: Homo sapiens

<400> SEQUENCE: 5

Gln Val Gln Leu Val Gln Ser Gly Ala Glu Val Lys Lys Pro Gly Ser
1               5                   10                  15

Ser Val Thr Val Ser Cys Lys Ala Ser Gly Gly Ser Phe Ser Lys Tyr
                20                  25                  30

Ala Ile Asn Trp Val Arg Gln Ala Pro Gly Gln Gly Leu Glu Trp Met
            35                  40                  45
```

```
Gly Gly Ile Ile Pro Phe Phe Gly Thr Thr Asn Tyr Ala Gln Lys Phe
            50                  55                  60

Gln Gly Arg Val Thr Ile Thr Ala Asp Ala Ser Thr Ser Thr Ala Tyr
 65                  70                  75                  80

Met Ala Leu Ser Ser Leu Ser Ser Glu Asp Thr Ala Val Tyr Tyr Cys
                 85                  90                  95

Ala Arg

<210> SEQ ID NO 6
<211> LENGTH: 98
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Lys Tyr
                 20                  25                  30

Ala Ile Asn Trp Val Arg Gln Ala Pro Gly Gln Gly Leu Glu Trp Met
             35                  40                  45

Gly Gly Ile Ile Pro Phe Phe Gly Thr Thr Asn Tyr Ala Gln Lys Phe
        50                  55                  60

Gln Gly Arg Leu Thr Ile Thr Ala Asp Ala Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 7
<211> LENGTH: 98
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Lys Tyr
                 20                  25                  30

Ala Ile Asn Trp Val Arg Gln Ala Pro Ala Gln Gly Leu Glu Trp Met
             35                  40                  45

Gly Gly Ile Ile Pro Phe Phe Gly Thr Thr Asn Tyr Ala Gln Lys Phe
        50                  55                  60

Gln Gly Arg Leu Thr Ile Thr Ala Asp Ala Ser Thr Arg Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 8
<211> LENGTH: 98
<212> TYPE: PRT
<213> ORGANISM: Homo sapiens

<400> SEQUENCE: 8

Glu Val Gln Leu Val Glu Ser Gly Ala Glu Val Lys Lys Pro Gly Ser
 1               5                  10                  15

Ser Val Lys Val Ser Cys Lys Ala Ser Gly Gly Thr Phe Ser Lys Tyr
```

```
                    20                  25                  30
Ala Ile Asn Trp Val Arg Gln Ala Pro Gly Gln Gly Leu Glu Trp Met
            35                  40                  45
Gly Gly Ile Ile Pro Phe Phe Gly Thr Thr Asn Tyr Ala Gln Lys Phe
        50                  55                  60
Gln Gly Arg Leu Thr Ile Thr Ala Asp Ala Ser Thr Arg Thr Ala Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 9
<211> LENGTH: 97
<212> TYPE: PRT
<213> ORGANISM: Homo sapiens

<400> SEQUENCE: 9

Glu Val Gln Leu Val Glu Ser Gly Ala Glu Val Lys Lys Pro Gly Ser
1               5                   10                  15
Ser Val Lys Val Ser Cys Arg Ala Ser Gly Thr Phe Tyr Lys Tyr Ala
                20                  25                  30
Ile Asn Trp Val Arg Gln Ala Pro Gly Gln Gly Leu Glu Trp Met Gly
            35                  40                  45
Gly Ile Ile Pro Phe Phe Gly Thr Thr Asn Tyr Ala Gln Lys Phe Gln
        50                  55                  60
Gly Arg Leu Thr Ile Thr Ala Asp Gly Ser Thr Asn Thr Ala Tyr Met
65                  70                  75                  80
Gln Leu Asp Ser Leu Arg Ser Glu Asp Thr Ala Val Tyr Tyr Cys Ala
                85                  90                  95
Gly

<210> SEQ ID NO 10
<211> LENGTH: 132
<212> TYPE: PRT
<213> ORGANISM: Homo sapiens

<400> SEQUENCE: 10

Gln Val Gln Leu Gln Gln Ser Gly Ala Glu Val Lys Lys Pro Gly Ser
1               5                   10                  15
Ser Val Lys Val Ser Cys Lys Ala Ser Gly Gly Thr Phe Asn Lys Tyr
                20                  25                  30
Ala Ile Asn Trp Val Arg Gln Ala Pro Gly Lys Gly Leu Glu Trp Met
            35                  40                  45
Gly Gly Ile Ile Pro Phe Phe Gly Thr Thr Asn Tyr Ala Gln Lys Phe
        50                  55                  60
Gln Gly Arg Val Thr Ile Thr Ala Asp Glu Thr Thr Arg Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Ser Ile Asn Glu Ser Pro Tyr Cys Leu Asp Cys Ala Ala
                100                 105                 110
Lys Asp Tyr Tyr Tyr Gly Leu Asp Val Trp Gly Gln Gly Thr Thr Val
            115                 120                 125
Thr Val Ser Ser
        130
```

<210> SEQ ID NO 11
<211> LENGTH: 132
<212> TYPE: PRT
<213> ORGANISM: Homo sapiens

<400> SEQUENCE: 11

Gln Val Gln Leu Val Gln Ser Gly Ala Glu Val Lys Lys Pro Gly Ser
1               5                   10                  15

Ser Val Thr Val Ser Cys Lys Ala Ser Gly Gly Ser Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Phe Phe Gly Thr Thr Asn Tyr Ala Gln Lys Phe
    50                  55                  60

Gln Gly Arg Val Thr Ile Thr Ala Asp Ala Ser Thr Ser Thr Ala Tyr
65                  70                  75                  80

Met Ala Leu Ser Ser Leu Ser Ser Glu Asp Thr Ala Val Tyr Tyr Cys
                85                  90                  95

Ala Arg Pro Ser Ile Asn Glu Ser Pro Tyr Cys Leu Asp Cys Ala Ala
            100                 105                 110

Lys Asp Tyr Tyr Tyr Gly Leu Asp Val Trp Gly Gln Gly Thr Thr Val
        115                 120                 125

Thr Val Ser Ser
    130

<210> SEQ ID NO 12
<211> LENGTH: 132
<212> TYPE: PRT
<213> ORGANISM: Homo sapiens

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Lys Tyr
            20                  25                  30

Ala Ile Asn Trp Val Arg Gln Ala Pro Gly Gln Gly Leu Glu Trp Met
        35                  40                  45

Gly Gly Ile Ile Pro Phe Phe Gly Thr Thr Asn Tyr Ala Gln Lys Phe
    50                  55                  60

Gln Gly Arg Leu Thr Ile Thr Ala Asp Ala Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Ser Ile Thr Glu Thr Gln Tyr Cys Leu Asp Cys Ala Ala
            100                 105                 110

Lys Asp Tyr Tyr Tyr Gly Leu Asp Val Trp Gly Gln Gly Thr Thr Val
        115                 120                 125

Thr Val Ser Ser
    130

<210> SEQ ID NO 13
<211> LENGTH: 132
<212> TYPE: PRT
<213> ORGANISM: Homo sapiens

<400> SEQUENCE: 13

Gln Val Gln Leu Val Gln Ser Gly Ala Glu Val Lys Lys Pro Gly Ser

```
                1               5                   10                  15
            Ser Val Lys Val Ser Cys Lys Ala Ser Gly Gly Thr Phe Ser Lys Tyr
                            20                  25                  30

Ala Ile Asn Trp Val Arg Gln Ala Pro Ala Gln Gly Leu Glu Trp Met
                        35                  40                  45

Gly Gly Ile Ile Pro Phe Phe Gly Thr Thr Asn Tyr Ala Gln Lys Phe
                    50                  55                  60

Gln Gly Arg Leu Thr Ile Thr Ala Asp Ala Ser Thr Arg Thr Ala Tyr
            65                  70                  75                  80

Met Glu Leu Ser Ser Leu Arg Ser Glu Asp Thr Ala Val Tyr Tyr Cys
                            85                  90                  95

Ala Arg Pro Ser Ile Thr Glu Ser Gln Tyr Cys Leu Asp Cys Ala Ala
                            100                 105                 110

Lys Asp Tyr Tyr Tyr Gly Leu Asp Val Trp Gly Gln Gly Thr Thr Val
                        115                 120                 125

Thr Val Ser Ser
                    130

<210> SEQ ID NO 14
<211> LENGTH: 132
<212> TYPE: PRT
<213> ORGANISM: Homo sapiens

<400> SEQUENCE: 14

Glu Val Gln Leu Val Glu Ser Gly Ala Glu Val Lys Lys Pro Gly Ser
            1               5                   10                  15

Ser Val Lys Val Ser Cys Lys Ala Ser Gly Gly Thr Phe Ser Lys Tyr
                            20                  25                  30

Ala Ile Asn Trp Val Arg Gln Ala Pro Gly Gln Gly Leu Glu Trp Met
                        35                  40                  45

Gly Gly Ile Ile Pro Phe Phe Gly Thr Thr Asn Tyr Ala Gln Lys Phe
                    50                  55                  60

Gln Gly Arg Leu Thr Ile Thr Ala Asp Ala Ser Thr Arg Thr Ala Tyr
            65                  70                  75                  80

Met Glu Leu Ser Ser Leu Arg Ser Glu Asp Thr Ala Val Tyr Tyr Cys
                            85                  90                  95

Ala Arg Pro Ser Ile Thr Glu Ser Gln Tyr Cys Leu Asp Cys Ala Ala
                            100                 105                 110

Lys Asp Tyr Tyr Tyr Gly Leu Asp Val Trp Gly Gln Gly Thr Met Val
                        115                 120                 125

Thr Val Ser Ser
                    130

<210> SEQ ID NO 15
<211> LENGTH: 131
<212> TYPE: PRT
<213> ORGANISM: Homo sapiens

<400> SEQUENCE: 15

Glu Val Gln Leu Val Glu Ser Gly Ala Glu Val Lys Lys Pro Gly Ser
            1               5                   10                  15

Ser Val Lys Val Ser Cys Arg Ala Ser Gly Thr Phe Tyr Lys Tyr Ala
                            20                  25                  30

Ile Asn Trp Val Arg Gln Ala Pro Gly Gln Gly Leu Glu Trp Met Gly
                        35                  40                  45

Gly Ile Ile Pro Phe Phe Gly Thr Thr Asn Tyr Ala Gln Lys Phe Gln
```

```
            50                  55                  60
Gly Arg Leu Thr Ile Thr Ala Asp Gly Ser Thr Asn Thr Ala Tyr Met
 65                  70                  75                  80

Gln Leu Asp Ser Leu Arg Ser Glu Asp Thr Ala Val Tyr Tyr Cys Ala
                 85                  90                  95

Gly Pro Ser Ile Thr Glu Ser His Tyr Cys Leu Asp Cys Ala Ala Lys
             100                 105                 110

Asp Tyr Tyr Gly Leu Asp Val Trp Gly Gln Gly Thr Thr Val Thr
         115                 120                 125

Val Ser Ser
    130

<210> SEQ ID NO 16
<211> LENGTH: 111
<212> TYPE: PRT
<213> ORGANISM: Homo sapiens

<400> SEQUENCE: 16

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Phe Val Tyr Trp Tyr Gln Gln Leu Pro Gly Thr Ala Pro Lys Leu Leu
         35                  40                  45

Ile Tyr Arg Asn Asn Gln Arg Pro Ser Gly Val Pro Asp Arg Phe Ser
 50                  55                  60

Gly Ser Arg Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Ala Val Phe Gly Gly Gly Thr Gln Leu Thr Val Leu Gly
             100                 105                 110

<210> SEQ ID NO 17
<211> LENGTH: 111
<212> TYPE: PRT
<213> ORGANISM: Homo sapiens

<400> SEQUENCE: 17

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Val Phe Gly Gly Gly Thr Lys Leu Thr Val Leu Gly
             100                 105                 110

<210> SEQ ID NO 18
<211> LENGTH: 111
<212> TYPE: PRT
```

<213> ORGANISM: Homo sapiens

<400> SEQUENCE: 18

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
            20                  25                  30

Tyr Val Ser Trp Tyr Gln Gln Val Pro Gly Thr Ala Pro Lys Leu Leu
        35                  40                  45

Ile Tyr Asp Asn Asn Gln Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Leu Phe Gly Gly Gly Thr Lys Leu Thr Val Leu Arg
            100                 105                 110

<210> SEQ ID NO 19
<211> LENGTH: 111
<212> TYPE: PRT
<213> ORGANISM: Homo sapiens

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Gly Thr Ser Asn Ile Gly Ser Asn
            20                  25                  30

Thr Val Asn Trp Tyr Gln Gln Leu Pro Gly Thr Ala Pro Lys Leu Leu
        35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 20
<211> LENGTH: 111
<212> TYPE: PRT
<213> ORGANISM: Homo sapiens

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

-continued

Asn Gly Val Val Phe Gly Gly Gly Thr Lys Leu Thr Val Leu Gly
            100                 105                 110

<210> SEQ ID NO 21
<211> LENGTH: 112
<212> TYPE: PRT
<213> ORGANISM: Homo sapiens

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Ala Val Phe Gly Gly Gly Thr Gln Leu Thr Val Leu Gly
            100                 105                 110

<210> SEQ ID NO 22
<211> LENGTH: 111
<212> TYPE: PRT
<213> ORGANISM: Homo sapiens

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Gly Thr Ser Asn Ile Gly Ser Asn
            20                  25                  30

Thr Val Asn Trp Tyr Gln Gln Leu Pro Gly Thr Ala Pro Lys Leu Leu
            35                  40                  45

Met Tyr Asn Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 23
<211> LENGTH: 111
<212> TYPE: PRT
<213> ORGANISM: Homo sapiens

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

```
Ile Tyr Ser Asn Asn Gln Arg Pro Ser Gly Ala Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110

<210> SEQ ID NO 24
<211> LENGTH: 111
<212> TYPE: PRT
<213> ORGANISM: Homo sapiens

<400> SEQUENCE: 24

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Asp Val Ser Trp Tyr Gln Gln Leu Pro Gly Thr Ala Pro Lys Leu Leu
            35                  40                  45

Leu Tyr Asp Asp Asn Lys Arg Pro Ser Gly Val Ser Asp Arg Phe Ser
        50                  55                  60

Gly Ser Lys Ser Gly Ala Ser Ala Thr Leu Asp Ile Thr Gly Leu Gln
65                  70                  75                  80

Thr Gly Asp Glu Ala Asp Tyr Tyr Cys Gly Thr Trp Asp Asn Ile Leu
                85                  90                  95

Ser Val Val Leu Phe Gly Gly Gly Thr Arg Leu Thr Val Leu Ser
            100                 105                 110

<210> SEQ ID NO 25
<211> LENGTH: 111
<212> TYPE: PRT
<213> ORGANISM: Homo sapiens

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Val Val Phe Gly Gly Gly Thr Lys Leu Thr Val Leu Gly
            100                 105                 110

<210> SEQ ID NO 26
<211> LENGTH: 111
<212> TYPE: PRT
<213> ORGANISM: Homo sapiens

<400> SEQUENCE: 26

Gln Ser Val Leu Thr Gln Pro Pro Ser Ala Ser Gly Thr Pro Gly Gln
```

```
                1               5                  10                 15
            Ser Val Thr Ile Ser Cys Ser Gly Ser Arg Ser Asn Ile Gly Gly Asn
                          20                  25                 30

Thr Val Asn Trp Tyr Gln His Leu Pro Gly Met Ala Pro Lys Leu Leu
                          35                  40                 45

Ile Tyr Ser Ser Asn Gln Arg Ser Ser Gly Val Pro Asp Arg Phe Ser
                      50                  55                 60

Gly Ser Lys Ser Gly Thr Ser Ala Ser Leu Ala Ile Ser Gly Leu Gln
            65                  70                  75                 80

Ser Glu Asp Asp Ala Asp Tyr Tyr Cys Ala Ser Trp Asp Asp Ser Leu
                              85                  90                 95

Asn Gly Val Val Phe Gly Gly Gly Thr Lys Leu Thr Val Leu Gly
                          100                 105                110

<210> SEQ ID NO 27
<211> LENGTH: 98
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
            1               5                  10                 15

Ser Val Lys Val Ser Cys Lys Ala Ser Gly Gly Thr Phe Ser Ser Tyr
                          20                  25                 30

Ala Ile Ser Trp Val Arg Gln Ala Pro Gly Gln Gly Leu Glu Trp Met
                          35                  40                 45

Gly Gly Ile Ile Pro Ile Phe Gly Thr Ala Asn Tyr Ala Gln Lys Phe
                      50                  55                 60

Gln Gly Arg Val Thr Ile Thr Ala Asp Glu Ser Thr Ser Thr Ala Tyr
            65                  70                  75                 80

Met Glu Leu Ser Ser Leu Arg Ser Glu Asp Thr Ala Val Tyr Tyr Cys
                              85                  90                 95

Ala Arg

<210> SEQ ID NO 28
<211> LENGTH: 328
<212> TYPE: PRT
<213> ORGANISM: Influenza A virus

<400> SEQUENCE: 28

Gln Asp Leu Pro Gly Asn Asp Asn Ser Thr Ala Thr Leu Cys Leu Gly
            1               5                  10                 15

His His Ala Val Pro Asn Gly Thr Leu Val Lys Thr Ile Thr Asp Asp
                          20                  25                 30

Gln Ile Glu Val Thr Asn Ala Thr Glu Leu Val Gln Ser Ser Ser Thr
                          35                  40                 45

Gly Lys Ile Cys Asn Asn Pro His Arg Ile Leu Asp Gly Ile Asp Cys
                      50                  55                 60

Thr Leu Ile Asp Ala Leu Leu Gly Asp Pro His Cys Asp Val Phe Gln
            65                  70                  75                 80

Asn Glu Thr Trp Asp Leu Phe Val Glu Arg Ser Lys Ala Phe Ser Asn
                              85                  90                 95

Cys Tyr Pro Tyr Asp Val Pro Asp Tyr Ala Ser Leu Arg Ser Leu Val
                          100                 105                110

Ala Ser Ser Gly Thr Leu Glu Phe Ile Thr Glu Gly Phe Thr Trp Thr
                          115                 120                125
```

```
Gly Val Thr Gln Asn Gly Gly Ser Asn Ala Cys Lys Arg Gly Pro Gly
            130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
                180                 185                 190

Ser Leu Tyr Val Gln Ala Ser Gly Arg Val Thr Val Ser Thr Arg Arg
            195                 200                 205

Ser Gln Gln Thr Ile Ile Pro Asn Ile Gly Ser Arg Pro Trp Val Arg
210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
                260                 265                 270

Pro Ile Asp Thr Cys Ile Ser Glu Cys Ile Thr Pro Asn Gly Ser Ile
            275                 280                 285

Pro Asn Asp Lys Pro Phe Gln Asn Val Asn Lys Ile Thr Tyr Gly Ala
290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr
                325

<210> SEQ ID NO 29
<211> LENGTH: 221
<212> TYPE: PRT
<213> ORGANISM: Influenza A virus

<400> SEQUENCE: 29

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
                20                  25                  30

Gly Gln Ala Ala Asp Leu Lys Ser Thr Gln Ala Ala Ile Asp Gln Ile
            35                  40                  45

Asn Gly Lys Leu Asn Arg Val Ile Glu Lys Thr Asn Glu Lys Phe His
50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
```

165                 170                 175
Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
    210                 215                 220

<210> SEQ ID NO 30
<211> LENGTH: 328
<212> TYPE: PRT
<213> ORGANISM: Influenza A virus

<400> SEQUENCE: 30

Gln Asp Leu Pro Arg Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Gly Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asp Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr
            325

<210> SEQ ID NO 31
<211> LENGTH: 221
<212> TYPE: PRT
<213> ORGANISM: Influenza A virus

<400> SEQUENCE: 31

Gly Ile Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Ile Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
    210                 215                 220

<210> SEQ ID NO 32
<211> LENGTH: 328
<212> TYPE: PRT
<213> ORGANISM: Influenza A virus

<400> SEQUENCE: 32

Gln Asp Phe Pro Gly Asn Asp Asn Ser Thr Ala Thr Le

```
Cys Tyr Pro Tyr Asp Val Pro Asp Tyr Ala Ser Leu Arg Ser Leu Val
                100                 105                 110

Ala Ser Ser Gly Thr Leu Glu Phe Ile Asn Glu Gly Phe Thr Trp Thr
            115                 120                 125

Gly Val Thr Gln Asn Gly Gly Ser Asn Ala Cys Lys Arg Gly Pro Asp
        130                 135                 140

Ser Gly Phe Phe Ser Arg Leu Asn Trp Leu Tyr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asp Gln Glu Gln Thr
            180                 185                 190

Asn Leu Tyr Val Gln Ala Ser Gly Arg Val Thr Val Ser Thr Lys Arg
        195                 200                 205

Ser Gln Gln Thr Ile Ile Pro Asn Ile Gly Ser Arg Pro Trp Val Arg
210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Gly Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr
                325

<210> SEQ ID NO 33
<211> LENGTH: 221
<212> TYPE: PRT
<213> ORGANISM: Influenza A virus

<400> SEQUENCE: 33

Gly Ile Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly His Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140
```

```
Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
210                 215                 220

<210> SEQ ID NO 34
<211> LENGTH: 328
<212> TYPE: PRT
<213> ORGANISM: Influenza A virus

<400> SEQUENCE: 34

Gln Asn Leu Pro Arg Asn Asp Asn Ser Thr Ala Thr Leu Cys Leu Gly
1               5                   10                  15

His His Ala Val Pro Asn Gly Thr Leu Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Arg Ile Cys Asp Ser Pro His Arg Ile Leu Asp Gly Lys Asn Cys
    50                  55                  60

Thr Leu Ile Asp Ala Leu Leu Gly Asp Pro His Cys Asp Gly Phe Gln
65                  70                  75                  80

Asn Glu Lys Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Asn Glu Gly Phe Asn Trp Thr
        115                 120                 125

Gly Val Thr Gln Asn Gly Gly Ser Tyr Ala Cys Lys Arg Gly Pro Asp
130                 135                 140

Asn Ser Phe Phe Ser Arg Leu Asn Trp Leu Tyr Glu Ser Glu Ser Lys
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asp Lys Glu Gln Thr
            180                 185                 190

Asn Leu Tyr Val Gln Ala Ser Gly Arg Val Thr Val Ser Thr Lys Arg
        195                 200                 205

Ser Gln Gln Thr Ile Ile Pro Asn Val Gly Ser Arg Pro Trp Val Arg
210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Asn Gly Asn Leu Ile Ala Pro Arg Gly
                245                 250                 255

Tyr Phe Lys Ile Arg Thr Gly Lys Ser Ser Ile Met Arg Ser Asp Ala
            260                 265                 270

Pro Ile Gly Thr Cys Ser Ser Glu Cys Ile Thr Pro Asn Gly Ser Ile
        275                 280                 285

Pro Asn Asp Lys Pro Phe Gln Asn Val Asn Lys Ile Thr Tyr Gly Ala
```

```
                    290                 295                 300
Cys Pro Lys Tyr Val Lys Gln Asn Thr Leu Lys Leu Ala Thr Gly Met
305                 310                 315                 320

Arg Asn Val Pro Glu Lys Gln Thr
                325
```

<210> SEQ ID NO 35
<211> LENGTH: 221
<212> TYPE: PRT
<213> ORGANISM: Influenza A virus

<400> SEQUENCE: 35

```
Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220
```

<210> SEQ ID NO 36
<211> LENGTH: 328
<212> TYPE: PRT
<213> ORGANISM: Influenza A virus

<400> SEQUENCE: 36

```
Gln Asn Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Arg Ile Cys Asp Ser Pro His Arg Ile Leu Asp Gly Lys Asn Cys
    50                  55                  60

Thr Leu Ile Asp Ala Leu Leu Gly Asp Pro His Cys Asp Gly Phe Gln
```

```
                65                  70                  75                  80
Asn Glu Lys Trp Asp Leu Phe Val Glu Arg Ser Lys Ala Phe Ser Asn
                    85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Ile Asn Glu Gly Phe Asn Trp Thr
            115                 120                 125

Gly Val Thr Gln Ser Gly Gly Ser Tyr Thr Cys Lys Arg Gly Ser Asp
        130                 135                 140

Asn Ser Phe Phe Ser Arg Leu Asn Trp Leu Tyr Glu Ser Glu Ser Lys
145                 150                 155                 160

Tyr Pro Ala Leu Asn Val Thr Met Pro Asn Asn Gly Asn Phe Asp Lys
                165                 170                 175

Leu Tyr Ile Trp Gly Val His His Pro Ser Thr Asp Lys Glu Gln Thr
                180                 185                 190

Lys Leu Tyr Val Arg Ala Ser Gly Arg Val Thr Val Ser Thr Lys Arg
            195                 200                 205

Ser Gln Gln Thr Ile Ile Pro Asn Ile Gly Pro Arg Pro Trp Val Arg
        210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Ser Gly Asn Leu Ile Ala Pro Arg Gly
                245                 250                 255

Tyr Phe Lys Ile Arg Thr Gly Lys Ser Ser Ile Met Arg Ser Asp Ala
                260                 265                 270

Pro Ile Gly Thr Cys Ser Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Lys Tyr Val Lys Gln Asn Thr Leu Lys Leu Ala Thr Gly Met
305                 310                 315                 320

Arg Asn Ile Pro Glu Lys Gln Thr
                325

<210> SEQ ID NO 37
<211> LENGTH: 221
<212> TYPE: PRT
<213> ORGANISM: Influenza A virus

<400> SEQUENCE: 37

Gly Ile Phe Gly Ala Ile Ala Gly Phe Ile Glu Asn Gly Trp Glu Gly
1               5                   10                  15

Met Val Asp Gly Trp Tyr Gly Phe Gly His Gln Asn Ser Glu Gly Thr
                20                  25                  30

Gly Gln Ala Ala Asp Leu Lys Ser Thr Gln Ala Ala Ile Asp Gln Ile
            35                  40                  45

Asn Gly Lys Leu Asn Arg Val Ile Glu Lys Thr Asn Glu Lys Phe His
        50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
                100                 105                 110
```

```
Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
        130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 38
<211> LENGTH: 328
<212> TYPE: PRT
<213> ORGANISM: Influenza A virus

<400> SEQUENCE: 38

Gln Lys Leu Pro Gly Asn Asp Asn Ser Lys Ala Thr Leu Cys Leu Gly
1               5                   10                  15

His His Ala Val Pro Asn Gly Thr Leu Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Arg Ile Cys Asp Ser Pro His Arg Ile Leu Asp Gly Lys Asn Cys
50                  55                  60

Thr Leu Ile Asp Ala Leu Leu Gly Asp Pro His Cys Asp Gly Phe Gln
65                  70                  75                  80

Asn Glu Lys Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Asn Glu Asp Phe Asn Trp Thr
        115                 120                 125

Gly Val Thr Gln Ser Gly Gly Ser Tyr Ala Cys Lys Arg Gly Ser Val
    130                 135                 140

Asn Ser Phe Phe Ser Arg Leu Asn Trp Leu His Glu Ser Glu Tyr Lys
145                 150                 155                 160

Tyr Pro Ala Leu Asn Val Thr Met Pro Asn Asn Gly Lys Phe Asp Lys
                165                 170                 175

Leu Tyr Ile Trp Gly Val His His Pro Ser Thr Asp Lys Glu Gln Thr
            180                 185                 190

Lys Leu Tyr Val Arg Ala Ser Gly Arg Val Thr Val Ser Thr Lys Arg
        195                 200                 205

Ser Gln Gln Thr Val Ile Pro Asn Ile Gly Ser Arg Pro Trp Val Arg
    210                 215                 220

Gly Leu Ser Ser Gly Ile Ser Ile Tyr Trp Thr Ile Val Lys Pro Gly
225                 230                 235                 240

Asp Ile Leu Leu Ile Asn Ser Ile Gly Asn Leu Ile Ala Pro Arg Gly
                245                 250                 255

Tyr Phe Lys Ile Arg Thr Gly Lys Ser Ser Ile Met Arg Ser Asp Ala
            260                 265                 270
```

Pro Ile Gly Thr Cys Ser Ser Glu Cys Ile Thr Pro Asn Gly Ser Ile
            275                 280                 285

Pro Asn Asp Lys Pro Phe Gln Asn Val Asn Lys Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 39
<211> LENGTH: 221
<212> TYPE: PRT
<213> ORGANISM: Influenza A virus

<400> SEQUENCE: 39

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Leu Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 40
<211> LENGTH: 328
<212> TYPE: PRT
<213> ORGANISM: Influenza A virus

<400> SEQUENCE: 40

Gln Lys Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asn Asp
            20                  25                  30

Gln Ile Glu Val Thr Asn Ala Thr Glu Leu Val His Ser Ser Ser Thr
        35                  40                  45

-continued

Gly Arg Ile Cys Asp Ser Pro His Arg Ile Leu Asp Gly Lys Asn Cys
 50                  55                  60

Thr Leu Ile Asp Ala Leu Leu Gly Asp Pro His Cys Asp Gly Phe Gln
 65                  70                  75                  80

Asn Lys Glu Trp Asp Leu Phe Val Glu Arg Ser Lys Ala Tyr Ser Asn
                 85                  90                  95

Cys Tyr Pro Tyr Asp Val Pro Asp Tyr Ala Ser Leu Arg Ser Leu Val
             100                 105                 110

Ala Ser Ser Gly Thr Leu Glu Phe Ile Asn Glu Asp Phe Asn Trp Thr
         115                 120                 125

Gly Val Ala Gln Ser Gly Gly Ser Tyr Ala Cys Lys Arg Gly Ser Ile
 130                 135                 140

Asn Ser Phe Phe Ser Arg Leu Asn Trp Leu His Glu Ser Glu His Lys
145                 150                 155                 160

Tyr Pro Ala Leu Asn Val Thr Met Pro Asn Asn Gly Lys Phe Asp Lys
                165                 170                 175

Leu Tyr Ile Trp Gly Val His His Pro Ile Thr Asp Arg Glu Gln Thr
            180                 185                 190

Asn Leu Tyr Val Arg Ala Ser Gly Arg Val Thr Val Ser Thr Lys Arg
        195                 200                 205

Ser Gln Gln Thr Val Ile Pro Asn Ile Gly Ser Arg Pro Trp Val Arg
210                 215                 220

Gly Leu Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Thr Gly Lys Ser Ser Ile Met Arg Ser Asp Ala
            260                 265                 270

Pro Ile Gly Thr Cys Ser Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 41
<211> LENGTH: 328
<212> TYPE: PRT
<213> ORGANISM: Influenza A virus

<400> SEQUENCE: 41

Gln Lys Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asn Asp
             20                  25                  30

Gln Ile Glu Val Thr Asn Ala Thr Glu Leu Val Gln Ser Ser Ser Thr
         35                  40                  45

Gly Arg Ile Cys Asp Ser Pro His Arg Ile Leu Asp Gly Lys Asn Cys
 50                  55                  60

Thr Leu Ile Asp Ala Leu Leu Gly Asp Pro His Cys Asp Gly Phe Gln
 65                  70                  75                  80

Asn Lys Glu Trp Asp Leu Phe Val Glu Arg Ser Lys Ala Tyr Ser Asn

```
                        85                  90                  95
Cys Tyr Pro Tyr Asp Val Pro Asp Tyr Ala Ser Leu Arg Ser Leu Val
                100                 105                 110

Ala Ser Ser Gly Thr Leu Glu Phe Ile Asn Glu Asp Phe Asn Trp Thr
            115                 120                 125

Gly Val Ala Gln Asp Gly Gly Ser Tyr Ala Cys Lys Arg Gly Ser Val
        130                 135                 140

Asn Ser Phe Phe Ser Arg Leu Asn Trp Leu His Lys Ser Glu Tyr Lys
145                 150                 155                 160

Tyr Pro Ala Leu Asn Val Ser Met Pro Asn Asn Gly Lys Phe Asp Lys
                165                 170                 175

Leu Tyr Ile Trp Gly Val His His Pro Ser Thr Asp Ser Asp Gln Thr
                180                 185                 190

Ser Leu Tyr Val Gln Ala Ser Gly Arg Val Thr Val Ser Thr Lys Arg
            195                 200                 205

Ser Gln Gln Thr Val Thr Pro Asn Ile Gly Ser Arg Pro Trp Val Arg
        210                 215                 220

Gly Gln Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Asn Gly Lys Ser Ser Ile Met Arg Ser Asp Ala
                260                 265                 270

Pro Ile Gly Thr Cys Ser Phe Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 42
<211> LENGTH: 328
<212> TYPE: PRT
<213> ORGANISM: Influenza A virus

<400> SEQUENCE: 42

Gln Lys Ile Pro Gly Asn Asp Asn Ser Thr Ala Thr Leu Cys Leu Gly
1               5                   10                  15

His His Ala Val Pro Asn Gly Thr Leu Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Arg Ile Cys Asp Ser Pro His Arg Ile Leu Asp Gly Glu Asn Cys
        50                  55                  60

Thr Leu Ile Asp Ala Leu Leu Gly Asp Pro His Cys Asp Gly Phe Gln
65                  70                  75                  80

Asn Lys Glu Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asn Glu Ser Phe Asn Trp Thr
            115                 120                 125
```

Gly Val Ala Gln Asn Gly Thr Ser Tyr Ala Cys Lys Arg Ser Ser Ile
            130                 135                 140

Lys Ser Phe Phe Ser Arg Leu Asn Trp Leu His Gln Leu Lys Tyr Lys
145                 150                 155                 160

Tyr Pro Ala Leu Asn Val Thr Met Pro Asn Asn Asp Lys Phe Asp Lys
                165                 170                 175

Leu Tyr Ile Trp Gly Val His His Pro Ser Thr Asp Ser Asp Gln Thr
            180                 185                 190

Ser Ile Tyr Ala Gln Ala Ser Gly Arg Val Thr Val Ser Thr Lys Arg
        195                 200                 205

Ser Gln Gln Thr Val Ile Pro Asn Ile Gly Ser Arg Pro Trp Val Arg
210                 215                 220

Gly Ile Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 43
<211> LENGTH: 221
<212> TYPE: PRT
<213> ORGANISM: Influenza A virus

<400> SEQUENCE: 43

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Arg Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

```
Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
            195                 200                 205

Ala Cys Gln Lys Gly Asn Ile Arg Cys Asn Ile Cys Ile
            210                 215                 220

<210> SEQ ID NO 44
<211> LENGTH: 328
<212> TYPE: PRT
<213> ORGANISM: Influenza A virus

<400> SEQUENCE: 44

Gln Lys Leu Pro Gly Asn Asp Asn Ser Thr Ala Thr Leu Cys Leu Gly
1               5                   10                  15

His His Ala Val Ser Asn Gly Thr Leu Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Arg Ile Cys Asp Ser Pro His Gln Ile Leu Asp Gly Glu Asn Cys
    50                  55                  60

Thr Leu Ile Asp Ala Leu Leu Gly Asp Pro His Cys Asp Gly Phe Gln
65                  70                  75                  80

Asn Lys Glu Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Ala Gln Asn Gly Thr Ser Ser Ala Cys Lys Arg Arg Ser Asn
    130                 135                 140

Lys Ser Phe Phe Ser Arg Leu Asn Trp Leu His Gln Leu Lys Tyr Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Ser Thr Asp Ser Asp Gln Ile
            180                 185                 190

Ser Ile Tyr Ala Gln Ala Ser Gly Arg Val Thr Val Ser Thr Lys Arg
        195                 200                 205

Ser Gln Gln Thr Val Ile Pro Asn Ile Gly Ser Ser Pro Trp Val Arg
    210                 215                 220

Gly Val Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
```

<210> SEQ ID NO 45
<211> LENGTH: 221
<212> TYPE: PRT
<213> ORGANISM: Influenza A virus

<400> SEQUENCE: 45

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 46
<211> LENGTH: 328
<212> TYPE: PRT
<213> ORGANISM: Influenza A virus

<400> SEQUENCE: 46

```
Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
```

```
                    100                 105                 110
Ala Ser Ser Gly Thr Leu Glu Phe Asn Asn Glu Ser Phe Asn Trp Ala
            115                 120                 125

Gly Val Thr Gln Asn Gly Thr Ser Ser Ala Cys Lys Arg Arg Ser Asn
        130                 135                 140

Lys Ser Phe Phe Ser Arg Leu Asn Trp Leu Thr His Leu Lys Tyr Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Ser Asp Gln Ile
            180                 185                 190

Ser Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Val Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 47
<211> LENGTH: 221
<212> TYPE: PRT
<213> ORGANISM: Influenza A virus

<400> SEQUENCE: 47

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140
```

```
Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
            165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Ala Leu Leu Gly Phe Ile Met Trp
            195                 200                 205

Ala Cys Gln Lys Gly Asn Ile Arg Cys Asn Ile Cys Ile
210                 215                 220

<210> SEQ ID NO 48
<211> LENGTH: 328
<212> TYPE: PRT
<213> ORGANISM: Influenza A virus

<400> SEQUENCE: 48

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
            115                 120                 125

Gly Val Thr Gln Asn Gly Thr Ser Ser Ser Cys Lys Arg Arg Ser Asn
130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Val Thr Asp Asn Asp Gln Ile
            180                 185                 190

Arg Leu Tyr Ala Gln Ala Ser Gly Arg Ile Thr Val Ser Thr Lys Arg
            195                 200                 205

Ser Gln Gln Thr Val Ile Pro Asn Ile Gly Ser Arg Pro Arg Val Arg
        210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300
```

```
Cys Pro Arg Tyr Val Lys Gln Asn Thr Leu Lys Leu Ala Thr Gly Met
305                 310                 315                 320

Arg Asn Val Pro Glu Lys Gln Thr
                325

<210> SEQ ID NO 49
<211> LENGTH: 221
<212> TYPE: PRT
<213> ORGANISM: Influenza A virus

<400> SEQUENCE: 49

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Ile
                20                  25                  30

Gly Gln Ala Ala Asp Leu Lys Ser Thr Gln Ala Ala Ile Asn Gln Ile
            35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 50
<211> LENGTH: 328
<212> TYPE: PRT
<213> ORGANISM: Influenza A virus

<400> SEQUENCE: 50

Gln Asp Leu Ser Gly Asn Asp Asn Ser Thr Ala Thr Leu Cys Leu Gly
1               5                   10                  15

His His Ala Val Ser Asn Gly Thr Val Val Lys Thr Ile Thr Asp Asp
                20                  25                  30

Arg Val Glu Val Thr Asn Ala Thr Glu Leu Val Gln Ser Ser Ser Thr
            35                  40                  45

Gly Lys Ile Cys Asn Asn Pro His Arg Ile Leu Asp Gly Arg Asp Cys
    50                  55                  60

Thr Leu Ile Asp Ala Leu Leu Gly Asp Pro His Cys Asp Val Phe Gln
65                  70                  75                  80
```

```
Asp Glu Thr Trp Asp Leu Phe Ile Glu Arg Ser Asn Ala Phe Ser Asn
                85                  90                  95

Cys Tyr Pro Tyr Asp Val Pro Asp His Ala Ser Leu Arg Ser Leu Val
            100                 105                 110

Ala Ser Ser Gly Thr Leu Glu Phe Ile Cys Glu Gly Phe Thr Trp Ala
        115                 120                 125

Gly Val Thr Gln Asn Gly Glu Ser Gly Ala Cys Lys Arg Gly Pro Ala
    130                 135                 140

Asn Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
            180                 185                 190

Asn Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Gln Ser Gly Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Val
            260                 265                 270

Pro Ile Asp Thr Cys Val Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr
                325

<210> SEQ ID NO 51
<211> LENGTH: 221
<212> TYPE: PRT
<213> ORGANISM: Influenza A virus

<400> SEQUENCE: 51

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Arg Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
```

```
            115                 120                 125
Asn Ala Glu Asp Met Gly Asn Gly Cys Phe Lys Ile Tyr His Lys Cys
        130                 135                 140

Asp Asn Ala Cys Ile Glu Ser Ile Arg Asn Gly Thr Tyr Asp His Asp
145                 150                 155                 160

Ile Tyr Arg Asp Glu Ala Leu Asn Asn Arg Phe Gln Ile Lys Gly Val
                165                 170                 175

Glu Leu Lys Ser Ser Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
            195                 200                 205

Ala Cys Gln Arg Gly Asn Ile Arg Cys Asn Ile Cys Ile
            210                 215                 220

<210> SEQ ID NO 52
<211> LENGTH: 335
<212> TYPE: PRT
<213> ORGANISM: Influenza A virus

<400> SEQUENCE: 52

Leu Leu Cys Thr Phe Thr Ala Thr Tyr Ala Asp Thr Ile Cys Ile Gly
1               5                   10                  15

Tyr His Ala Asn Asn Ser Thr Asp Thr Val Asp Thr Val Leu Glu Lys
            20                  25                  30

Asn Val Thr Val Thr His Ser Val Asn Leu Leu Glu Asp Ser His Asn
        35                  40                  45

Gly Lys Leu Cys Leu Leu Lys Gly Ile Ala Pro Leu Gln Leu Gly Asn
    50                  55                  60

Cys Ser Val Ala Gly Trp Ile Leu Gly Asn Pro Glu Cys Glu Leu Leu
65                  70                  75                  80

Ile Ser Lys Glu Ser Trp Ser Tyr Ile Val Glu Thr Pro Asn Pro Glu
                85                  90                  95

Asn Gly Thr Cys Tyr Pro Gly Tyr Phe Ala Asp Tyr Glu Glu Leu Arg
            100                 105                 110

Glu Gln Leu Ser Ser Val Ser Ser Phe Glu Arg Phe Glu Ile Phe Pro
        115                 120                 125

Lys Glu Ser Ser Trp Pro Asn His Thr Val Thr Gly Val Ser Ala Ser
130                 135                 140

Cys Ser His Asn Gly Lys Ser Ser Phe Tyr Arg Asn Leu Leu Trp Leu
145                 150                 155                 160

Thr Gly Lys Asn Gly Leu Tyr Pro Asn Leu Ser Lys Ser Tyr Val Asn
                165                 170                 175

Asn Lys Glu Lys Glu Val Leu Val Leu Trp Gly Val His His Pro Pro
            180                 185                 190

Asn Ile Gly Asn Gln Arg Ala Leu Tyr His Thr Glu Asn Ala Tyr Val
        195                 200                 205

Ser Val Val Ser Ser His Tyr Ser Arg Arg Phe Thr Pro Glu Ile Ala
    210                 215                 220

Lys Arg Pro Lys Val Arg Asp Gln Glu Gly Arg Ile Asn Tyr Tyr Trp
225                 230                 235                 240

Thr Leu Leu Glu Pro Gly Asp Thr Ile Ile Phe Glu Ala Asn Gly Asn
                245                 250                 255

Leu Ile Ala Pro Trp Tyr Ala Phe Ala Leu Ser Arg Gly Phe Gly Ser
            260                 265                 270
```

Gly Ile Ile Thr Ser Asn Ala Pro Met Asp Glu Cys Asp Ala Lys Cys
            275                 280                 285

Gln Thr Pro Gln Gly Ala Ile Asn Ser Ser Leu Pro Phe Gln Asn Val
        290                 295                 300

His Pro Val Thr Ile Gly Glu Cys Pro Lys Tyr Val Arg Ser Ala Lys
305                 310                 315                 320

Leu Arg Met Val Thr Gly Leu Arg Asn Ile Pro Ser Ile Gln Ser
                325                 330                 335

<210> SEQ ID NO 53
<211> LENGTH: 222
<212> TYPE: PRT
<213> ORGANISM: Influenza A virus

<400> SEQUENCE: 53

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Lys Leu Glu Arg Arg Met Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asn Asn Glu Cys Met Glu Ser Val Lys Asn Gly Thr Tyr Asp Tyr Pro
145                 150                 155                 160

Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Leu Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 54
<211> LENGTH: 336
<212> TYPE: PRT
<213> ORGANISM: Influenza A virus

<400> SEQUENCE: 54

Leu Leu Tyr Th

Gly Lys Leu Cys Lys Leu Arg Gly Val Ala Pro Leu His Leu Gly Lys
50                  55                  60

Cys Asn Ile Ala Gly Trp Ile Leu Gly Asn Pro Glu Cys Glu Ser Leu
65                  70                  75                  80

Ser Thr Ala Ser Ser Trp Ser Tyr Ile Val Glu Thr Ser Ser Ser Asp
                85                  90                  95

Asn Gly Thr Cys Tyr Pro Gly Asp Phe Ile Asp Tyr Glu Glu Leu Arg
            100                 105                 110

Glu Gln Leu Ser Ser Val Ser Ser Phe Glu Arg Phe Glu Ile Phe Pro
        115                 120                 125

Lys Thr Ser Ser Trp Pro Asn His Asp Ser Asn Lys Gly Val Thr Ala
130                 135                 140

Ala Cys Pro His Ala Gly Ala Lys Ser Phe Tyr Lys Asn Leu Ile Trp
145                 150                 155                 160

Leu Val Lys Lys Gly Asn Ser Tyr Pro Lys Leu Ser Lys Ser Tyr Ile
                165                 170                 175

Asn Asp Lys Gly Lys Glu Val Leu Val Leu Trp Gly Ile His His Pro
            180                 185                 190

Ser Thr Ser Ala Asp Gln Gln Ser Leu Tyr Gln Asn Ala Asp Ala Tyr
        195                 200                 205

Val Phe Val Gly Thr Ser Arg Tyr Ser Lys Lys Phe Lys Pro Glu Ile
210                 215                 220

Ala Ile Arg Pro Lys Val Arg Asp Gln Glu Gly Arg Met Asn Tyr Tyr
225                 230                 235                 240

Trp Thr Leu Val Glu Pro Gly Asp Lys Ile Thr Phe Glu Ala Thr Gly
                245                 250                 255

Asn Leu Val Val Pro Arg Tyr Ala Phe Ala Met Glu Arg Asp Ala Gly
            260                 265                 270

Ser Gly Ile Ile Ile Ser Asp Thr Pro Val His Asp Cys Asn Thr Thr
        275                 280                 285

Cys Gln Thr Pro Lys Gly Ala Ile Asn Thr Ser Leu Pro Phe Gln Asn
    290                 295                 300

Ile His Pro Ile Thr Ile Gly Lys Cys Pro Lys Tyr Val Lys Ser Thr
305                 310                 315                 320

Lys Leu Arg Leu Ala Thr Gly Leu Arg Asn Val Pro Ser Ile Gln Ser
                325                 330                 335

<210> SEQ ID NO 55
<211> LENGTH: 222
<212> TYPE: PRT
<213> ORGANISM: Influenza A virus

<400> SEQUENCE: 55

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Leu Lys Ser Thr Gln Asn Ala Ile Asp Glu Ile
        35                  40                  45

Thr Asn Lys Val Asn Ser Val Ile Glu Lys Met Asn Thr Gln Phe Thr
    50                  55                  60

Ala Val Gly Lys Glu Phe Asn His Leu Glu Lys Arg Ile Glu Asn Leu
65                  70                  75                  80

Asn Lys Lys Ile Asp Asp Gly Phe Leu Asp Ile Trp Thr Tyr Asn Ala
                85                  90                  95

```
Glu Leu Leu Val Leu Leu Glu Asn Glu Arg Thr Leu Asp Tyr His Asp
                100                 105                 110

Ser Asn Val Lys Asn Leu Tyr Glu Lys Val Arg Ser Gln Leu Lys Asn
            115                 120                 125

Asn Ala Lys Glu Ile Gly Asn Gly Cys Phe Glu Phe Tyr His Lys Cys
        130                 135                 140

Asp Asn Thr Cys Met Glu Ser Val Lys Asn Gly Thr Tyr Asp Tyr Pro
145                 150                 155                 160

Lys Tyr Ser Glu Glu Ala Lys Leu Asn Arg Glu Glu Ile Asp Gly Val
                165                 170                 175

Lys Leu Glu Ser Thr Arg Ile Tyr Gln Ile Leu Ala Ile Tyr Ser Thr
            180                 185                 190

Val Ala Ser Ser Leu Val Leu Val Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 56
<211> LENGTH: 336
<212> TYPE: PRT
<213> ORGANISM: Influenza A virus

<400> SEQUENCE: 56

Leu Leu Cys Thr Phe Ala Ala Thr Asn Ala Asp Thr Leu Cys Ile Gly
1               5                   10                  15

Tyr His Ala Asn Asn Ser Thr Asp Thr Val Asp Thr Ile Leu Glu Lys
            20                  25                  30

Asn Val Thr Val Thr His Ser Val Asn Leu Leu Glu Asp Lys His Asn
        35                  40                  45

Gly Lys Leu Cys Lys Leu Gly Gly Ile Ala Pro Leu His Leu Gly Lys
    50                  55                  60

Cys Asn Ile Ala Gly Trp Leu Leu Gly Asn Pro Glu Cys Glu Leu Leu
65                  70                  75                  80

Phe Thr Val Ser Ser Trp Ser Tyr Ile Val Glu Thr Ser Asn Ser Asp
                85                  90                  95

Asn Gly Thr Cys Tyr Pro Gly Asp Phe Ile Asn Tyr Glu Glu Leu Arg
            100                 105                 110

Glu Gln Leu Ser Ser Val Ser Ser Phe Glu Arg Phe Glu Ile Phe Pro
        115                 120                 125

Lys Thr Ser Ser Trp Pro Asp His Glu Thr Asn Arg Gly Val Thr Ala
130                 135                 140

Ala Cys Pro Tyr Ala Gly Ala Asn Ser Phe Tyr Arg Asn Leu Ile Trp
145                 150                 155                 160

Leu Val Lys Lys Gly Asn Ser Tyr Pro Lys Leu Ser Lys Ser Tyr Val
                165                 170                 175

Asn Asn Lys Gly Lys Glu Val Leu Val Leu Trp Gly Ile His His Pro
            180                 185                 190

Pro Thr Ser Thr Asp Gln Gln Ser Leu Tyr Gln Asn Ala Asp Ala Tyr
        195                 200                 205

Ile Phe Val Gly Ser Ser Lys Tyr Asn Arg Lys Phe Lys Pro Glu Ile
    210                 215                 220

Ala Glu Arg Pro Lys Val Arg Gly Gln Ala Gly Arg Met Asn Tyr Tyr
225                 230                 235                 240

Trp Thr Leu Ile Glu Pro Gly Asp Thr Ile Lys Phe Glu Ala Thr Gly
```

```
                245                 250                 255

Asn Leu Val Val Pro Arg Tyr Ala Phe Ala Met Asn Arg Asp Pro Gly
            260                 265                 270

Ser Gly Ile Ile Thr Ser Asp Ala Pro Val His Asp Cys Asn Thr Thr
        275                 280                 285

Cys Gln Thr Pro Lys Gly Ala Ile Asn Thr Ser Leu Pro Phe Gln Asn
    290                 295                 300

Ile His Pro Val Thr Ile Gly Glu Cys Pro Lys Tyr Val Lys Ser Thr
305                 310                 315                 320

Lys Leu Arg Met Ala Thr Gly Leu Arg Asn Ile Pro Ser Ile Gln Ser
                325                 330                 335

<210> SEQ ID NO 57
<211> LENGTH: 222
<212> TYPE: PRT
<213> ORGANISM: Influenza A virus

<400> SEQUENCE: 57

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Val Asp Gly Ile
        35                  40                  45

Thr Asn Lys Val Asn Ser Val Ile Lys Lys Met Asn Thr Gln Phe Ala
    50                  55                  60

Ala Val Gly Lys Glu Phe Asn His Leu Glu Lys Arg Ile Glu Asn Leu
65                  70                  75                  80

Asn Lys Lys Val Asp Asp Gly Phe Leu Asp Val Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asn Leu Tyr Glu Lys Val Arg Ser Gln Leu Arg Asn
        115                 120                 125

Asn Ala Lys Glu Ile Gly Asn Gly Cys Phe Glu Phe Tyr His Lys Cys
    130                 135                 140

Asp Asp Thr Cys Met Glu Ser Val Lys Asn Gly Thr Tyr Asp Tyr Pro
145                 150                 155                 160

Arg Tyr Ser Glu Glu Ser Lys Leu Asn Arg Glu Glu Ile Asp Gly Val
                165                 170                 175

Lys Leu Glu Ser Thr Arg Ile Tyr Gln Ile Leu Ala Ile Tyr Ser Thr
            180                 185                 190

Ala Ala Ser Ser Leu Val Leu Leu Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 58
<211> LENGTH: 334
<212> TYPE: PRT
<213> ORGANISM: Influenza A virus

<400> SEQUENCE: 58

Leu Ile Leu Leu Phe Thr Ala Val Arg Gly Asp Gln Ile Cys Ile Gly
1               5                   10                  15

Tyr His Ala Asn Asn Ser Thr Glu Lys Val Asp Thr Asn Leu Glu Arg

```
            20                  25                  30
Asn Val Thr Val Thr His Ala Lys Asp Ile Leu Glu Lys Thr His Asn
         35                  40                  45

Gly Lys Leu Cys Lys Leu Asn Gly Ile Pro Pro Leu Glu Leu Gly Asp
 50                  55                  60

Cys Ser Ile Ala Gly Trp Leu Leu Gly Asn Pro Glu Cys Asp Arg Leu
 65                  70                  75                  80

Leu Ser Val Pro Glu Trp Ser Tyr Ile Met Glu Lys Glu Asn Pro Arg
                 85                  90                  95

Asp Gly Leu Cys Tyr Pro Gly Ser Phe Asn Asp Tyr Glu Glu Leu Lys
            100                 105                 110

His Leu Leu Ser Ser Val Lys His Phe Glu Lys Val Lys Ile Leu Pro
        115                 120                 125

Lys Asp Arg Trp Thr Gln His Thr Thr Thr Gly Gly Ser Arg Ala Cys
130                 135                 140

Ala Val Ser Gly Asn Pro Ser Phe Phe Arg Asn Met Val Trp Leu Thr
145                 150                 155                 160

Lys Glu Gly Ser Asp Tyr Pro Val Ala Lys Gly Ser Tyr Asn Asn Thr
                165                 170                 175

Ser Gly Glu Gln Met Leu Ile Ile Trp Gly Val His His Pro Ile Asp
            180                 185                 190

Glu Thr Glu Gln Arg Thr Leu Tyr Gln Asn Val Gly Thr Tyr Val Ser
        195                 200                 205

Val Gly Thr Ser Thr Leu Asn Lys Arg Ser Thr Pro Glu Ile Ala Thr
    210                 215                 220

Arg Pro Lys Val Asn Gly Gln Gly Gly Arg Met Glu Phe Ser Trp Thr
225                 230                 235                 240

Leu Leu Asp Met Trp Asp Thr Ile Asn Phe Glu Ser Thr Gly Asn Leu
                245                 250                 255

Ile Ala Pro Glu Tyr Gly Phe Lys Ile Ser Lys Arg Gly Ser Ser Gly
            260                 265                 270

Ile Met Lys Thr Glu Gly Thr Leu Glu Asn Cys Glu Thr Lys Cys Gln
        275                 280                 285

Thr Pro Leu Gly Ala Ile Asn Thr Thr Leu Pro Phe His Asn Val His
    290                 295                 300

Pro Leu Thr Ile Gly Glu Cys Pro Lys Tyr Val Lys Ser Glu Lys Leu
305                 310                 315                 320

Val Leu Ala Thr Gly Leu Arg Asn Val Pro Gln Ile Glu Ser
                325                 330

<210> SEQ ID NO 59
<211> LENGTH: 222
<212> TYPE: PRT
<213> ORGANISM: Influenza A virus

<400> SEQUENCE: 59

Gly Leu Phe Gly Ala Ile Ala Gly Phe Ile Glu Gly Gly Trp Gln Gly
 1               5                  10                  15

Met Val Asp Gly Trp Tyr Gly Tyr His His Ser Asn Asp Gln Gly Ser
            20                  25                  30

Gly Tyr Ala Ala Asp Lys Glu Ser Thr Gln Lys Ala Phe Asp Gly Ile
         35                  40                  45

Thr Asn Lys Val Asn Ser Val Ile Glu Lys Met Asn Thr Gln Phe Glu
 50                  55                  60
```

Ala Val Gly Lys Glu Phe Gly Asn Leu Glu Arg Leu Glu Asn Leu
65                  70                  75                  80

Asn Lys Arg Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Met Gln Leu Arg Asp
        115                 120                 125

Asn Val Lys Glu Leu Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Ser Met Gly Val Tyr Gln Ile Leu Ala Ile Tyr Ala Thr
            180                 185                 190

Val Ala Gly Ser Leu Ser Leu Ala Ile Met Met Ala Gly Ile Ser Phe
        195                 200                 205

Trp Met Cys Ser Asn Gly Ser Leu Gln Cys Arg Ile Cys Ile
    210                 215                 220

<210> SEQ ID NO 60
<211> LENGTH: 334
<212> TYPE: PRT
<213> ORGANISM: Influenza A virus

<400> SEQUENCE: 60

Leu Ile Leu Leu Leu Thr Val Val Lys Gly Asp Gln Ile Cys Ile Gly
1               5                   10                  15

Tyr His Ala Asn Asn Ser Thr Glu Thr Val Asp Thr Ile Leu Glu Arg
            20                  25                  30

Asn Val Thr Val Thr His Ala Lys Asn Ile Leu Glu Lys Thr His Asn
        35                  40                  45

Gly Lys Leu Cys Lys Leu Asn Gly Ile Pro Pro Leu Glu Leu Gly Asp
50                  55                  60

Cys Ser Ile Ala Gly Trp Leu Leu Gly Asn Pro Glu Cys Asp Arg Leu
65                  70                  75                  80

Leu Ser Ile Pro Glu Trp Ser Tyr Ile Met Glu Lys Glu Asn Pro Arg
                85                  90                  95

Asn Gly Leu Cys Tyr Pro Gly Ser Phe Asn Asp Tyr Glu Glu Leu Lys
            100                 105                 110

Leu Leu Leu Ser Ser Val Thr His Phe Glu Lys Val Lys Ile Leu Pro
        115                 120                 125

Arg Asp Arg Trp Thr Gln His Thr Thr Thr Gly Gly Ser Arg Ala Cys
    130                 135                 140

Ala Val Ser Gly Asn Pro Ser Phe Phe Arg Asn Met Val Trp Leu Thr
145                 150                 155                 160

Thr Lys Gly Ser Asn Tyr Pro Val Ala Lys Gly Ser Tyr Asn Asn Thr
                165                 170                 175

Asn Gly Glu Gln Ile Leu Ile Ile Trp Gly Val His His Pro Asn Asp
            180                 185                 190

Glu Thr Glu Gln Arg Thr Leu Tyr Gln Asn Val Gly Thr Tyr Val Ser
        195                 200                 205

Val Gly Thr Ser Thr Leu Asn Lys Arg Ser Ile Pro Glu Ile Ala Thr
    210                 215                 220

-continued

Arg Pro Lys Val Asn Gly Gln Gly Gly Arg Met Glu Phe Ser Trp Thr
225                 230                 235                 240

Leu Leu Asp Met Trp Asp Thr Ile Asn Phe Glu Ser Thr Gly Asn Leu
            245                 250                 255

Ile Ala Pro Glu Tyr Gly Phe Lys Ile Ser Arg Arg Gly Asn Ser Gly
        260                 265                 270

Ile Met Lys Thr Glu Gly Thr Leu Glu Asn Cys Glu Thr Lys Cys Gln
    275                 280                 285

Thr Pro Leu Gly Ala Ile Asn Thr Thr Leu Pro Phe His Asn Val His
290                 295                 300

Pro Leu Thr Ile Gly Glu Cys Pro Lys Tyr Val Lys Ser Glu Lys Leu
305                 310                 315                 320

Val Leu Ala Thr Gly Leu Arg Asn Ala His Lys Met Glu Ser
                325                 330

<210> SEQ ID NO 61
<211> LENGTH: 222
<212> TYPE: PRT
<213> ORGANISM: Influenza A virus

<400> SEQUENCE: 61

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Asp Gln Gly Ser
            20                  25                  30

Gly Tyr Ala Ala Asp Lys Glu Ser Thr Gln Lys Ala Val Asp Gly Ile
        35                  40                  45

Thr Asn Lys Val Asn Ser Val Ile Glu Lys Met Asn Thr Gln Phe Glu
    50                  55                  60

Ala Val Gly Lys Glu Phe Asn Asn Leu Glu Arg Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Met Gln Leu Arg Asp
        115                 120                 125

Asn Ala Lys Glu Ile Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Arg Leu Asn Arg Asn Glu Ile Lys Gly Val
                165                 170                 175

Lys Leu Ser Asn Met Gly Val Tyr Gln Ile Leu Ala Ile Tyr Ala Thr
            180                 185                 190

Val Ala Gly Ser Leu Ser Leu Ala Ile Met Met Ala Gly Ile Ser Phe
        195                 200                 205

Trp Met Cys Ser Asn Gly Ser Leu Gln Cys Arg Ile Cys Ile
    210                 215                 220

<210> SEQ ID NO 62
<211> LENGTH: 335
<212> TYPE: PRT
<213> ORGANISM: Influenza A virus

<400> SEQUENCE: 62

Leu Phe Ala Ile Val Ser Leu Val Lys Ser Asp Gln Ile Cys Ile Gly
1               5                   10                  15

Tyr His Ala Asn Asn Ser Thr Glu Gln Val Asp Thr Ile Met Glu Lys
            20                  25                  30

Asn Val Thr Val Thr His Ala Gln Asp Ile Leu Glu Lys Thr His Asn
        35                  40                  45

Gly Lys Leu Cys Ser Leu Asn Gly Val Lys Pro Leu Ile Leu Arg Asp
    50                  55                  60

Cys Ser Val Ala Gly Trp Leu Leu Gly Asn Pro Met Cys Asp Glu Phe
65                  70                  75                  80

Leu Asn Val Pro Glu Trp Ser Tyr Ile Val Glu Lys Asp Ser Pro Ile
                85                  90                  95

Asn Gly Leu Cys Tyr Pro Gly Asp Phe Asn Asp Tyr Glu Glu Leu Lys
            100                 105                 110

His Leu Leu Ser Ser Thr Asn His Phe Glu Lys Ile Gln Ile Ile Pro
        115                 120                 125

Arg Ser Ser Trp Ser Asp His Asp Ala Ser Ser Gly Val Ser Ser Ala
    130                 135                 140

Cys Pro Tyr Asn Gly Arg Ser Ser Phe Phe Arg Asn Val Val Trp Leu
145                 150                 155                 160

Ile Lys Lys Asn Asn Ala Tyr Pro Thr Ile Lys Arg Asn Tyr Asn Asn
                165                 170                 175

Thr Asn Gln Glu Asp Leu Leu Val Leu Trp Gly Ile His His Pro Asn
            180                 185                 190

Asp Ala Thr Glu Gln Thr Lys Leu Tyr Gln Asn Pro Thr Thr Tyr Val
        195                 200                 205

Ser Val Gly Thr Ser Thr Leu Asn Gln Arg Ser Val Pro Glu Ile Ala
    210                 215                 220

Thr Arg Pro Lys Val Asn Gly Gln Ser Gly Arg Ile Glu Phe Phe Trp
225                 230                 235                 240

Thr Ile Leu Lys Pro Asn Asp Ala Ile Asn Phe Glu Ser Asn Gly Asn
                245                 250                 255

Phe Ile Ala Pro Glu Tyr Ala Tyr Lys Ile Ala Lys Lys Gly Asp Ser
            260                 265                 270

Ala Ile Met Glu Ser Gly Leu Tyr Gly Asn Cys Asn Thr Lys Cys
        275                 280                 285

Gln Thr Pro Met Gly Ala Ile Asn Ser Ser Met Pro Phe His Asn Ile
    290                 295                 300

His Pro Leu Thr Ile Gly Glu Cys Pro Arg Tyr Val Lys Ser Asp Arg
305                 310                 315                 320

Leu Val Leu Ala Thr Gly Leu Arg Asn Val Pro Gln Arg Glu Thr
                325                 330                 335

<210> SEQ ID NO 63
<211> LENGTH: 222
<212> TYPE: PRT
<213> ORGANISM: Influenza A virus

<400> SEQUENCE: 63

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile

```
                35                  40                  45
Thr Asn Lys Val Asn Ser Ile Ile Asp Lys Met Asn Thr Gln Phe Glu
 50                  55                  60
Ala Val Gly Lys Glu Phe Asn Asn Leu Glu Arg Arg Ile Glu Asn Leu
65                  70                  75                  80
Asn Lys Lys Met Glu Asp Gly Phe Leu Asp Val Trp Thr Tyr Asn Ala
                85                  90                  95
Glu Leu Leu Val Leu Met Glu Asn Glu Arg Thr Leu Asp Phe His Asp
                100                 105                 110
Ser Asn Val Lys Asn Leu Tyr Asp Lys Val Arg Leu Gln Leu Arg Asp
                115                 120                 125
Asn Ala Lys Glu Leu Gly Asn Gly Cys Phe Glu Phe Tyr His Lys Cys
        130                 135                 140
Asp Asp Glu Cys Met Glu Ser Val Arg Asn Gly Thr Tyr Asp Tyr Pro
145                 150                 155                 160
Gln Tyr Ser Glu Glu Ala Arg Leu Asn Arg Glu Glu Ile Ser Gly Val
                165                 170                 175
Lys Leu Glu Ser Ile Gly Thr Tyr Gln Ile Leu Ser Ile Tyr Ser Thr
                180                 185                 190
Val Ala Ser Ser Leu Ala Leu Ala Ile Met Val Ala Gly Leu Ser Phe
        195                 200                 205
Trp Met Cys Ser Asn Gly Ser Leu Gln Cys Arg Ile Cys Ile
210                 215                 220

<210> SEQ ID NO 64
<211> LENGTH: 340
<212> TYPE: PRT
<213> ORGANISM: Influenza A virus

<400> SEQUENCE: 64

Leu Leu Phe Ala Ile Val Ser Leu Val Lys Ser Asp Gln Ile Cys Ile
1               5                   10                  15
Gly Tyr His Ala Asn Asn Ser Thr Glu Gln Val Asp Thr Ile Met Glu
                20                  25                  30
Lys Asn Val Thr Val Thr His Ala Gln Asp Ile Leu Glu Lys Thr His
                35                  40                  45
Asn Gly Lys Leu Cys Asp Leu Asp Gly Val Lys Pro Leu Ile Leu Arg
 50                  55                  60
Asp Cys Ser Val Ala Gly Trp Leu Leu Gly Asn Pro Met Cys Asp Glu
65                  70                  75                  80
Phe Ile Asn Val Pro Glu Trp Ser Tyr Ile Val Glu Lys Ala Asn Pro
                85                  90                  95
Val Asn Asp Leu Cys Tyr Pro Gly Asp Phe Asn Asp Tyr Glu Glu Leu
                100                 105                 110
Lys His Leu Leu Ser Arg Ile Asn His Phe Glu Lys Ile Gln Ile Ile
        115                 120                 125
Pro Lys Ser Ser Trp Ser Ser His Glu Ala Ser Leu Gly Val Ser Ser
        130                 135                 140
Ala Cys Pro Tyr Gln Gly Lys Ser Ser Phe Phe Arg Asn Val Val Trp
145                 150                 155                 160
Leu Ile Lys Lys Asn Ser Thr Tyr Pro Thr Ile Lys Arg Ser Tyr Asn
                165                 170                 175
Asn Thr Asn Gln Glu Asp Leu Leu Val Leu Trp Gly Ile His His Pro
                180                 185                 190
```

```
Lys Asp Ala Ala Glu Gln Thr Lys Leu Tyr Gln Asn Pro Thr Thr Tyr
            195                 200                 205

Ile Ser Val Gly Thr Ser Thr Leu Asn Gln Arg Leu Val Pro Arg Ile
210                 215                 220

Ala Thr Arg Ser Lys Val Asn Gly Gln Ser Gly Arg Met Glu Phe Phe
225                 230                 235                 240

Trp Thr Ile Leu Lys Pro Asn Asp Ala Ile Asn Phe Glu Ser Asn Gly
            245                 250                 255

Asn Phe Ile Ala Pro Glu Tyr Ala Tyr Lys Ile Val Lys Lys Gly Asp
            260                 265                 270

Ser Thr Ile Met Lys Ser Glu Leu Glu Tyr Gly Asn Cys Asn Thr Lys
            275                 280                 285

Cys Gln Thr Pro Met Gly Ala Ile Asn Ser Ser Met Pro Phe His Asn
            290                 295                 300

Ile His Pro Leu Thr Ile Gly Glu Cys Pro Lys Tyr Val Lys Ser Asn
305                 310                 315                 320

Arg Leu Val Leu Ala Thr Gly Leu Arg Asn Ser Pro Gln Arg Glu Arg
            325                 330                 335

Arg Arg Lys Lys
            340

<210> SEQ ID NO 65
<211> LENGTH: 222
<212> TYPE: PRT
<213> ORGANISM: Influenza A virus

<400> SEQUENCE: 65

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly

<210> SEQ ID NO 66
<211> LENGTH: 344
<212> TYPE: PRT
<213> ORGANISM: Influenza A virus

<400> SEQUENCE: 66

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Lys
            340

<210> SEQ ID NO 67
<211> LENGTH: 222
<212> TYPE: PRT

<213> ORGANISM: Influenza A virus

<400> SEQUENCE: 67

Gly Leu Phe Gly Ala Ile Ala Gly Phe Ile Gl

```
                130                 135                 140
Ser Gly Val Ser Ser Ala Cys Pro Tyr Leu Gly Ser Pro Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
                195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
                275                 280                 285

Asn Cys Asn Thr Lys Cys Gln Thr Pro Met Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys
                340                 345

<210> SEQ ID NO 69
<211> LENGTH: 223
<212> TYPE: PRT
<213> ORGANISM: Influenza A virus

<400> SEQUENCE: 69

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
                20                  25                  30

Gly Tyr Ala Ala Asp Lys Glu Ser Thr Gln Lys Ala Ile Asp Gly Val
            35                  40                  45

Thr Asn Lys Val Asn Ser Ile Ile Asp Lys Met Asn Thr Gln Phe Glu
50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
                100                 105                 110

Ser Asn Val Lys Asn Leu Tyr Asp Lys Val Arg Leu Gln Leu Arg Asp
                115                 120                 125

Asn Ala Lys Glu Leu Gly Asn Gly Cys Phe Glu Phe Tyr His Lys Cys
            130                 135                 140

Asp Asn Glu Cys Met Glu Ser Ile Arg Asn Gly Thr Tyr Asn Tyr Pro
145                 150                 155                 160
```

Gln Tyr Ser Glu Glu Ala Arg Leu Lys Arg Glu Ile Ser Gly Val
                165                 170                 175

Lys Leu Glu Ser Ile Gly Thr Tyr Gln Ile Leu Ser Ile Tyr Ser Thr
            180                 185                 190

Val Ala Ser Ser Leu Ala Leu Ala Ile Met Met Ala Gly Leu Ser Leu
        195                 200                 205

Trp Met Cys Ser Asn Gly Ser Leu Gln Cys Arg Ile Cys Ile Lys
    210                 215                 220

<210> SEQ ID NO 70
<211> LENGTH: 111
<212> TYPE: PRT
<213> ORGANISM: Homo sapiens

<400> SEQUENCE: 70

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Leu Tyr Asp Asp Asn Lys Arg Pro Ser Gly Val Ser Asp Arg Phe Ser
    50                  55                  60

Gly Ser Lys Ser Gly Ala Ser Ala Thr Leu Asp Ile Thr Gly Leu Gln
65                  70                  75                  80

Thr Gly Asp Glu Ala Asp Tyr Tyr Cys Gly Thr Trp Asp Asn Ile Leu
                85                  90                  95

Ser Val Val Leu Phe Gly Gly Gly Thr Arg Leu Thr Val Leu Ser
            100                 105                 110

<210> SEQ ID NO 71
<211> LENGTH: 396
<212> TYPE: DNA
<213> ORGANISM: Homo sapiens

<400> SEQUENCE: 71
caggtacagc tgcagcagtc aggggctgag gtgaagaagc ctgggtcctc ggtgaaggtc      60
tcctgcaagg cttctggagg caccttcaac aagtatgcta tcaactgggt gcgacaggcc     120
cctggaaaag gacttgagtg gatgggagga atcatccctt tcttcggaac aacaaactac     180
gcacagaagt tccagggcag agtcaccatt accgcggacg aaactacgag gacagcctac     240
atggagctga gcagcctgag atctgaggac acggccgtct attactgtgc gagaccttcg     300
attaatgaga gccctattg tttggactgc gcggccaaag actactacta cggtttggac     360
gtctggggcc aagggaccac ggtcaccgtc tcgagc                               396

<210> SEQ ID NO 72
<211> LENGTH: 300
<212> TYPE: DNA
<213> ORGANISM: Homo sapiens

<400> SEQUENCE: 72
caggtgcagc tggtgcagtc tggggctgag gtgaagaagc ctgggtcctc ggtgacggtc      60
tcctgcaagg cttctggagg cagcttcagt aagtatgcta tcaactgggt gcgacaggcc     120
cctggacaag gacttgagtg gatgggaggg atcatccctt tctttggtac aacaaactac     180
gcacagaagt tccaaggcag agtcacaatt accgcggacg catctacgag cacagcctac     240

```
atggcgctga gcagcctgag ctctgaggac acggccgtat actactgtgc gagaccttcg    300
```

<210> SEQ ID NO 73
<211> LENGTH: 396
<212> TYPE: DNA
<213> ORGANISM: Homo sapiens

<400> SEQUENCE: 73

```
caggtgcagc tggtgcagtc tggggctgag gtgaagaagc ctgggtcctc ggtgaaggtc     60
tcctgcaagg cttctggagg caccttcagc aagtatgcta tcaactgggt gcgccaggcc    120
cctggacaag gacttgagtg gatgggaggg atcatccctt tctttggtac aaccaactac    180
gcacagaagt tccagggcag actcacaatt accgcggacg catctacacg caccgcctac    240
atggagctga gcagcctgag atctgaagac acggccgtct attactgtgc gagaccttcg    300
attactgaga cccagtattg tttggactgc gcggccaaag actattacta cggtttggac    360
gtctggggcc aagggaccac ggtcaccgtc tcgagc                               396
```

<210> SEQ ID NO 74
<211> LENGTH: 396
<212> TYPE: DNA
<213> ORGANISM: Homo sapiens

<400> SEQUENCE: 74

```
caggtgcagc tggtgcagtc tggggctgag gtgaagaagc ctgggtcctc ggtgaaggtc     60
tcctgcaagg cttctggagg caccttcagc aagtatgcta tcaactgggt gcgccaggcc    120
cctgcacaag gacttgagtg gatgggaggg atcatccctt tctttggtac aaccaactac    180
gcacagaagt tccagggcag actcacgatt accgcggacg catctacacg cacagcctac    240
atggagctga gcagcctgag atctgaggac acggccgtct attactgtgc gagaccttcg    300
attactgaga gccagtattg tttggactgc gcggccaaag actactacta cggtttagat    360
gtctggggcc aagggaccac ggtcaccgtc tcgagc                               396
```

<210> SEQ ID NO 75
<211> LENGTH: 396
<212> TYPE: DNA
<213> ORGANISM: Homo sapiens

<400> SEQUENCE: 75

```
gaggtgcagc tggtggagtc tggggctgag gtgaagaagc ctgggtcctc ggtgaaggtc     60
tcctgcaagg cttctggagg caccttcagc aagtatgcta tcaactgggt gcgccaggcc    120
cctggacaag gacttgagtg gatgggaggg atcatccctt tcttcggtac aaccaactac    180
gcacagaagt tccagggcag actcacaatt accgcggacg catctacacg cacagcctac    240
atggagctga gcagcctgag atctgaggac acggccgtct attactgtgc gagaccttcg    300
attactgaga gtcagtattg tctggactgc gcggccaaag actactacta cggtttagat    360
gtctggggcc aagggacaat ggtcaccgtc tcgagc                               396
```

<210> SEQ ID NO 76
<211> LENGTH: 393
<212> TYPE: DNA
<213> ORGANISM: Homo sapiens

<400> SEQUENCE: 76

```
gaggtgcagc tggtggagtc tggggctgag gtgaagaagc ctgggtcctc ggtgaaggtc     60
tcctgcaggg cttctggaac cttctacaag tatgcaatca actgggtgcg acaggcccct    120
```

| | |
|---|---|
| ggacaagggc ttgagtggat gggagggatc atcccttcct ttggtacaac aaactacgca | 180 |
| cagaaattcc agggcagact cactattacc gcggacggat ctacgaacac cgcctacatg | 240 |
| cagctggaca gcctgagatc tgaagacacg gccgtgtatt attgtgcggg accttcgatt | 300 |
| actgagagcc actattgttt ggactgcgcg gccaaagatt actactacgg tttggacgtc | 360 |
| tggggccaag ggaccacggt caccgtctcg agc | 393 |

<210> SEQ ID NO 77
<211> LENGTH: 333
<212> TYPE: DNA
<213> ORGANISM: Homo sapiens

<400> SEQUENCE: 77

| | |
|---|---|
| cagtctgtgt tgacgcagcc gccctcagcg tctgggaccc ccgggcagag ggtcaccatc | 60 |
| tcttgttctg gaagcagctc caacatcgga agtaattttg tatactggta ccagcagctc | 120 |
| ccaggaacgg cccccaaact cctcatctat aggaataatc agcggccctc aggggtccct | 180 |
| gaccgattct ctggctccag gtctggcacc tcagcctccc tggccatcag tgggctccgg | 240 |
| tccgaggatg aggctgatta ttactgtgca gcatgggatg acagcctgag tggtgctgtg | 300 |
| ttcggaggag gcacccagct gaccgtcctc ggt | 333 |

<210> SEQ ID NO 78
<211> LENGTH: 333
<212> TYPE: DNA
<213> ORGANISM: Homo sapiens

<400> SEQUENCE: 78

| | |
|---|---|
| cagtctgtgt tgacgcagcc gccctcagtg tctgcggccc caggacagaa ggtcaccatc | 60 |
| tcctgctctg gaagcagctc caacattggg aataattatg tatcctggta ccagcagctc | 120 |
| ccaggaacag cccccaaact cctcatttat gacaataata gcgaccctc agggattcct | 180 |
| gaccgattct ctggctccaa gtctggcacg tcagccaccc tgggcatcac cggactccag | 240 |
| actggggacg aggccgatta ttactgcgga acatgggata gcagcctgag tgctggggta | 300 |
| ttcggcggag ggaccaagct gaccgtccta ggt | 333 |

<210> SEQ ID NO 79
<211> LENGTH: 333
<212> TYPE: DNA
<213> ORGANISM: Homo sapiens

<400> SEQUENCE: 79

| | |
|---|---|
| cagtctgtgt tgacgcagcc gccctcagtg tctgcggccc caggacagaa ggtcaccatc | 60 |
| tcctgctctg gaagcacctc caacattggg gataattatg tatcctggta ccagcaggtc | 120 |
| ccaggaacag cccccaaact cctcatttat gacaataatc agcgaccctc agggattcct | 180 |
| gaccgattct ctggctccaa gtctggcacg tcagccaccc tgggcatcac cggactccag | 240 |
| actggggacg aggccgatta ttactgcgga acatgggata gcagcctgag tgctgtccta | 300 |
| ttcggcgggg ggaccaaact gaccgtccta cgt | 333 |

<210> SEQ ID NO 80
<211> LENGTH: 333
<212> TYPE: DNA
<213> ORGANISM: Homo sapiens

<400> SEQUENCE: 80

| | |
|---|---|
| cagtctgtgt tgacgcagcc gccctcagcg tctgggaccc ccgggcagag ggtcaccatc | 60 |
| tcttgttctg gaggcacctc caacatcgga agtaatactg taaactggta ccagcaactc | 120 |
| ccaggaacgg cccccaaact cctcatgtat agtaataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtgtggta | 300 |
| ttcggcggag ggaccaagct gaccgtccta ggt | 333 |

<210> SEQ ID NO 81
<211> LENGTH: 333
<212> TYPE: DNA
<213> ORGANISM: Homo sapiens

<400> SEQUENCE: 81

| | |
|---|---|
| cagtctgtgt tgacgcagcc gccctcagcg tctgggaccc ccgggcagag ggtcaccatc | 60 |
| tcttgttctg gaagcagctc caacatcgga agtaatactg taaactggta ccagcagctc | 120 |
| ccaggaacgg cccccaaact cctcatctat agtaataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtgtggta | 300 |
| ttcggcggag ggaccaagct gaccgtccta ggt | 333 |

<210> SEQ ID NO 82
<211> LENGTH: 336
<212> TYPE: DNA
<213> ORGANISM: Homo sapiens

<400> SEQUENCE: 82

| | |
|---|---|
| cagtctgtgt tgacgcagcc gccctcagcg tctgggaccc ccgggcagag ggtcaccatc | 60 |
| tcttgttctg gaagcagctc caacatcgga agtaatactg taaactggta ccagcagctc | 120 |
| ccaggaacgg cccccaaact cctcatctat agtaataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtcatgct | 300 |
| gtgttcggag gaggcaccca gctgaccgtc ctcggt | 336 |

<210> SEQ ID NO 83
<211> LENGTH: 333
<212> TYPE: DNA
<213> ORGANISM: Homo sapiens

<400> SEQUENCE: 83

| | |
|---|---|
| cagtctgtgt tgacgcagcc gccctcagcg tctgggaccc ccgggcagag ggtcaccatc | 60 |
| tcttgttctg gaggcacctc caacatcgga agtaatactg taaactggta ccagcaactc | 120 |
| ccaggaacgg cccccaaact cctcatgtat aataataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtgtggta | 300 |
| ttcggcggag ggaccaagct gaccgtccta ggt | 333 |

<210> SEQ ID NO 84
<211> LENGTH: 333
<212> TYPE: DNA
<213> ORGANISM: Homo sapiens

<400> SEQUENCE: 84

```
cagtctgtgt tgacgcagcc gccctcagcg tctgggaccc ccgggcagag ggtcaccatc        60
tcttgttctg gaagcagctc caacatcgga agtaatactg taaactggta ccagcagctc       120
ccaggaacgg ccccccaaact cctcatctat agtaataatc agcggccctc aggggcccct      180
gaccgattct ctggctccaa gtctggcacc tcagcctccc tggccatcag tgggctccag       240
tctgaggatg aggctgatta ttactgtgca gcatgggatg acagcctgaa tggttatgtc       300
ttcggaactg ggaccaaggt caccgtccta ggt                                   333
```

<210> SEQ ID NO 85
<211> LENGTH: 333
<212> TYPE: DNA
<213> ORGANISM: Homo sapiens

<400> SEQUENCE: 85

```
cagtctgtgt tgacgcagcc gccctcagtg tctgcggccc caggacagaa ggtcaccatc        60
tcctgctctg gaagcagctc caacattggg aataatgatg tctcatggta ccagcagctc       120
ccaggaacag ccccccaaact cctcctttat gacgataata agcgaccctc aggggtttct      180
gaccgattct ctggctccaa gtctggcgcg tcagccaccc tggacatcac cggactccag       240
actggggacg aggccgatta ttactgcggg acatgggata acatcctgag tgttgtgtta       300
ttcggcggag ggaccaggct gaccgtccta agt                                   333
```

<210> SEQ ID NO 86
<211> LENGTH: 333
<212> TYPE: DNA
<213> ORGANISM: Homo sapiens

<400> SEQUENCE: 86

```
cagtctgtgt tgacgcagcc gccctcagcg tctgggaccc ccgggcagag ggtcaccatc        60
tcttgttctg gaagcaactc caacatcgga agtaatactg taaactggta ccagcagctc       120
ccaggaacgg ccccccaaact cctcatctat actaataatc agcggccctc aggggtccct     180
gaccgattct ctggctccaa gtctggcacc tcagcctccc tggccatcag tgggctccag       240
tctgaggatg aggctgatta ttactgtgca tcatgggatg acagcctgaa tggtgtggta       300
ttcggcggag ggaccaagct gaccgtccta ggt                                   333
```

<210> SEQ ID NO 87
<211> LENGTH: 333
<212> TYPE: DNA
<213> ORGANISM: Homo sapiens

<400> SEQUENCE: 87

```
cagtctgtgt tgacgcagcc gccctcagcg tctgggaccc ccgggcagag cgtcaccatc        60
tcttgttctg gaagcaggtc caacatcgga ggtaatactg taaactggta ccagcacctc       120
ccaggtatgg ccccccaaact cctcatctat agtagtaatc agcggtcctc aggggtccct      180
gaccgattct ctggctccaa gtctggcacc tcagcctccc tggccattag tgggctccag       240
tctgaggatg acgctgatta ttactgtgcc tcatgggatg acagcctgaa tggtgtggtg       300
ttcggcggag ggaccaagct gaccgtccta ggt                                   333
```

<210> SEQ ID NO 88
<211> LENGTH: 333
<212> TYPE: DNA
<213> ORGANISM: Homo sapiens -continued

```
<400> SEQUENCE: 88
cagtctgtgt tgacgcagcc gccctcagtg tctgcggccc caggacagaa ggtcaccatc      60
tcctgctctg gaagcagctc caacattggg aataatgatg tctcatggta ccagcagctc     120
ccaggaacag cccccaaact cctcctttat gacgataata agcgaccctc aggggtttct     180
gaccgattct ctggctccaa gtctggcgcg tcagccaccc tggacatcac cggactccag     240
actggggacg aggccgatta ttactgcggg acatgggata acatcctgag tgttgtgtta     300
ttcggcggag ggaccaggct gaccgtccta agt                                  333
```

INFLUENZA VIRUS-NEUTRALIZING ANTIBODY AND SCREENING METHOD THEREFOR

TECHNICAL FIELD OF THE INVENTION

The present invention relates to an anti-influenza virus antibody that exhibits ubiquitous neutralizing activity against all influenza viruses beyond the barrier of subtypes, a method of producing the same, and a method of detecting the antibody in a subject.

BACKGROUND OF THE INVENTION

The influenza virus is an RNA envelop virus having a particle size of about 100 nm in diameter belonging to the family Orthomyxoviridae. It occurs in three types classified according to the antigenicity of internal protein thereof: types A, B and C. The influenza virus consists of an internal nucleocapsid surrounded by a viral envelop having a lipid bilayer structure or a ribonucleic acid (RNA) core associated with nuclear protein and an external glycoprotein. The inner layer of the viral envelop is configured mainly by matrix protein, whereas the outer layer is mostly configured by a host-derived lipid substance. The RNA of influenza virus assumes a segmentary structure. The influenza that spreads widely all over the world is caused by type A influenza viruses. Type A viruses have two kinds of envelop glycoproteins, i.e., hemagglutinin (HA) and neuraminidase (NA). According to antigenicity variation, HA is classified into 16 subtypes, and NA into 9 subtypes.

In recent years, highly pathogenic H5N1 avian influenza virus has been rampant worldwide; it could even be said that a new viral strain that can be communicated from one person to another could emerge and cause a pandemic at any moment. To cope with this situation, a global viral testing system is being enhanced, and large stockpiling of Tamiflu and the like as therapeutic drugs, vaccine development, production, and stockpiling are being implemented. However, the situation stands while many issues remain to be clarified, including when and how it will emerge, whether Tamiflu and the like will be therapeutically effective in the event thereof, whether the vaccine developed will be effective, when and to whom it will be inoculated, and, more importantly, when to institute a state of high alert, and when to call off it. This is because we are going to encounter a situation that has never been experienced by human being, where vaccines and therapeutic drugs for pathogens and viruses that have not yet emerged must be stockpiled. A problem with vaccine development, in particular, resides in the fact that every year many mutations occur in the hemagglutinin gene on the influenza virus genome to cause an antigenic drift (change in antigenicity), which is thought to be the cause of epidemic prevalence. Therefore, inoculating a vaccine that does not match the prevailing subtype does not have an expected prophylactic effect. The reason why no attempts have been made to develop antibody therapeutic drugs (prophylactic drugs) for influenza virus is that it is feared that a medicine that has been developed with considerable effort is no longer useful because the virus that should otherwise be neutralized at the time of development has changed its nature due to an antigenic drift.

The present inventors screened a phage display human antibody library generated from a large number of B lymphocytes collected from one individual for twelve influenza virus strains of subtype H3N2 separated between 1968 and 2004, and found that the majority of clones exhibiting neutralizing activity were anti-hemagglutinin antibodies, and that they were roughly dividable into three groups: those that specifically neutralize viral strains separated in 1968-1973, viral strains separated in 1977-1993, and viral strains separated in 1997-2003 (non-patent document 1). Although this finding upsets the conventional common notion that it is meaningless to develop antibody therapeutic drugs (prophylactic drug) for influenza virus, phage antibody libraries have not been seriously investigated to date since combinations of a heavy chain and a light chain do not always reflect the in vitro environment and for other reasons.

Against this background, three research groups independently succeeded in isolating human monoclonal antibodies that neutralize subtype H5 influenza viruses (patent documents 1 and 2, non-patent documents 2-4). These antibodies were shown to exhibit neutralizing activity not only on subtype H5 influenza viruses, but also on other subtypes (e.g., subtype H1 and the like). However, while the 16 subtypes of hemagglutinin (H1-H16) are classified according to epitope into two major groups (Groups 1 and 2), these antibodies exhibited neutralizing activity only against Group 1 (e.g., subtypes H1, H2, H5, H6, H8, H9 and the like), and did not exhibit neutralizing activity on subtypes of influenza virus belonging to Group 2 (e.g., subtypes H3 and H7 and the like). That is, no anti-influenza virus antibody that exhibits a broad range of neutralizing activity beyond the barrier of the two groups based on the sequence of hemagglutinin has been isolated or reported.

X-ray structural analysis has revealed the binding modes of these antibodies and hemagglutinin, making it evident that the 38-position amino acid of hemagglutinin has changed to asparagine in subtypes H3 and H7 in Group 2 and undergoes N-type sugar chain modification (non-patent documents 4 and 5). Furthermore, it has been reported that introducing an N-type sugar chain modification site into the 38-position of H5 caused the binding ability of the neutralizing antibody to decrease by 70% (non-patent document 5). It is also known that when an influenza virus having its hemagglutinin mutated escapes a neutralizing antibody, such mutations accumulate mainly in five regions within the hemagglutinin gene (A, B, C, D and E regions), which reportedly comprises a neutralizing epitope (non-patent documents 6 and 7). These findings suggest difficulty in acquiring a neutralizing antibody that acts beyond this barrier between the two groups.

PRIOR ART DOCUMENTS

Patent Documents

[patent document 1] WO 2007/134327
[patent document 2] WO 2008/028946

Non-Patent Documents

[non-patent document 1] Virology Vol. 397, pp. 322-330, 2010
[non-patent document 2] Proc. Natl. Acad. Sci. USA., Vol. 105, pp. 5986-5991, 2008
[non-patent document 3] PLoS ONE, Vol. 3, pp. 5986-5991, e3942, 2008
[non-patent document 4] Nature Structural & Molecular Biology, Vol. 16, pp. 265-273, 2009
[non-patent document 5] Science, Vol. 324, pp. 246-251, 2009
[non-patent document 6] Nature, Vol. 289, pp. 373-378, 1981

[non-patent document 7] J. Gen. Virol., Vol. 62, pp. 153-169, 1982

SUMMARY OF THE INVENTION

Problems to be Solved by the Invention

In preparation for a pandemic with subtype H5N1 influenza expected to occur in the near future and subsequent pandemics with subtype H7 and H9 viruses that are likely to occur, there is a high demand for the development of a prophylactic approach based on a new concept that is more comprehensive and more reliable than the conventional concept of influenza prophylaxis that vaccines are designed on the basis of predicted changes in antigenicity.

Accordingly, it is an object of the present invention to provide an anti-influenza virus antibody that exhibits neutralizing activity beyond the barrier between the two groups based on the conservativeness of the amino acid sequence of hemagglutinin protein, desirably an antibody that exhibits neutralizing activity on all subtypes, i.e., H1 to H16, of influenza virus, and a method of producing the same. Another object of the present invention is to provide a testing method enabling to determine whether the subject carries the above-described universal neutralizing antibody conveniently and relatively inexpensively.

Means of Solving the Problems

The present inventors collected a large number, $10^9$, of B lymphocytes from one individual using apheresis (separated collection of one particular component of blood), generated a phage display human antibody library reflecting almost all antibody repertoires, and comprehensively screened for antibody clones that bind to inactivated H3N2 influenza virus by the panning method using the virus as the antigen. Antibodies were recovered from the selected phage and tested for neutralizing activities on subtype H3 influenza viruses, which belong to Group 2, and on subtype H1, subtype H2 and subtype H5 influenza viruses, which belong to Group 1. As a result, the inventors surprisingly succeeded in acquiring more than 40 clones of antibodies that exhibit neutralizing activity not only on subtype H3, which was used as the antigen for screening, but also on subtype H1, subtype H2 and subtype H5 influenza viruses, which belong to a group different from the group to which H3 subtype belongs. These clones were found to have six different heavy-chain variable domain (VH) amino acid sequences, all of which were subjected to IgBLAST search, leading to the judgement that the germline is VH1-69 for all of them. IgBLAST search revealed that the light-chain variable domains (VL) present in these six clones were confined to three different germlines.

Since a previously reported neutralizing antibody against subtype H5 utilizes VH1-69 or similar VH1-e, and taking into account the binding mode of the neutralizing antibody and hemagglutinin, revealed by X-ray structural analysis, it is an unexpected finding that the antibody acquired by the present inventors is capable of neutralizing subtype H3 influenza viruses. However, the present inventors idealized that by extensively screening antibodies that react with a certain subtype as the antigen in the search for an antibody that neutralizes a virus of a subtype in a group different from the group to which the antigen belongs, an antibody capable of neutralizing all subtypes of influenza virus beyond the barrier between the groups could be acquired. Hence, the present inventors collected $10^9$ B lymphocytes, a number larger by two digits than in conventional cases, from one individual, generated a human antibody library that almost completely reflects the donor's antibody repertoire, comprehensively screened for antibody clones that bind to subtype H3 influenza viruses, and examined their neutralizing activities on subtype H1, subtype H2 and subtype H5 influenza viruses, thus succeeding for the first time in isolating antibodies capable of neutralizing influenza viruses of both Group 1 and Group 2.

Analyzing the amino acid sequences of the neutralizing antibodies obtained revealed that all the neutralizing antibodies utilize the VH1-69 gene as the heavy-chain variable domain V region. Noticeably, clones that exhibited higher neutralizing activity against influenza viruses of Group 1 than other clones were found to have a deletion of one amino acid in the heavy-chain variable domain V region. Because the process in which antibody-producing cells transform upon growth and differentiation stimulation (antibody maturation) occurs as one strand of the DNA double strand encoding the heavy chain and light chain undergoes cleavage, and a mutation is induced in the process of repairing the cleavage by DNA polymerase, which frequently causes errors, the resulting mutations are mostly amino acid substitutions based on single-base substitutions. Therefore, the frequency of deletion of one amino acid (3 bases) is extremely low; even if such a deletion occurs, it mostly has a bad influence, which in turn further reduces the probability that a mechanism works wherein B cells producing the antibody are stimulated to remain long as memory cells in the body. Taking into account this technical common sense, it is surprising that the antibody that neutralized influenza viruses mainly of Group 2 have acquired rather potent neutralizing activity against influenza viruses belonging to Group 1 as a result of deletion of one amino acid in a heavy-chain variable domain other than CDR3.

The present inventors conducted further investigations based on these findings, and have developed the present invention.

Accordingly, the present invention provides:

[1] an isolated antibody that neutralizes both at least one influenza virus selected from Group 1 consisting of subtype H1, subtype H2, subtype H5, subtype H6, subtype H8, subtype H9, subtype H11, subtype H12, subtype H13 and subtype H16 influenza viruses and at least one influenza virus selected from Group 2 consisting of subtype H3, subtype H4, subtype H7, subtype H10, subtype H14 and subtype H15 influenza viruses;

[2] the antibody according to [1] above, wherein the antibody neutralizes both at least subtype H1 and/or subtype H5 influenza virus and subtype H3 influenza virus;

[3] the antibody according to [1] above, wherein the antibody neutralizes subtype H1 to subtype H16 influenza viruses;

[4] the antibody according to [1] above, wherein the heavy-chain variable domain V region utilizes the VH1-69 or VH1-e gene;

[5] the antibody according to [4] above, wherein the heavy-chain variable domain V region has an amino acid deletion;

[6] the antibody according to [5] above, wherein the heavy-chain variable domain V region encoded by the VH1-69 or VH1-e gene has at least a mutation for deleting the 27th glycine;

[7] the antibody according to [1] above, wherein the light-chain variable domain V region utilizes the VL1-44, VL1-47 or VL1-51 gene;

[8] the antibody according to [1] above, wherein the minimum inhibitory concentration in focus formation inhibition test when the antibody is converted to type IgG is on the order of $10^{-11}$-$10^{-12}$ M;
[9] the antibody according to [1] above, wherein the antibody is a human antibody;
[10] the antibody according to [1] above, wherein the complementarity determining region 1 of the heavy-chain variable domain consists of the amino acid sequence shown by SEQ ID NO:1, and the complementarity determining region 2 consists of the amino acid sequence shown by SEQ ID NO:2;
[11] the antibody according to [10] above, wherein the framework region 1 of the heavy-chain variable domain consists of the amino acid sequence shown by SEQ ID NO:3;
[12] the antibody according to [1] above, wherein the heavy-chain variable domain V region consists of the amino acid sequence shown by any one of SEQ ID NOs:4-9;
[13] the antibody according to [1] above, wherein the heavy-chain variable domain consists of the amino acid sequence shown by any one of SEQ ID NOs:10-15;
[14] the antibody according to [1] above, wherein the heavy-chain variable domain and the light-chain variable domain consist of the amino acid sequences shown by one of the following combinations (a)-(l), respectively:
(a) SEQ ID NO:10 and SEQ ID NO:16;
(b) SEQ ID NO:10 and SEQ ID NO:17;
(c) SEQ ID NO:10 and SEQ ID NO:18;
(d) SEQ ID NO:10 and SEQ ID NO:19;
(e) SEQ ID NO:10 and SEQ ID NO:20;
(f) SEQ ID NO:10 and SEQ ID NO:21;
(g) SEQ ID NO:10 and SEQ ID NO:22;
(h) SEQ ID NO:11 and SEQ ID NO:23;
(i) SEQ ID NO:13 and SEQ ID NO:24;
(j) SEQ ID NO:14 and SEQ ID NO:25;
(k) SEQ ID NO:15 and SEQ ID NO:26; and
(l) SEQ ID NO:12 and SEQ ID NO:70,
[15] a passive immunotherapeutic agent for influenza comprising the antibody according to [1] above;
[16] a method of passive immunotherapy for influenza comprising administering an effective amount of the antibody according to [1] above to a mammalian or avian subject that has been infected, or can get infected, with influenza virus;
[17] the method according to [16] above, wherein the subject receiving the administration is a human;
[18] a method of producing the antibody according to [1] above, comprising the steps of:
(1) providing an antibody library comprising antibody clones derived from more than about $10^8$ B cells collected from one individual,
(2) contacting an influenza virus of any one of subtypes H1 to H16 or the hemagglutinin protein of the virus or an extracellular domain thereof as the antigen with the antibody library (1), and comprehensively selecting antibody clones that react with the antigen,
(3) recovering an antibody molecule from each antibody clone selected in the step (2),
(4) testing each antibody obtained in the step (3) for neutralizing activity on both at least one influenza virus selected from Group 1 and at least one influenza virus selected from Group 2, and
(5) producing an antibody that has neutralized both an influenza virus belonging to Group 1 and an influenza virus belonging to Group 2 using a clone that produces the antibody, and recovering the antibody;
[19] the method according to [18] above, wherein the antibody is a human antibody;
[20] the method according to [18] above, wherein the antibody library is a phage display library;
[21] the method according to [20] above, wherein the number of antibody clones is $10^{10}$ to $10^{11}$;
[22] the method according to [18] above, wherein the B cells are collected by apheresis;
[23] the method according to [18] above, wherein the method comprises using an influenza virus isolate with which the individual from which the B cells have been collected in the step (2) above has not been infected or the hemagglutinin protein thereof or an extracellular domain thereof as the antigen;
[24] the method according to [23] above, wherein the influenza virus isolate is of subtype H1, H2 or H3;
[25] the method according to [23] above, wherein the influenza virus isolate is of a hemagglutinin subtype with which the individual from which the B cells have been collected has not been infected;
[26] the method according to [25] above, wherein the influenza virus isolate is of subtype H5, H7 or H9;
[27] the method according to [18] above, comprising testing neutralizing activity on both at least subtype H1 and/or subtype H5 influenza virus and subtype H3 influenza virus in the step (4) above;
[28] the method according to [20] above, further comprising the step of converting the antibody to type IgG;
[29] a method of detecting the antibody according to [1] above in a subject, comprising the steps of:
(1) inoculating hemagglutinin of the subtype of any one of subtypes H1 to H16 to the subject,
(2) collecting blood from the subject at the time when antibody-producing cells have been sufficiently proliferated after inoculation, and
(3) examining the blood for the presence or absence of antibody-producing cells that present an antibody that binds to both hemagglutinin of a subtype selected from Group 1 and hemagglutinin of a subtype selected from Group 2, and that has the heavy-chain variable domain V region encoded by the VH1-69 or VH1-e gene;
[30] a method of detecting the antibody according to [1] above in a subject, comprising the steps of:
(1) inoculating hemagglutinin of a subtype selected from Group 1 and hemagglutinin of a subtype selected from Group 2 separately to the subject,
(2) collecting blood from the subject at the time when antibody-producing cells have been sufficiently proliferated after inoculation of each hemagglutinin, and
(3) examining the blood for the presence or absence of antibody-producing cells that present an antibody that binds to hemagglutinin of a subtype selected from a group different from the group to which the inoculated hemagglutinin belongs, and that has the heavy-chain variable domain V region encoded by the VH1-69 or VH1-e gene, and the like.

Effect of the Invention

According to the present invention, a human antibody possessing neutralizing activity against all hemagglutinin subtypes of influenza viruses can be provided. Passive immunization with the neutralizing antibody enables to effectively prevent or treat influenza even in the event of an antigenic shift, as well as an antigenic drift. The present invention also makes it possible to determine whether the subject has memory B cells that produce an antibody that exhibits neutralizing activity on influenza viruses beyond the barrier of the groups.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1-1 and 1-2 show the results of an ELISA determination of the binding activities of the antibodies screened for from a phage display human antibody library for all 12 different H3N2 virus strains and one H1N1 virus strain.

FIG. 2 shows which subtype H3 influenza virus strains were used as the antigens in screening for clones classified under Group.11 and Group 22.

FIG. 3 shows the influenza virus strains used for screening for respective antibody clones classified under Group.11 and the number of clones isolated.

FIG. 4 shows the amino acid sequences of the VH and VL of clones classified under Group.11, wherein the dot (.) shown in the FR1 region of FR045-092 indicates a deleted amino acid.

FIG. 5 shows the results of a comparison of the amino acids of the heavy-chain variable domains of clones classified under Group.11 and antibodies reported to exhibit neutralizing activity against both H1 strains and H5 strains, wherein the dot (.) shown in the FR1 region of FR045-092 indicates a deleted amino acid.

FIG. 8 shows the results of an investigation of the hemagglutination inhibiting activities of clones classified under Group.11 against subtype H3 and subtype H1 influenza viruses.

FIG. 9 shows the results of an investigation of the focus formation inhibiting activities of clones classified under Group.11 against subtype H3 and subtype H1 influenza viruses.

FIG. 10 shows the results of an ELISA determination of whether clones classified under Group.11 competitively inhibit the binding activity of the mouse monoclonal antibody C179 for subtype H3 influenza virus. ELISA was performed on the influenza A/USSR New Caledonia strain of C179 in the presence and absence (No Fab-p3) of Fab-p3 antibodies (F022-360, F026-146, F026-427, F045-092, F005-126), wherein F005-126 served as a negative control that did not react to the influenza A/USSR New Caledonia strain HA.

FIGS. 15-1 and 15-2 are graphic representations of the reactivities of Fab clones to the influenza virus A/H3N2 Aichi strains HA0 and HAL wherein grey peaks indicate the results of Mock-transfection, green peaks indicate the results of pDisp-Aic68HA0 transfection, pink peaks indicate the results of pDisp-Aic68HA1 transfection, blue peaks indicate the results of pDisp-Fuk85HA0 transfection, and orange peaks indicate the results of pDisp-Fuk85HA1 transfection.

FIGS. 17-1 and 17-2 show the amino acid sequences of HA1 and HA2 for each subtype and strain of influenza virus.

FIG. 18 shows the results of a FACS analysis of the bindabilities of various HA antibodies for cells expressing mutated hemagglutinin resulting from replacement of the 136th serine residue of hemagglutinin derived from the Aic68 strain influenza virus with threonine or alanine, wherein grey peaks indicate the results of Mock-transfection, green peaks indicate the results for the HA of wild type Aic68, blue peaks indicate the results for S136T of HA of Aic68, and pink peaks indicate the results for S136A of HA of Aic68.

FIG. 19 shows the results of a FACS analysis of the bindability of F045-092 for cells expressing mutated HA1 resulting from mutual replacement of the 142nd-146th or 133rd-137th amino acids of HA1 derived from various H3N2 influenza viruses, wherein grey peaks indicate the results of Mock-transfection, green peaks indicate the reactivity to the wild type, pink peaks indicate the reactivity to the chimera 142A to which the 142nd-146th amino acid sequence has been transplanted, and blue peaks indicate the reactivity to the chimera 133A to which the 133rd-137th amino acid sequence has been transplanted.

FIG. 20 shows the three-dimensional structures of the 91st-260th amino acid portions of mutated HA1 regions resulting from mutual replacement of the 142nd-146th or 133rd-137th amino acids of the HA1 derived from various H3N2 influenza viruses, wherein the receptor-binding region appears in orange, the 133rd-137th amino acids of Aic68_Wild in blue, the 142nd-146th amino acids in light blue, the 133rd-137th amino acids of Wyo03_Wild in red, the 142nd-146th amino acids in pink, the 133rd-137th amino acids of Fuk85_Wild in green, and the 142nd-146th amino acids in yellow-green.

FIG. 21 shows the three-dimensional structures of the 91st-260th amino acid portions of the HA1 region of H3N2 influenza viruses, the sites of HA1 region recognized by various antibodies, and the names of viral strains used in determining the sites by the EMAC method, wherein the receptor-binding region is shown in orange, the sites recognized by the respective anti-HA antibodies in pink, amino acid numbers in the receptor-binding region in black, the amino acid numbers of antigen recognition sites in blue, and the amino acids contained as antigen recognition sites in the receptor-binding region in blue.

FIGS. 22-1, 22-2, 22-3, 22-4 and 22-5 are a graphic representation of the results of an experiment of competition between various anti-HA antibodies that bind to the sites A, B, C, D, and E in HAL and the F045-092 antibody, wherein each left graph was generated with F045-092 as the competitor, and each right graph was generated with the cp3 type of anti-HA antibody as the competitor (+: with cp3 antibody, −: without cp3 antibody). The viral strains used are shown in the lower left of each graph. No Fab-pp: PBS was used in place of pp type antibody; No Ab: PBS was used in place of all antibodies.

DESCRIPTION OF EMBODIMENTS

Figure 6:
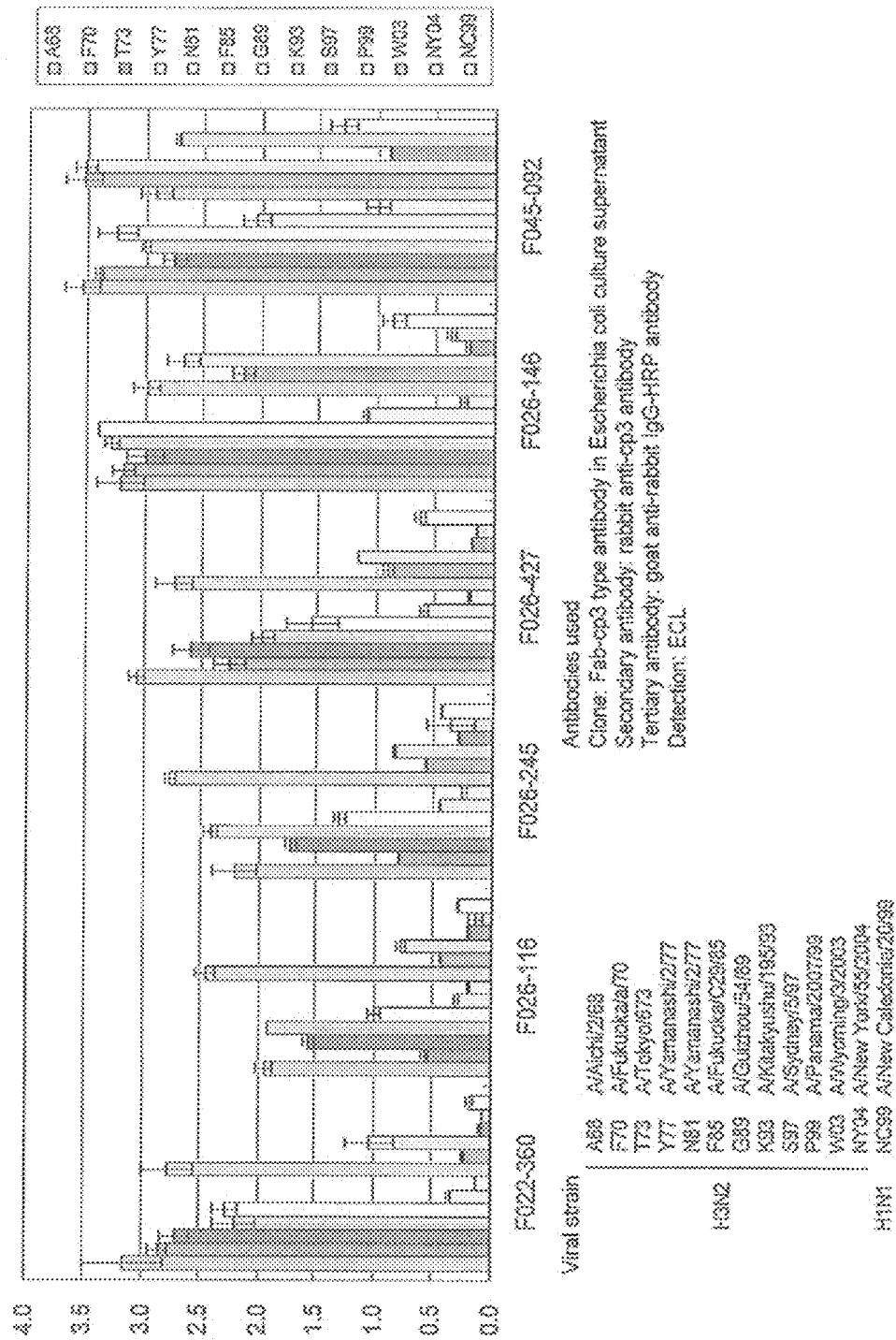
FIG. 6 shows the results of an ELISA determination of the binding activities of clones classified under Group.11 for H3N2 influenza virus strains.

Herein, influenza viruses include all currently known subtypes and even subtypes that will possibly be isolated and identified in the future. Currently known subtypes of influenza viruses include subtypes consisting of a combination of a type of hemagglutinin selected from among H1 to H16 and a type of neuraminidase selected from among N1 to N9.

Influenza viruses are roughly divided into two groups according to the similarity of the amino acid sequence of hemagglutinin. Herein, the group consisting of subtype H1, subtype H2, subtype H5, subtype H6, subtype H8, subtype H9, subtype H11, subtype H12, subtype H13 and subtype H16 influenza viruses is referred to as Group 1, and the group consisting of subtype H3, subtype H4, subtype H7, subtype H10, subtype H14 and subtype H15 influenza viruses as Group 2. In selecting a category in these groups, the subtype of neuraminidase is not considered. Novel subtypes that will be isolated and identified in the future will be classified under either Group 1 or Group 2 according to the similarity of the amino acid sequence of hemagglutinin.

The present invention provides an isolated antibody that neutralizes both at least one influenza virus selected from Group 1 (subtype H1, subtype H2, subtype H5, subtype H6, subtype H8, subtype H9, subtype H11, subtype H12, subtype H13 and subtype H16) and at least one influenza virus selected from Group 2 (subtype H3, subtype H4, subtype H7, subtype H10, subtype H14 and subtype H15). Preferably, the neutralizing antibody of the present invention neutralizes at least subtype H1 and/or subtype H5 influenza viruses in Group 1, and also neutralizes at least subtype H3 influenza viruses in Group 2. More preferably, the neutralizing antibody of the present invention further neutralizes subtype H9 influenza viruses in Group 1, and also further neutralizes subtype H7 influenza viruses in Group 2. The neutralizing antibody of the present invention particularly preferably neutralizes all of subtype H1 to H16 influenza viruses, most preferably neutralizes even influenza viruses of a novel hemagglutinin subtype that will be isolated and identified in the future.

The neutralizing antibody of the present invention can be produced by a method comprising the steps of:

(1) providing an antibody library comprising antibody clones derived from more than about $10^8$ B cells collected from one individual;

(2) contacting an influenza virus of any one of subtypes H1 to H16 or the hemagglutinin protein of the virus or an extracellular domain thereof as the antigen with the antibody library provided in the step (1), and comprehensively selecting antibody clones that react with the antigen;

(3) recovering antibody molecules from each antibody clone selected in the step (2);

(4) testing each antibody obtained in the step (3) for neutralizing activity against at least one influenza virus selected from Group 1 and at least one influenza virus selected from Group 2; and (5) producing an antibody that has neutralized both an influenza virus belonging to Group 1 and an influenza virus belonging to Group 2 using a clone that produces the antibody, and recovering the antibody.

The donor from which B cells as the antibody-producing cells for generating the antibody library are collected may be any optionally chosen mammal (e.g., humans, swine, horses and the like) or bird (chicken, ducks and the like) that has ever been infected with influenza virus; the same animal species as the subject to passively immunize with the neutralizing antibody of the present invention can be chosen as appropriate, with preference given to a human. In the case of a human, the donor's age, sex, vaccination status (vaccinated or not) and the like are not limited; however, since the donor desirably has as much experience with influenza virus infection as possible, the donor is preferably 20 years or older, more preferably 30 years or older, still more preferably 40 years or older, particularly preferably 50 years or older, which ages, however, are not to be construed as limiting. Because an antibody that exhibits neutralizing activity beyond the barrier of the groups is capable of neutralizing all viral isolates in all groups and all subtypes, donors having cells that produce the neutralizing antibody are thought to be unlikely to contract every year's seasonal influenza. Therefore, a human having no history of contracting type A influenza during a given period in the past is further desirable.

The amount of blood drawn for collecting B cells to be used to prepare an ordinary antibody library is about 20 to 30 mL, the number of B cells contained in this volume of blood is about $10^7$. All the study groups that isolated human neutralizing antibodies against the highly pathogenic H5N1 avian influenza virus generated their antibody library of about $10^{10}$ clones by collecting an ordinary amount of blood from a plurality of donors, and combining them, whereas the present inventors attempted to generate an antibody library of a size that reflects the entire antibody repertory with the aim of exhaustively (comprehensively) acquiring antibodies that bind to a certain subtype of hemagglutinin. Usually, the amount of blood drawn from a human in a single operation is limited to about 200 to 300 mL; therefore, the number of B cells collectable using this method is at most about $10^8$. With this in mind, the present inventors collected B cells contained in a larger amount of blood from one individual using apheresis. Preferably, the antibody library used for the purpose of the present invention is built from more than $10^9$ B cells. For example, collection of about $10^9$ B cells from one human individual can be achieved by separating B cells from about 3 L of blood by apheresis.

The antibody-producing cells for generating the antibody library may further comprise antibody-producing cells derived from another individual, as far as about $10^8$ or more, preferably about $10^9$ or more, B cells derived from one individual are contained. Specifically, for example, a number of mononuclear cells equivalent to about 3 L of blood are recovered by apheresis, after which B cells can be isolated and recovered by, for example, Ficoll-Paque density gradient centrifugation and the like.

Antibody libraries include, but are not limited to, for example, phage display libraries, libraries obtained by immortalizing B cells using EB virus, hybridoma libraries obtained by fusing B cells and myeloma cells, and the like. Preferably, a phage display library may be used.

Examples of methods of generating a phage display human antibody library as mentioned herein include, but are not limited to, the following.

Although the choice of phage used is not particularly limited, a filamentous phage (Ff bacteriophage) is usually preferably used. Methods of presenting an extraneous protein onto the phage surface include a method wherein the extraneous protein is expressed and presented as a fusion protein with one of the coat proteins g3p(cp3) and g6p(cp6) to g9p(cp9) on the coat protein, and a commonly used method wherein the extraneous protein is fused to the N-terminal side of cp3 or cp8. Phage display vectors include 1) those that introduce an extraneous gene in a fused form into the coat protein gene in the phage genome to allow all coat protein presented onto the phage surface to be presented as a fusion protein with the extraneous protein, as well as 2) those that insert a gene that encodes a fusion protein separately from a wild type coat protein gene to concurrently express the fusion protein and the wild type coat protein, and 3) those that allow *Escherichia coli* having a phagemid vector harboring a gene that encodes a fusion protein to be infected with a helper phage having the wild type coat protein gene and produce phage particles that concurrently express the fusion protein and the wild type coat protein. In the case 1), fusion with a large extraneous protein can result in the loss of the infectivity; therefore, in such cases, a method of type 2) or 3) is used in generating the antibody library.

Specifically, useful vectors include those described by Holt et al. (Curr. Opin. Biotechnol., 11: 445-449, 2000). For example, pCES1 (see J. Biol. Chem., 274: 18218-18230, 1999) is an Fab expression type phagemid vector harboring a DNA that encodes a κL chain constant region placed downstream of the signal peptide of cp3, a DNA that encodes $C_{H3}$, and the cp3-encoding sequence placed via a His-tag, a c-myc tag, and an amber stop codon (TAG) downstream of the cp3 signal peptide, under the control of one lactose promoter. The vector presents Fab onto the cp3 coat protein when introduced into *Escherichia coli* having an amber mutation. When it is expressed in the HB2151 strain, which does not have an amber mutation, and the like, however, the strain produces a soluble Fab antibody. Useful scFv expression type phagemid vectors include, for example, pHEN1 (J. Mol. Biol., 222:581-597, 1991) and the like.

Meanwhile, helper phages include, for example, M13-KO7, VCSM13 and the like.

Other phage display vectors include those designed to join a sequence comprising a codon that encodes cysteine to each of the 3' terminus of the antibody gene and the 5' terminus of the coat protein gene to express the two genes concurrently and separately (not as a fusion protein), and to allow the antibody to be presented onto the coat protein on the phage surface via the S—S bond between the introduced cysteine residues (Morphosis Company's CysDisplay™ technology) and the like.

Kinds of antibody libraries generated in the present invention include naive/non-immunized libraries, synthetic libraries, immunized libraries and the like.

A naive/non-immunized library is obtained by acquiring $V_H$ and $V_L$ genes retained by a normal animal by RT-PCR, and randomly cloning the same into one of the above-described phage display vectors. Usually, mRNA or the like derived from lymphocytes (preferably peripheral blood lymphocytes) of peripheral blood, bone marrow, tonsil and the like of normal animals is used as the template. A library generated by amplifying only mRNA derived from IgM that has not undergone a class switch due to antigen sensitization to avoid biases related to the V gene, such as anamnesis, is especially called a naive library. Representative naive/non-immunized libraries include CAT Company's library (see J. Mol. Biol., 222: 581-597, 1991; Nat. Biotechnol., 14: 309-314, 1996), MRC Company's library (see Annu. Rev. Immunol., 12: 433-455, 1994), Dyax Company's library (see J. Biol. Chem., 1999 (ibid.); Proc. Natl. Acad. Sci. USA, 14: 7969-7974, 2000) and the like.

A synthetic library is generated by choosing a particular antibody gene that is functional in human B cells, and replacing a portion of the V gene fragment, for example, a portion of the antigen-binding region of CDR3 and the like, with a DNA that encodes a random amino acid sequence with an appropriate length. Synthetic libraries are recognized as being excellent in antibody expression efficiency and stability because they can be built with a combination of $V_H$ and $V_L$ genes that produce scFv and Fab that are functional from the beginning. Representative examples include Morphosys Company's HuCAL library (see J. Mol. Biol., 296: 57-86, 2000), BioInvent Company's library (see Nat. Biotechnol., 18: 852, 2000), Crucell Company's library (see Proc. Natl. Acad. Sci. USA, 92: 3938, 1995; J. Immunol. Methods, 272: 219-233, 2003) and the like. When using a synthetic library, it is desirable to use a VH1-69 or VH1-e gene fragment as the V gene fragment of the heavy-chain variable domain.

An immunized library is generated by preparing mRNA from lymphocytes collected from a human having an elevated blood antibody titer against the target antigen, such as a recipient of vaccination, or from lymphocytes collected from a human artificially immunized with the target antigen by external immunization, and the like, in the same manner as with the above-described naive/non-immunized library, and amplifying the $V_H$ and $V_L$ genes by RT-PCR. Because the desired antibody gene is present in the library already at the beginning, the desired antibody can be obtained even from a library of relatively small size. In the case of humans, however, because an antibody specific for the subtype of the virus inoculated by vaccination gets amplified, vaccination with an influenza virus of one of the hemagglutinin subtypes H1 to H3, against which many antibodies are estimated to exist in the body, leads to amplification of antibodies possessing a narrow range of neutralizing activity such that only a particular isolate in the subtype can be neutralized; it is feared that the desired neutralizing antibody is masked. Therefore, in vaccination, it is preferable that a vaccine for an influenza virus of a subtype with which extensive infection has not been reported to date (e.g., in the case of a human, H5, H7, H9 and the like) be inoculated.

The greater the diversity of the library is, the better; in reality, and taking into account the number of phages handleable in the subsequent panning operation ($10^{11}$-$10^{13}$ phages) and the number of phages needed for clone isolation and propagation in ordinary panning (100 to 1,000 phages/clone), however, the size of the library is suitably about $10^8$ to $10^{11}$ clones. Preferably, the size is $10^9$ and $10^6$ clones for the $V_H$ and $V_L$ genes, respectively, and the number of Fab or scFv clones is $10^{10}$ to $10^{11}$ clones.

Methods of generating an antibody library by immortalization using EB virus include, but are not limited to, for example, the method described in PLos Medicine 4(5): e178 0928-9936 (2007). The majority of persons have immunity against EB virus because they have ever been infected with the virus in the context of asymptomatic infection with infectious mononucleosis; when using an ordinary EB virus, however, virions are also produced, so that appropriate purification must be performed. It is also preferable to use a recombinant EB virus retaining the capability of immortalizing B lymphocytes, but lacking the capability of virion replication (e.g., lack of the switching gene for transition from latent infection state to lytic infection state, and the like) as an EB system that can never be contaminated with the virus.

Because marmoset-derived B95-8 cells secrete EB virus, B lymphocytes can be easily transformed using a culture supernatant thereof. An antibody-producing B cell line can be obtained by, for example, culturing these cells using a medium supplemented with serum and penicillin/streptomycin (P/S) (e.g., RPMI1640) or a serum-free medium supplemented with a cell proliferation factor, thereafter separating the culture supernatant by filtration or centrifugation and the like, suspending therein antibody-producing B lymphocytes at an appropriate concentration (e.g., about $10^7$ cells/mL), and incubating the suspension normally at 20 to 40° C., preferably at 30 to 37° C., normally for about 0.5 to 2 hours. When human antibody-producing cells are provided as mixed lymphocytes, it is preferable to previously remove T lymphocytes by allowing them to form an E rosette with, for example, sheep erythrocytes and the like, to increase transformation frequency, because the majority of persons have T lymphocytes that are toxic to cells infected with EB virus. It is also possible to select lymphocytes specific for the target antigen by mixing sheep erythrocytes, previously coupled with a soluble antigen, with antibody-producing B lymphocytes, and separating the rosette using a density gradient of Percoll and the like. Furthermore, because antigen-specific B lymphocytes are capped by adding the antigen in large excess so that they no longer present IgG onto the surface, mixing with sheep erythrocytes previously coupled with an anti-IgG antibody results in the formation of a rosette only by antigen-nonspecific B lymphocytes. Therefore, by collecting a layer of cells that do not form a rosette from this mixture using a density gradient of Percoll and the like, it is possible to select antigen-specific B lymphocytes.

Antibody-secreting cells that have acquired the capability of indefinite proliferation as a result of the transformation can be back-fused with mouse or human myeloma cells in order to stably sustain the antibody-secreting ability. Examples of the myeloma cells include mouse myeloma cells such as NS-1, P3U1, SP2/0, and AP-1, and human myeloma cells such as SKO-007, GM 1500-6TG-2, LICR-LON-HMy2, and UC729-6.

Generation of an antibody library by cell fusion can be achieved according to ordinary procedures for hybridoma preparation for generating a monoclonal antibody. Specifically, an antibody-producing hybridoma can be prepared by fusing a B cell collected from a donor and one of the above-described myeloma cells.

Fusion operation can be performed according to a known method, for example, the method of Koehler and Milstein [Nature, vol. 256, p.495 (1975)]. Fusion promoters include polyethylene glycol (PEG), Sendai virus and the like, with preference given to PEG and the like. Although the molecular weight of PEG is not subject to limitations, PEG1000 to PEG6000, which are of low toxicity and relatively low viscosity, are preferable. Examples of PEG concentrations include about 10-80%, preferably about 30-50%. Useful solutions for diluting PEG include various buffer solutions such as serum-free media (e.g., RPMI1640), complete media comprising about 5-20% serum, phosphate buffered saline (PBS), and Tris buffer. DMSO (e.g., about 10-20%) can also be added as desired. Examples of the pH of the fusion solution include about 4 to 10, preferably about 6 to 8.

The ratio by number of B cells and myeloma cells is normally about 1:1 to 20:1; the cell fusion can be efficiently achieved by incubation normally at 20-40° C., preferably at 30-37° C., normally for 1 to 10 minutes.

Hybridoma screening and breeding are normally performed using a medium usable for animal cells (e.g., RPMI1640) comprising 5-20% FCS or a serum-free medium supplemented with cell proliferation factors, with the addition of HAT (hypoxanthine, aminopterin, thymidine). Examples of the concentrations of hypoxanthine, aminopterin and thymidine include about 0.1 mM, about 0.4 µM and about 0.016 mM and the like, respectively. For selecting a human+−+−mouse hybridoma, ouabain resistance can be used. Because human cell lines are more susceptible to ouabain than mouse cell lines, it is possible to eliminate unfused human cells by adding ouabain at about $10^{-7}$ to $10^{-3}$ M to the medium.

In selecting a hybridoma, it is preferable to use feeder cells or culture supernatants of certain cells. As the feeder cells, an allogenic cell species having a lifetime limited so that it dies after helping the emergence of hybridoma, cells capable of producing large amounts of a growth factor useful for the emergence of hybridoma with their proliferation potency reduced by radio-irradiation and the like, and the like are used. For example, mouse feeder cells include splenocytes, macrophages, blood, thymocytes and the like; human feeder cells include peripheral blood mononuclear cells and the like. Cell culture supernatants include, for example, primary culture supernatants of the above-described various cells and culture supernatants of various established cell lines.

The step of selecting an antibody against a target antigen by the phage display method is called panning. To be specific, a phage presenting an antigen-specific antibody is concentrated by repeating about 2 to 4 times a series of operations of bringing a carrier having an influenza virus of any one of subtypes H1 to H16 or the hemagglutinin protein of the virus or an extracellular domain thereof, immobilized thereon, and a phage library into contact with each other, washing out the unbound phage, thereafter eluting the bound phage from the carrier, and infecting the phage to *Escherichia coli* to proliferate the phage. In the present invention, the influenza virus serving as the antigen may have been inactivated by formalin treatment. It is preferable that the influenza virus isolate used as the antigen be one with which the individual from which the B cells have been collected has never been infected. This is because when using as the antigen a viral isolate with which the individual has ever been infected, it is feared that an antibody clone that exhibits neutralizing activity only in a narrow range becomes dominant and masks the neutralizing antibody desired in the present invention. Therefore, preferably, an influenza virus belonging to a hemagglutinin subtype with which the individual from which the B cells have been collected has never been infected, or hemagglutinin thereof, can be used as the antigen. Examples include influenza viruses of subtype H5, subtype H7, and subtype H9. Alternatively, when using as the antigen an influenza virus isolate belonging to any one of subtypes H1 to H3, it is desirable, for example, to use an isolate of a subtype that once prevailed before the birth of the individual from which the B cells have been collected.

The cDNA sequences that encode the hemagglutinins of the various subtypes are publicly known; recombinant hemagglutinin of any desired subtype can be produced using ordinary gene recombination techniques. Furthermore, the trimeric extracellular domain structure of hemagglutinin can be generated in accordance with a method described in the above-described non-patent document 6.

Useful carriers for immobilizing the antigen include various carriers for use in ordinary antigen-antibody reactions or affinity chromatography, for example, insoluble polysaccharides such as agarose, dextran, and cellulose; synthetic resins such as polystyrene, polyacrylamide, and silicon; microplates, tubes, membranes, columns, beads and the like comprising glass, metal and the like; surface plasmon resonance (SPR) sensor chips, and the like. For the antigen immobilization, physical adsorption may be used, and a method using a chemical bond in use for insolubilizing and immobilizing a protein or enzyme and the like is also acceptable. For example, a biotin-(strept)avidin system and the like are preferably used. For washing the unbound phage, a blocking solution such as BSA solution (once or twice), a PBS comprising a surfactant such as Tween (3 to 5 times) and the like can be used in sequence. A report is available mentioning that the use of citrate buffer solution (pH 5) and the like is preferable. For elution of the specific phage, an acid (e.g., 0.1 M hydrochloric acid and the like) is normally used; cleavage with a specific protease (e.g., a gene sequence that encodes a trypsin cleavage site can be introduced into the linkage site between the antibody gene and the coat protein gene; in this case, *Escherichia coli* infection and proliferation are possible even if all the coat protein is expressed in the form of a fusion protein because the wild-type coat protein is presented on the surface of the eluted phage), competitive elution with a soluble antigen, or elution by reduction of the S—S bond (e.g., in the aforementioned CysDisplay™, the antigen-specific phage can be recovered by dissociating the antibody and the coat protein by using a suitable reducing agent after performing panning) is also possible. When elution has been performed with an acid, the eluate is neutralized with Tris and the like, and the eluted phage is then infected to *Escherichia coli*, which is then cultured, after which the phage is recovered by a conventional method.

In place of immobilizing the antigen onto a carrier, it is possible to express a hemagglutinin trimer on the cell membrane using a yeast display.

After the phage presenting the antigen-specific antibody is concentrated by panning, the phage is infected to *Escherichia coli*, and the cells are seeded onto a plate and subjected to cell cloning. The phage is again recovered, and the antigen binding activity is confirmed by an antibody titer assay (e.g., ELISA, RIA, FIA and the like) or a measurement utilizing fluorescence activated cell sorting (FACS) or surface plasmon resonance (SPR).

The step of infecting the phage antibody clone obtained above to *Escherichia coli*, and recovering the antibody from the culture supernatant, can be performed by, for example, infecting the phage to a strain of *Escherichia coli* that does not have an amber mutation (e.g., HB2151 strain) to produce and secrete soluble antibody molecules in the periplasm or the medium, lysing the cell wall with lysozyme and the like, recovering the extracellular fraction, and purifying the fraction using as the phage display vector the same purification technique as the above, when using a vector incorporating an amber stop codon at the linker site between the antibody gene and the coat protein gene. Provided that a His-tag or c-myc tag has been introduced in advance, the antibody can easily be purified using IMAC, an anti-c-myc antibody column and the like. When cleavage with a specific protease is utilized in panning, the antibody molecule is separated from the phage surface by allowing the protease to act thereon, so that the desired antibody can be purified by performing the same purification operation. In the present invention, since the neutralizing activity of the antibody is higher about 100 to 1000 fold when the antibody is a complete antibody of the IgG type than of the Fab type, the plasmid DNA is recovered from the phage clone obtained, a sequence corresponding to the domain that binds to the Fc of IgG is added by gene manipulation, *Escherichia coli* is transformed therewith, and the transformant is cultured, as described in Examples below. The antibody recovered from the culture supernatant is purified using an IgG Sepharose column and then tested for neutralizing activity.

The desired antibody can also be selected from an antibody-producing cell line obtained by immortalization using EB virus or cell fusion by, for example, reacting the above-described antigen, previously labeled with a fluorescent substance, with immortalized cells or fusion cells, and then separating the cells that bind to the antigen using a fluorescence-activated cell sorter (FACS). In this case, a hybridoma or immortalized B cells that produce an antibody against the target antigen can be selected directly, so that the labor of cloning can be lessened significantly.

Various methods can be used for cloning a hybridoma that produces a monoclonal antibody against the target antigen. Because aminopterin inhibits many cell functions, it is preferable to remove it from the medium as soon as possible. However, human hybridomas are maintained using an aminopterin-supplemented medium normally for about 4 to 6 weeks after fusion. It is desirable that hypoxanthine and thymidine be removed after 1 week or more has elapsed after removal of aminopterin. When a clone has emerged and its diameter has reached about 1 mm, the antibody content in the culture supernatant can be measured.

The amount of antibody can be measured by, for example, a method wherein the hybridoma culture supernatant is added to a solid phase (e.g., microplates) with the target antigen or a derivative thereof or a partial peptide thereof adsorbed thereto as it is alone, or along with a carrier, an anti-immunoglobulin (IgG) antibody (an antibody against IgG derived from the same animal species as the animal from which the original antibody-producing cells are derived is used) or Protein A, previously labeled with a radioactive substance (e.g., $^{125}I$, $^{131}I$, $^{3}H$, $^{14}C$), an enzyme (e.g., β-galactosidase, β-glucosidase, alkaline phosphatase, peroxidase, malate dehydrogenase), a fluorescent substance (e.g., fluorescamine, fluorescein isothiocyanate), a luminescent substance (e.g., luminol, luminol derivatives, luciferin, lucigenin) or the like, is added, and an antibody against the target antigen bound to the solid phase is detected; a method wherein the hybridoma culture supernatant is added to a solid phase with an anti-IgG antibody or Protein A adsorbed thereto, a target antigen labeled with the same labeling agent as the above or a derivative thereof or a partial peptide thereof is added, and an antibody against the target antigen bound to the solid phase is detected, and the like.

Although limiting dilution is normally used as the cloning method, cloning using soft agar and cloning using FACS (described above) are also possible. Cloning by limiting dilution can be performed by, for example, the following procedures, which, however, are not to be construed as limiting.

The amount of antibody is measured as described above, and positive wells are selected. Previously, appropriate feeder cells have been chosen and added to a 96-well plate. Cells are aspirated from antibody-positive wells and suspended in a complete medium [e.g., RMPI1640 supplemented with 10% FCS (fetal calf serum) and P/S] to obtain a density of 30 cells/mL; 0.1 mL (3 cells/well) of this suspension is added to the 96-well plate with feeder cells added thereto; a portion of the remaining cell suspension is diluted to 10 cells/mL and seeded to other wells (1 cell/well) in the same way; the still remaining cell suspension is diluted to 3 cells/mL and seeded to other wells (0.3 cells/well). The cells are cultured for about 2 to 3 weeks until a visible clone appears; the amount of antibody is measured, and positive wells are selected and recloned. In the case of human cells, cloning is relatively difficult, so that a plate containing 10 cells per well is also prepared. Although a monoclonal antibody-producing hybridoma can be obtained normally by two times of subcloning, it is desirable to repeat recloning regularly for several more months to confirm the stability thereof.

Hybridomas can be cultured in vitro or in vivo.

Methods of in vitro culture include a method comprising gradually scaling up the production of a monoclonal antibody-producing hybridoma obtained as described above, from a well plate, while keeping the cell density at, for example, about $10^5$ to $10^6$ cells/mL, and gradually lowering the FCS concentration.

Methods of in vivo culture include, for example, a method comprising an intraperitoneal injection of mineral oil into a mouse (a mouse that is histocompatible with the parent strain of the hybridoma) to induce plasmacytoma (MOPC), intraperitoneally injecting about $10^6$ to $10^7$ cells of the hybridoma 5 to 10 days later, and collecting ascites fluid under anesthesia 2 to 5 weeks later.

Separation and purification of the monoclonal antibody are performed according to a method of immunoglobulin separation and purification [e.g., salting-out, alcohol precipitation, isoelectric point precipitation, electrophoresis, adsorption-desorption with an ion exchanger (e.g., DEAE, QEAE), ultracentrifugation, gel filtration, specific purification comprising selectively collecting the antibody by means of an antigen-coupled solid phase or an active adsorbent such as protein A or protein G, and dissociating the linkage to obtain the antibody, and the like] in the same manner as with the ordinary separation and purification of a polyclonal antibody.

As described above, a monoclonal antibody that binds to an influenza virus of a particular hemagglutinin subtype can be screened for by culturing the hybridoma in or outside the body of a warm-blooded animal, and harvesting the antibody from a body fluid or culture thereof.

Whether the thus-obtained monoclonal antibody can neutralize influenza virus beyond the barrier of the groups can be determined by testing neutralizing activities against at least one influenza virus selected from Group 1 and at least one influenza virus selected from Group 2.

Usually, an investigation of neutralizing activity against influenza virus is often performed by hemagglutination inhibition (HI) test. Influenza virus binds to erythrocytes via the head region of hemagglutinin, with a sugar chain comprising sialic acid (sialosugar chain) present on the erythrocyte surface as the influenza virus receptor. As a result, the influenza virus causes the erythrocytes to agglutinate. Because an antibody with neutralizing activity against influenza virus recognizes and binds to hemagglutinin, the hemagglutination property of influenza virus is suppressed by a neutralizing antibody. Therefore, the presence or absence of suppression of hemagglutination serves as an index of the presence or absence of neutralizing activity. While the region involved in the hemagglutination of hemagglutinin is likely to undergo an antigenic drift, the amino acid involved in the sialic acid bond in the region tends to be highly conserved via subtypes of influenza virus, suggesting that the neutralizing antibody of the present invention, which possesses a broad range of neutralizing activity, recognizes the amino acid as an epitope. Alternatively, neutralizing activity test methods in the present invention include, for example, the focus formation inhibition test [J. Clin. Microbiol. Vol. 28, pp. 1308-1313 (1990)]. Specifically, influenza virus and host cells are contacted with each other in the presence and absence of the test antibody, and the presence or absence of neutralizing activity and the level thereof are determined on the basis of whether the test antibody significantly inhibits focus formation due to viral infection to the host cells.

Although the subtype of the influenza virus to be tested for neutralizing activity is not particularly limited, it is preferable that at least subtype H1 and/or subtype H5 influenza viruses in Group 1 and at least subtype H3 influenza viruses in Group 2 be included. Alternatively, it is also preferable to further examine neutralizing activity against influenza virus of subtype H9 in Group 1, and against influenza virus of subtype H7 in Group 2.

Using a clone that produces an antibody molecule confirmed to neutralize at least one influenza virus selected from Group 1 and at least one influenza virus selected from Group 2 in an antibody molecule neutralizing activity test, the antibody molecule can be produced in large amounts. When the antibody library used is a phage display library, a phage clone that presents an Fab or scFv of the desired neutralizing antibody may be infected to *Escherichia coli*, which may be cultured to yield an Fab type antibody or an scFv type antibody, with preference given to converting them to type IgG antibodies for the purpose of remarkably enhancing their neutralizing activities. For example, conversion of Fab to IgG can be achieved by cutting out fragments that encode VHCH1 and VLCL from the phage DNA, inserting the fragments into a plasmid comprising a fragment that encodes the Fc region to build a plasmid comprising a DNA that encodes the heavy chain and light chain, transfecting animal cells such as CHO cells therewith, and culturing the cells to allow them to secrete a type IgG antibody in the culture supernatant. The antibody obtained can be purified and recovered by a method known per se.

When the antibody library used is a hybridoma prepared by B cell immortalization using EV virus or cell fusion, it is possible to allow the hybridoma to produce the antibody molecule in vitro or in vivo as described above, purify the antibody by a conventional method, and recover the antibody.

For the neutralizing antibody obtained, it is possible to mimic steps employed by the immune system (somatic cell mutation and selection) to enhance its affinity for antigens in vitro. Methods of mutagenesis in antibody genes include chain shuffling, random mutagenesis using *Escherichia coli*, which is likely to lack its repair system to undergo mutations, or error-prone PCR, CDR walking and the like. Selection of a neutralizing antibody with improved affinity for antigens can be achieved by screening for a high-affinity neutralizing antibody from a library of mutants generated by the mutagenesis. For example, 1) a method wherein an antibody phage with high affinity is recovered at low concentrations of the antigen used for selection, 2) a method wherein an antibody phage unlikely to leave the antigen is recovered using rigorous washing conditions, 3) a method wherein an antagonizing reaction is utilized, and the like can be used.

The kinds of the neutralizing antibody of the present invention obtained as described above mostly utilize the VH1-69 or VH1-e gene as the heavy-chain variable domain V region. This feature is shared by a variety of antibodies that have been reported so far to neutralize influenza viruses of a plurality of subtypes in Group 1; it is interesting to note that a definite difference exists in the range of neutralizing activity exhibited, while the same V gene fragment is utilized. A feature of the neutralizing antibody of the present invention is that only the VL1-44, VL1-47 or VL1-51 gene is utilized as the light-chain variable domain V region. Also, the neutralizing antibody of the present invention has a minimum inhibitory concentration on the order of $10^{-11}$-$10^{-12}$ M in a focus formation inhibition test with a type IgG antibody, exhibiting higher levels of neutralizing activity than those of all antibodies that have been reported so far to neutralize influenza viruses of a plurality of subtypes in Group 1.

An antibody undergoes immunoglobulin gene rearrangements, i.e., recombination of the V, D, and J regions in the heavy-chain variable domain or recombination of the V and J regions in the light-chain variable domain, in the process of B cell differentiation, after which somatic cell mutations are induced in the base sequence of the variable domains. As a result, an antibody having variable domains with higher affinity for antigens can be produced. Therefore, the kinds of the neutralizing antibody of the present invention, which are B-cell-derived antibody clones, can even include neutralizing antibodies having an amino acid sequence resulting from a somatic cell mutation in the original immunoglobulin gene. In the formation of an antigen-antibody conjugate of a neutralizing antibody and an influenza virus antigen, all points of contact with the hemagglutinin molecule are present in the heavy-chain variable domain; therefore, the heavy-chain variable domain was thought to be the site making a substantial contribution to the affinity of the neutralizing antibody for influenza virus; however, convergence was also observed in the variation of the light-chain variable domain, which suggested that the light-chain variable domain also plays a certain role in the neutralizing antibody of the present invention. Because the contribution of the complementarity determining region 3 (CDR3) to the binding with the antigen is small in the neutralizing antibody of the present invention, the complementarity determining regions 1 and 2 present in the heavy-chain variable domain V region are more important. Herein, a heavy-chain variable domain V region (light-chain variable domain V region) refers to a V region after rearrangement to constitute the variable domain of the heavy chain (light chain), and can be, for example, a region comprising the framework regions 1, 2 and 3 and the complementarity determining regions 1 and 2. A heavy-chain (light-chain) variable domain refers to a portion of antibody that is not the constant region of the Fab region, and can be, for example, a region comprising the framework regions 1, 2 and 3 and the complementarity determining regions 1, 2 and 3. Therefore, the neutralizing antibody of the present invention is preferably, for example, a neutralizing antibody having the amino acid sequence of SEQ ID NO:1 as the complementarity determining region 1 of the heavy-chain variable domain, and also having the amino acid sequence of SEQ ID NO:2 as the complementarity determining region 2.

The present inventors also obtained a clone that possesses remarkable neutralizing activity against subtypes H1, H2 and H5, which belong to Group 1, compared with other clones, while possessing neutralizing activity against influenza viruses of subtype H3, which belongs to Group 2. This clone, unlike other clones, has a structure wherein one amino acid (the 27th glycine in SEQ ID NO:27) of the framework region 1 in the heavy-chain variable domain is lacked. Therefore, a neutralizing antibody wherein the framework region 1 of the heavy-chain variable domain consists of the amino acid sequence shown by SEQ ID NO:3 is also preferable as the neutralizing antibody of the present invention.

Further specific examples include a neutralizing antibody wherein the heavy-chain variable domain V region consists of the amino acid sequence shown by any one of SEQ ID NOs:4-9, a neutralizing antibody wherein the heavy-chain variable domain consists of the amino acid sequence shown by any one of SEQ ID NOs:10-15, and a neutralizing antibody wherein the heavy-chain variable domain (SEQ ID NOs:10-15) and the light-chain variable domain (SEQ ID NOs:16-26 and 70) consist of one of the combinations of amino acid sequences shown below.
(a) SEQ ID NO:10, SEQ ID NO:16;
(b) SEQ ID NO:10, SEQ ID NO:17;
(c) SEQ ID NO:10, SEQ ID NO:18;
(d) SEQ ID NO:10, SEQ ID NO:19;
(e) SEQ ID NO:10, SEQ ID NO:20;
(f) SEQ ID NO:10, SEQ ID NO:21;
(g) SEQ ID NO:10, SEQ ID NO:22;
(h) SEQ ID NO:11, SEQ ID NO:23;
(i) SEQ ID NO:13, SEQ ID NO:24;
(j) SEQ ID NO:14, SEQ ID NO:25;
(k) SEQ ID NO:15, SEQ ID NO:26: or
(l) SEQ ID NO:12, SEQ ID NO:70

Examples also include the base sequences shown by SEQ ID NOs:71-76 as the base sequences encoding the amino acid sequences of the heavy-chain variable domains of the foregoing antibodies (SEQ ID NOs:10-15), respectively, and the base sequences shown by SEQ ID NOs:77-88 encoding the amino acid sequences of the light-chain variable domains (SEQ ID NOs:16-26 and 70), respectively. Therefore, the neutralizing antibody of the present invention is exemplified by a neutralizing antibody wherein the heavy-chain variable domain consists of the amino acid sequence encoded by the base sequence shown by any one of SEQ ID NOs:71-76, and a neutralizing antibody wherein the heavy-chain variable domain and the light-chain variable domain consist of the amino acid sequences encoded by one of the combinations of base sequences shown below.
(a) SEQ ID NO:71, SEQ ID NO:77;
(b) SEQ ID NO:71, SEQ ID NO:78;
(c) SEQ ID NO:71, SEQ ID NO:79;
(d) SEQ ID NO:71, SEQ ID NO:80;
(e) SEQ ID NO:71, SEQ ID NO:81;
(f) SEQ ID NO:71, SEQ ID NO:82;
(g) SEQ ID NO:71, SEQ ID NO:83;
(h) SEQ ID NO:72, SEQ ID NO:84;

(i) SEQ ID NO:74, SEQ ID NO:85;
(j) SEQ ID NO:75, SEQ ID NO:86;
(k) SEQ ID NO:76, SEQ ID NO:87; or
(l) SEQ ID NO:73, SEQ ID NO:88

These findings demonstrate that the method of the present invention is highly useful in that it provides not only an antibody capable of exhibiting neutralizing activity over a broader range than by conventional methods, i.e., beyond the barrier of the groups, but also an antibody with higher neutralizing activity than by conventional methods.

Because of the broadness of its neutralizing activity, the influenza virus neutralizing antibody obtained by the method of the present invention is thought to recognize a site different from epitopes recognized by conventional neutralizing antibodies. If the epitope recognized by the neutralizing antibody of the present invention is clarified, a peptide comprising the amino acid sequence of the epitope (antigenic amino acid sequence) would be useful as a vaccine for influenza virus, and a nucleic acid (gene) comprising the base sequence that encodes the antigenic peptide would be useful as an influenza testing reagent and testing reagent kit. An immunologically reactive epitope can be identified using a publicly known method; examples include 1) a method wherein reactivity between a limiting degradation product prepared by enzymatically or chemically treating hemagglutinin and a neutralizing type IgG antibody acquired in the present invention is examined, 2) a method wherein the reactivity between an overlap peptide synthesized with reference to an amino acid sequence database and a type IgG neutralizing antibody acquired in the present invention is examined, and the like.

Hemagglutinin undergoes glycosylation as a precursor after transcription and translation; glycosylated hemagglutinin is known to be cleaved into the two subunits HA1 and HA2. Table 1 shows the correspondences between the amino acid sequences and sequence identification numbers of the HA1 and HA2 subunits of various influenza viruses.

TABLE 1

| | | HA1 | HA2 |
|---|---|---|---|
| H3N2 | A/Aichi/2/68 | SEQ ID NO: 28 | SEQ ID NO: 29 |
| | A/Fukuoka/1/70 | SEQ ID NO: 30 | SEQ ID NO: 31 |
| | A/Tokyo/6/73 | SEQ ID NO: 32 | SEQ ID NO: 33 |
| | A/Yamanashi/2/77 | SEQ ID NO: 34 | SEQ ID NO: 35 |
| | A/Niigata/102/81 | SEQ ID NO: 36 | SEQ ID NO: 37 |
| | A/Fukuoka/C29/85 | SEQ ID NO: 38 | SEQ ID NO: 39 |
| | A/Guizhou/54/89 | SEQ ID NO: 40 | — |
| | A/Kitakyushu/159/93 | SEQ ID NO: 41 | — |
| | A/Sydney/5/97 | SEQ ID NO: 42 | SEQ ID NO: 43 |
| | A/Panama/2007/99 | SEQ ID NO: 44 | SEQ ID NO: 45 |
| | A/Wyoming/3/2003 | SEQ ID NO: 46 | SEQ ID NO: 47 |
| | A/New York/55/2004 | SEQ ID NO: 48 | SEQ ID NO: 49 |
| H3N8 | A/Wedge/Tailed/1977 | SEQ ID NO: 50 | SEQ ID NO: 51 |
| H1N1 | A/New Caledonia/20/99 | SEQ ID NO: 52 | SEQ ID NO: 53 |
| | A/Suita/1/2009 | SEQ ID NO: 54 | SEQ ID NO: 55 |

TABLE 1-continued

| | | HA1 | HA2 |
|---|---|---|---|
| | A/Swine/Hokkaido/2/1981 | SEQ ID NO: 56 | SEQ ID NO: 57 |
| H2N2 | A/Japan/305/1957 | SEQ ID NO: 58 | SEQ ID NO: 59 |
| | A/Duck/HK/273/1978 | SEQ ID NO: 60 | SEQ ID NO: 61 |
| H5N2 | A/Duck/Mongolia/54/2001 | SEQ ID NO: 62 | SEQ ID NO: 63 |
| H5N1 | A/Vietnam/1194/2004 | SEQ ID NO: 64 | SEQ ID NO: 65 |
| | A/Anhui/1/2005 | SEQ ID NO: 66 | SEQ ID NO: 67 |
| | A/Indonesia/5/2005 | SEQ ID NO: 68 | SEQ ID NO: 69 |

The antibodies identified by the three groups, reported to be reactive to subtypes H1 and H5 share the feature of utilizing VH1-69 in the heavy-chain variable domain with the antibody of the present invention; it was suggested that they may share an epitope. Hence, it was predicted that the epitope is present in the HA2 subunit (a region involved in membrane fusion). However, unexpectedly, the present inventors demonstrated that the neutralizing antibody of the present invention does not compete with an antibody (C179) that competes for an epitope with the above-described reported antibodies (Nature Structural & Molecular Biology, Vol. 16, pp. 265-273, 2009). This supports the fact that even when utilizing VH1-69 in common, the antibodies do not share an epitope. Furthermore, the neutralizing antibody of the present invention exhibits hemagglutination inhibition (HI) activity, suggesting that it recognizes and binds to the HA1 subunit (cell receptor-binding region).

The isoleucine (the 54th amino acid in the amino acid sequence of SEQ ID NO:27) and phenylalanine (the 55th amino acid in the amino acid sequence of SEQ ID NO:27) present in the CDR2 region of VH1-69 are continuous hydrophobic amino acid residues known to form a hydrophobic tip and interact with hydrophobic clusters. The neutralizing antibody of the present invention has the aforementioned isoleucine substituted by phenylalanine, and is suggested to have some influence on the bindability to hydrophobic clusters. Hemagglutinin contains a hydrophobic pocket with highly conserved amino acids, i.e., a sialic acid binding site, which site is listed as an epitope candidate (Nature, Vol. 333, pp. 426-431, 1988). Amino acids that form such a sialic acid binding site include, for example, the 98th tyrosine, 153rd tryptophan, 155th threonine, 183rd histidine, 190th glutamic acid, 194th lysine, 134th-138th amino acids, and 224th-228th amino acids of A/Aichi/2/68 influenza virus HA1 and the like (in the case of an influenza virus of a different subtype or strain, corresponding amino acids). Therefore, a region comprising these amino acids is possibly the epitope. Influenza virus HA1 has been reported to contain five sites where mutations are likely to accumulate [A, B (B1, B2), C (C1, C2), D, and E regions] (P. A. Underwood, J. Gen. Virol. vol. 62, 153-169, 1982; Wiley et al., Nature, vol. 289, 366-378, 1981). In the present invention, region A refers to the 121st-146th amino acids in SEQ ID NO:28 or a region corresponding to the amino acid region; region B1 refers to the 155th-163rd amino acids in SEQ ID NO:28 or a region corresponding to the amino acid region; region B2 refers to the 155th-163rd amino acids in SEQ ID NO:28 or a region corresponding to the amino acid region; region C1 refers to the 50th-57th amino acids in SEQ ID NO:28 or a region corresponding to the amino acid region; region C2 refers to the 275th-279th amino acids in SEQ ID NO:28 or a region corresponding to the amino acid region; region D refers to the 207th-229th amino acids in SEQ ID NO:28 or a region corresponding to the amino acid region; region E refers to the 62nd-83rd amino acids in SEQ ID NO:28 or a region corresponding to the amino acid region. Because kinds of the antibody of the present invention, particularly F045-092, competed with antibodies that recognize the vicinities of region A, region B1, and region B2 that are present in HAL it is suggested that the vicinities of regions A and B are the epitope.

Because the neutralizing antibody of the present invention is capable of neutralizing all hemagglutinin subtypes of influenza viruses beyond the barrier of the groups, it can be an effective prophylactic and/or therapeutic means not only for seasonal influenza caused by an antigenic drift, but also for pandemics due to an antigenic shift. Hence, by administering the neutralizing antibody, passive immunization against all subtypes of influenza viruses can be performed, which offers expectations for therapeutic effects on patients who have contracted influenza due to any influenza virus, and prophylactic effects on subjects who are feared to contract, or to be infected, with influenza virus. Additionally, the neutralizing antibody of the present invention is thought to be very unlikely to produce adverse reactions because it is an antibody already present in the human body.

The neutralizing antibody of the present invention can be used as a passive immunotherapeutic agent for influenza as it is per se, or after being prepared as a pharmaceutical composition by blending with a pharmacologically acceptable carrier.

Here, as the pharmacologically acceptable carrier, various organic or inorganic carrier substances in common use as pharmaceutical materials can be used, which are formulated as excipients, solvents (dispersing agents), solubilizers, suspending agents, stabilizers, isotonizing agents, buffers, pH regulators, soothing agents and the like. Pharmaceutical additives such as preservatives and antioxidants can also be used as necessary.

Examples of suitable excipients include lactose, sucrose, D-mannitol, D-sorbitol, starch, α starch, dextrin, crystalline cellulose, low-substitutional hydroxypropylcellulose, carboxymethylcellulose sodium, gum arabic, pullulan, light silicic anhydride, synthetic aluminum silicate, magnesium metasilicoaluminate and the like.

Examples of suitable solvents include water for injection, physiological saline, Ringer's solution, alcohols, propylene glycol, polyethylene glycol, sesame oil, corn oil, olive oil, cottonseed oil and the like.

Examples of suitable solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Examples of suitable suspending agents include surfactants such as stearyltriethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose; polysorbates, polyoxyethylene hardened castor oil and the like.

Examples of suitable stabilizers include human serum albumin (HSA), sodium pyrosulfite, Rongalite, sodium hydrogen metasulfite and the like.

Examples of suitable isotonizing agents include sodium chloride, glycerin, D-mannitol, D-sorbitol, glucose and the like.

Examples of suitable buffers include buffer solutions such as of phosphates, acetates, carbonates and citrates, and the like.

Examples of suitable pH regulators include acids or bases, such as hydrochloric acid and sodium hydroxide.

Examples of suitable soothing agents include benzyl alcohol and the like.

Examples of suitable preservatives include para-oxybenzoic acid esters, chlorobutanol, benzyl alcohol, phenethyl alcohol, dehydroacetic acid, sorbic acid and the like.

Examples of suitable antioxidants include sulfites, ascorbates and the like.

Examples of dosage forms for the aforementioned pharmaceutical composition include injectable preparations such as injections (e.g., subcutaneous injections, intravenous injections, intramuscular injections, intraperitoneal injections, intra-arterial injections and the like), drip infusions and the like.

These pharmaceutical compositions can be produced by methods in common use in the field of drug formulation technology, for example, methods described in the Japanese Pharmacopoeia and the like. Specific methods of preparing pharmaceutical preparations are described in detail below. The antibody content in the pharmaceutical composition varies depending on the dosage form, dose and the like, and is, for example, about 0.1% to 100% by weight.

For example, an injection is produced by dissolving, suspending or emulsifying the antibody, along with a dispersing agent (e.g., polysorbate 80, polyoxyethylene hydrogenated castor oil 60, polyethylene glycol, carboxymethylcellulose, sodium alginate and the like), a preservative (e.g., methylparaben, propylparaben, benzyl alcohol, chlorobutanol, phenol and the like), an isotonizing agent (e.g., sodium chloride, glycerin, D-mannitol, D-sorbitol, glucose and the like) and the like, in an aqueous solvent (e.g., distilled water, physiological saline, Ringer's solution and the like) or an oily solvent (e.g., vegetable oils such as olive oil, sesame oil, cottonseed oil and corn oil, propylene glycol and the like). If desired, additives such as a solubilizer (e.g., sodium salicylate, sodium acetate and the like), a stabilizer (e.g., human serum albumin and the like), and a soothing agent (e.g., benzyl alcohol and the like) may be used. The injection liquid may be subjected to a sterilizing treatment such as filtration sterilization using a membrane filter and the like as required, and is usually filled in an appropriate container such as an ampoule.

The injection can also be used as a fresh supply obtained by dissolving (dispersing) a powder prepared by treating the above-described liquid by vacuum drying and the like. Examples of methods of vacuum drying include lyophilization and a method using the Speedback Concentrator (SAVANT Company). When performing lyophilization, it is preferable to lyophilize the sample, cooled below −10° C., using a flask in the laboratory or a tray or vial in industrial settings. When the Speedback Concentrator is used, lyophilization is performed at about 0 to 30° C. under a vacuum of about 20 mmHg or less, preferably about 10 mmHg or less. It is preferable to add a buffering agent such as a phosphate to the liquid to be dried, to obtain a pH of about 3 to 10. The powder preparation obtained by lyophilization, as a long-stable preparation, can be prepared freshly as an injection by dissolving in water for injection, physiological saline, Ringer's solution and the like, or by dispersing in olive oil, sesame oil, cottonseed oil, corn oil, propylene glycol and the like before use.

As required, the above-described antibody may be used in combination with another therapeutic drug. Examples of therapeutic agents include Tamiflu, Relenza, amantadine and the like.

Alternatively, as required, the above-described antibody may be coupled with another therapeutic drug. The antibody transports the drug to a site where influenza virus is present or the vicinity thereof, and inhibits the entry of the virus into cells, whereas the drug kills the virus or treats, mitigates or ameliorates symptoms of influenza. Examples of the drug include all drugs that is, or will be, in use as therapeutic drugs for influenza. Such drugs are, for example, synthetic or naturally occurring, low-molecular-weight or high-molecular-weight, proteinous, non-proteinous, nucleic acidic or nucleotidic substances. Coupling of the antibody and the drug is preferably performed via a linker. The linker is exemplified by one comprising a substituted or unsubstituted aliphatic alkylene chain, and having at both ends thereof a group bindable to a functional group of the antibody or drug, for example, an N-hydroxysuccinimide group, an ester group, a thiol group, an imidocarbonate group, an aldehyde group or the like (Koutai Kogaku Nyumon, Chijin Shokan, 1994).

The antibody can also be enclosed in a liposome to facilitate the delivery of a pharmaceutical into cells as required. Preferable liposomes include positively charged liposomes, positively charged cholesterols, transmembrane peptide binding liposomes and the like (Mamoru Nakanishi et al., Protein, Nucleic Acid and Enzyme, 44: 1590-1596 (1999), Shiroh Futaki, Kagaku To Seibutsu, 43: 649-653 (2005), Clinical Cancer Research 59: 4325-4333 (1999) and the like).

The neutralizing antibody of the present invention is administered via non-oral routes, for example, intravenous, intraperitoneal, intramuscular, subcutaneous, transdermal administration and the like. The active ingredient antibody content is exemplified by, but is not limited to, 100 to 2,500 µg/mL per dose, or 1.0 to 10 mg per kg body weight for an adult human patient. Frequency of dosing is, for example, once per 1 to 2 weeks in one to several times of administration or once per 2 to 3 weeks for about 2 months.

The neutralizing antibody of the present invention can be used not only for prophylaxis and/or treatment of human influenza, but also for prophylaxis and/or treatment of influenza in birds such as chicken and non-human mammals such as pigs and horses animals by administration to these animals, whereby the risk of human infection can be reduced in advance. When the neutralizing antibody of the present invention is applied to these animals, the same techniques of preparing pharmaceutical preparations as the above can be used.

The neutralizing antibody of the present invention has been isolated by screening antibodies that are originally present in the human body. It is reasonable to think that such antibodies are already carried by humans at some frequencies, rather than occurring extremely rarely. Therefore, individuals capable of producing the neutralizing antibody of the present invention are thought to be also resistant to new types of influenza. Meanwhile, individuals lacking the capability of producing such antibodies can be said to be threatened by possible infection with new types of influenza. Provided that whether the neutralizing antibody is carried can be determined by relatively convenient procedures, it can be judged that preventive measures by passive immunization are desirably taken preferentially for non-carriers of the neutralizing antibody.

Accordingly, the present invention also provides a method of detecting the neutralizing antibody of the present invention in a subject, comprising the steps of:
(1) inoculating hemagglutinin of a any one of subtypes H1 to H16 to the subject,
(2) collecting blood from the subject at the time when antibody-producing cells have been sufficiently proliferated after inoculation, and
(3) examining the blood for the presence of absence of antibody-producing cells that present an antibody that binds to both hemagglutinin of a subtype selected from Group 1 and hemagglutinin of a subtype selected from Group 2, and that has a heavy-chain variable domain V region encoded by the VH1-69 or VH1-e gene, or
a method comprising the steps of:
(1) inoculating hemagglutinin of a subtype selected from Group 1 and hemagglutinin of a subtype selected from Group 2 separately to the subject,
(2) collecting blood from the subject at the time when antibody-producing cells have been sufficiently proliferated after inoculation of each subtype of hemagglutinin, and
(3) examining the blood for the presence or absence of antibody-producing cells that present an antibody that binds to hemagglutinin of a subtype selected from a group different from the group to which the inoculated hemagglutinin belongs, and that has a heavy-chain variable domain V region encoded by the VH1-69 or VH1-e gene.

The desired neutralizing antibody cannot be detected in a small amount of blood drawn unless B lymphocytes that produce the desired antibody are proliferated and concentrated. Hence, the present invention is intended to detect the presence or absence of the neutralizing antibody of the present invention by induction of hemagglutinin inoculation using as the indexes the binding activity for hemagglutinin belonging to a different group, and the utilization of a V gene fragment shared by the majority of kinds of the neutralizing antibody of the present invention.

The present invention is explained in more detail in the following by referring to Examples, which are mere exemplifications and do not at all limit the present invention.

EXAMPLES

Blood Sampling

An amount of mononuclear cells equivalent to 3 L of blood was collected by apheresis from a pediatrician born in 1974. Blood sampling was performed in May 2004.

Preparation of Human Phage Antibody Library

A human phage antibody library was prepared by the phage display method. Approximately $10^9$ lymphocytes were recovered from the blood component obtained by the blood sampling with Ficoll-Paque, and RNAs were isolated. cDNAs were amplified from the RNAs to construct libraries of antibody Heavy chains (VHs) and Light chains (VLs), respectively. The clone numbers of Heavy chains and Light chains were about $10^9$ and $10^6$, respectively. Then, Heavy chains and Light chains were combined to construct a human phage antibody library of Fab-cp3 type, which was a library including about $10^{10}$ clones.

Influenza Virus Strains Used

The following influenza virus strains were used in this Example. Unless otherwise noted, abbreviations in the subsequent Examples indicate the following influenza virus strains.

(H3N2 Type)
Aic68: A/Aichi/2/68, Fuk70: A/Fukuoka/1/70, Tok73: A/Tokyo/6/73, Yam77:
A/Yamanashi/2/77, Nii81: A/Niigata/102/81, Fuk85: A/Fukuoka/C29/85, Gui89:
A/Guizhou/54/89, Kit93: A/Kitakyushu/159/93, Syd97: A/Sydney/5/97, Pan99:
A/Panama/2007/99, Wyo03: A/Wyoming/3/2003, NY04: A/New York/55/2004
(H1N1 Type)
NC99: A/New Caledonia/20/99, S106: A/Solomon Island/3/2006

Screening

Screening was performed by the Panning method. An influenza virus strain inactivated by formalin treatment was coated onto an immunotube, and antigen-antibody reaction was subsequently performed between the virus strain coated in the tube and the phage antibody library. After the tube was washed with PBS, phages bonded to the antigen were eluted with acid, then immediately neutralized, and recovered. The recovered phages were infected to *Escherichia coli*, recovery rate was calculated, and phage antibodies were prepared. Using the phages, the above-mentioned operations were repeated. These operations were performed three times, and eluted phages were infected to *Escherichia coli*, which was then cultured overnight on an LBGA plate to give single colonies. These colonies were isolated to prepare Fab-cp3 antibodies, whose binding activity against the virus strain used for the screening was confirmed by the ELISA. Using clones showing the binding activity as positive clones, further analysis was performed.

Preparation of Fab-Cp3 Type Antibodies

The *Escherichia coli* infected with the phage obtained in the screening was inoculated into YT supplemented with 0.05% glucose, 100 µg/ml ampicillin and 1 mM IPTG, and shaking cultured at 30° C. overnight. Culture supernatant containing a Fab-cp3 type antibody secreted by the *Escherichia coli* was recovered by the centrifugation, and used for experiments including ELISA, competition ELISA, Western blotting, flow cytometer and the like.

ELISA

A solution of virus strain inactivated by formalin treatment was added to 96-well Maxisorp, which was coated at 37° C. for 1 hr. The virus solution was removed from the well, and 5% BSA/PBS was added to perform blocking for 1 hr. After removing the BSA solution, the *Escherichia coli* culture supernatant containing a Fab-cp3 type antibody was added and allowed to react for 1 hr. After washed with PBS (PBST) supplemented with 0.05% Tween 20, a rabbit anti-cp3 antibody was added and allowed to react for 1 hr. After further washing with PBST, a goat anti-rabbit IgG(H+L)-HRP was added and allowed to react for 1 hr. After washed with PBST, a solution of OPD, which is a substrate of HRP, was added and allowed to react at room temperature, the reaction was then quenched by 2N sulfuric acid, after which OD was measured at a wavelength of 492 nM. Unless otherwise stated, all reactions were performed at 37° C.

Sequence Analysis of Isolated Antibody Clones

The base sequences of Heavy chain (VH) and Light chain (VL) of clones positive to the virus antigen were confirmed by a sequencing reaction.

Grouping of Isolated Clones

After the VH base sequences of clones were confirmed, the sequences were converted to amino acid sequences, which were compared among the isolated clones. Focusing on similarity of VH amino acid sequences, especially similarity in CDR3 sequences, the clones were grouped.

Western Blotting

Formalin-treated virus strain was subjected to SDS-PAGE under a nonreducing condition to be fractionated, and transferred onto a PVDF membrane. The PVDF membrane was blocked with PBST supplemented with 2.5% skim milk for 1 hr, then washed with PBST, and subjected to a reaction with Fab-cp3 type antibody in the culture supernatant for 1 hr. After washed with PBST, the membrane was subjected to a reaction with a rabbit anti-cp3 antibody for 1 hr, further washed with PBST, and then subjected to a reaction with a goat anti-rabbit IgG(H+L)-HRP for 1 hr. After washed with PBST, the membrane was reacted with ECL solution for 4-5 minutes, and bands were detected with a CCD camera. All reactions were performed at room temperature.

Preparation of Fab-Pp Type Antibodies

Plasmid DNAs of Fab-cp3 type antibody clones were genetically engineered to convert into those of Fab-pp type (PP is an Fc-binding domain of protein A), with which *Escherichia coli* was transformed. The *Escherichia coli* was inoculated into YT supplemented with 0.05% glucose, 100 µg/ml ampicillin and 1 mM IPTG, and shaking cultured at 30° C. overnight. Culture supernatant containing a Fab-pp type antibody secreted by the *Escherichia coli* was recovered by the centrifugation, and after ammonium sulfate precipitation, dissolved in PBS, purified with IgG-Sepharose column, and used for experiments including HI activity, virus neutralization activity and the like.

HI Activity Measurement

Purified Fab-pp type antibodies were serially diluted with PBS, each mixed with a 4 HA unit/well virus solution, and allowed to react at room temperature for 1 hr. Red blood cells were added and mixed, and allowed to react at room temperature for 30 min to 1 hr. The results were shown with the dilution ratio of the antibodies.

Figures 1, 22:
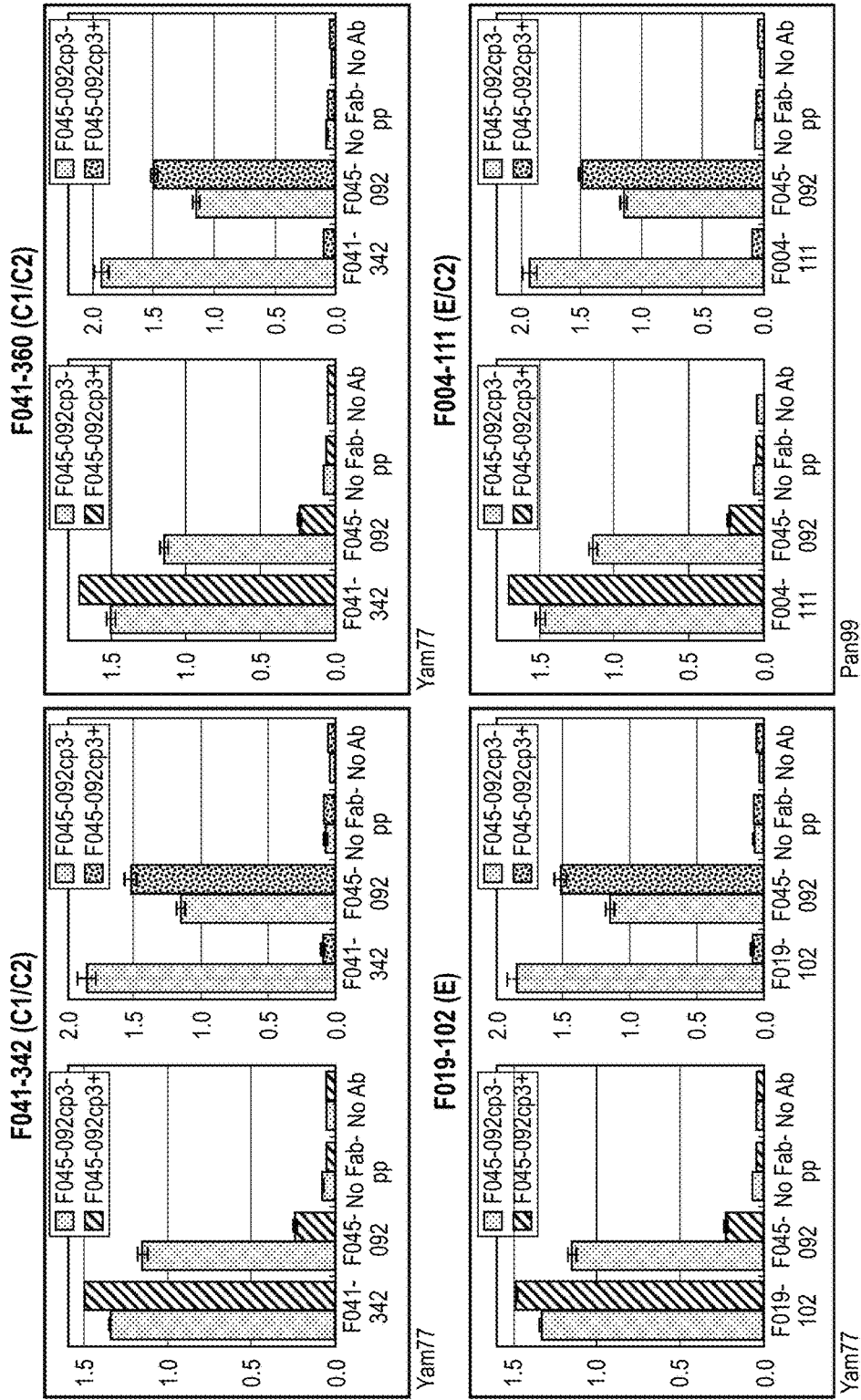

Binding Activities of Clones Isolated from N Library Against H3N2 Influenza Virus Strains Binding activities of the antibody clones isolated from the N library screening against any of 12 kinds of H3N2 virus strains and an H1N1 virus strain used in the screening are shown as results of ELISA. These are experiments for confirming what cross reactivity the clones isolated in the screening show against the virus strains. The results are shown in FIG. 1.

The isolated clones are classified into groups according to the degree of binding activity against respective viruses, and group numbers are indicated on the leftmost column. The column "Number isolated" next to "Clone name" on the right is the number of clones showing identical VH amino acid sequence out of clones isolated in the screening, and "Isolated virus strain" further next thereto on the right indicates the screening with which virus strain the clone was isolated.

Numerical values from ELISA have been processed as follows:
not less than 1: red
not less than 0.5 and less than 1: orange
not less than 0.1 and less than 0.5: yellow
less than 0.1: white The Western Blotting (WB) column on the extreme right shows results only on clones for which experiments were performed. Clones for which a band was detectable in the position of HA are indicated as "HA", and clones for which a band was detected in other position are indicated as "?", since what they recognize is currently unknown. Blanks indicate no experiments performed.

Results of N Library Screening

Figures 2, 22:
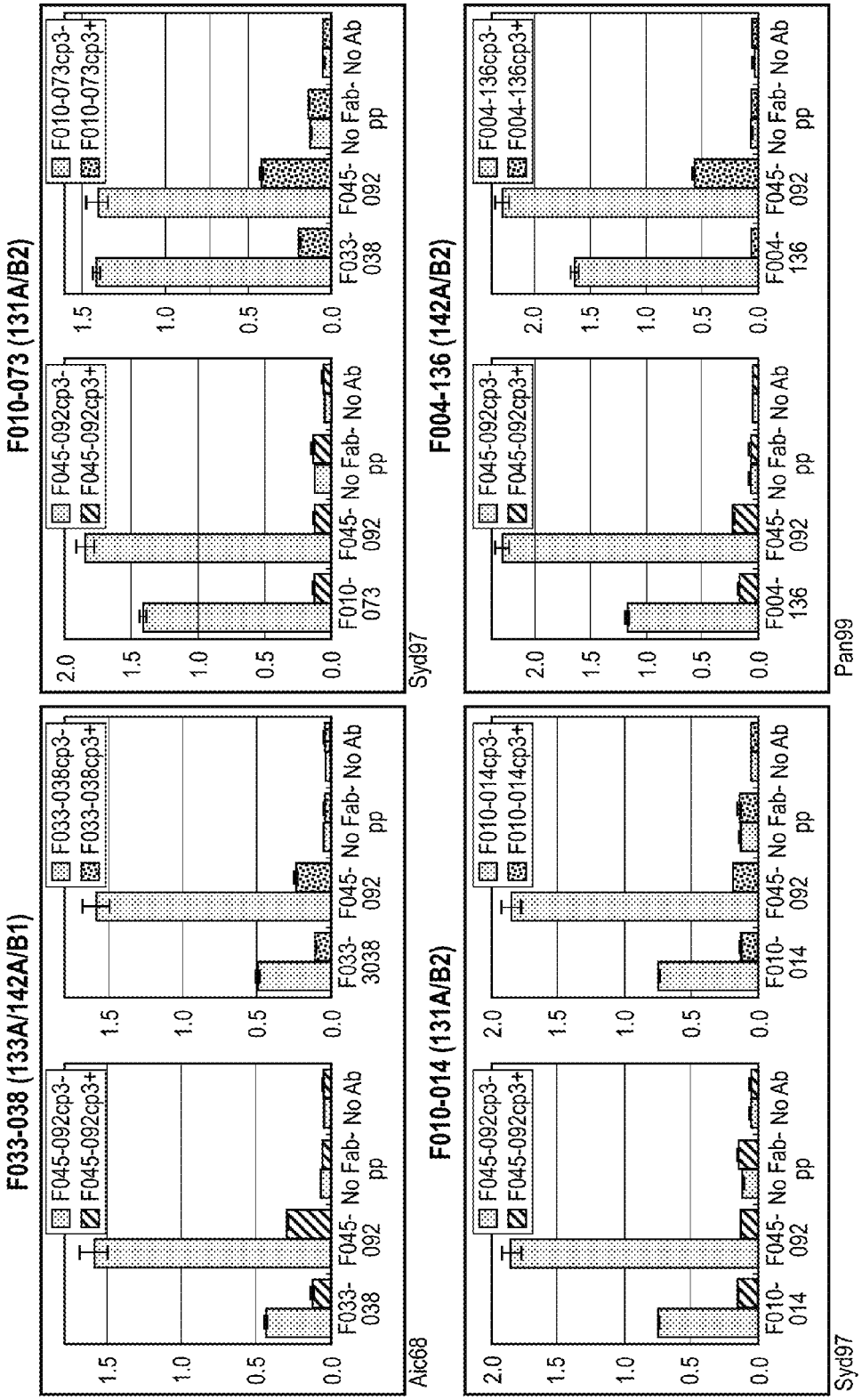

The number of clones picked up in each screening of H3N2 strain (before confirmation by ELISA), and from among them, the screening with which virus strain the clones classified as Group 11 and Group 22 (FIG. 1) were isolated, are shown (FIG. 2).

Group 11 is the group of antibody clones that recognize both of H3 and H1 strains as antigens, and Group 22 is the group of antibody clones that recognize any of 12 kinds of H3 strains, but do not recognize H1 strains.

Status of Isolation of Clones Belonging to Group 11

Figures 3, 22:
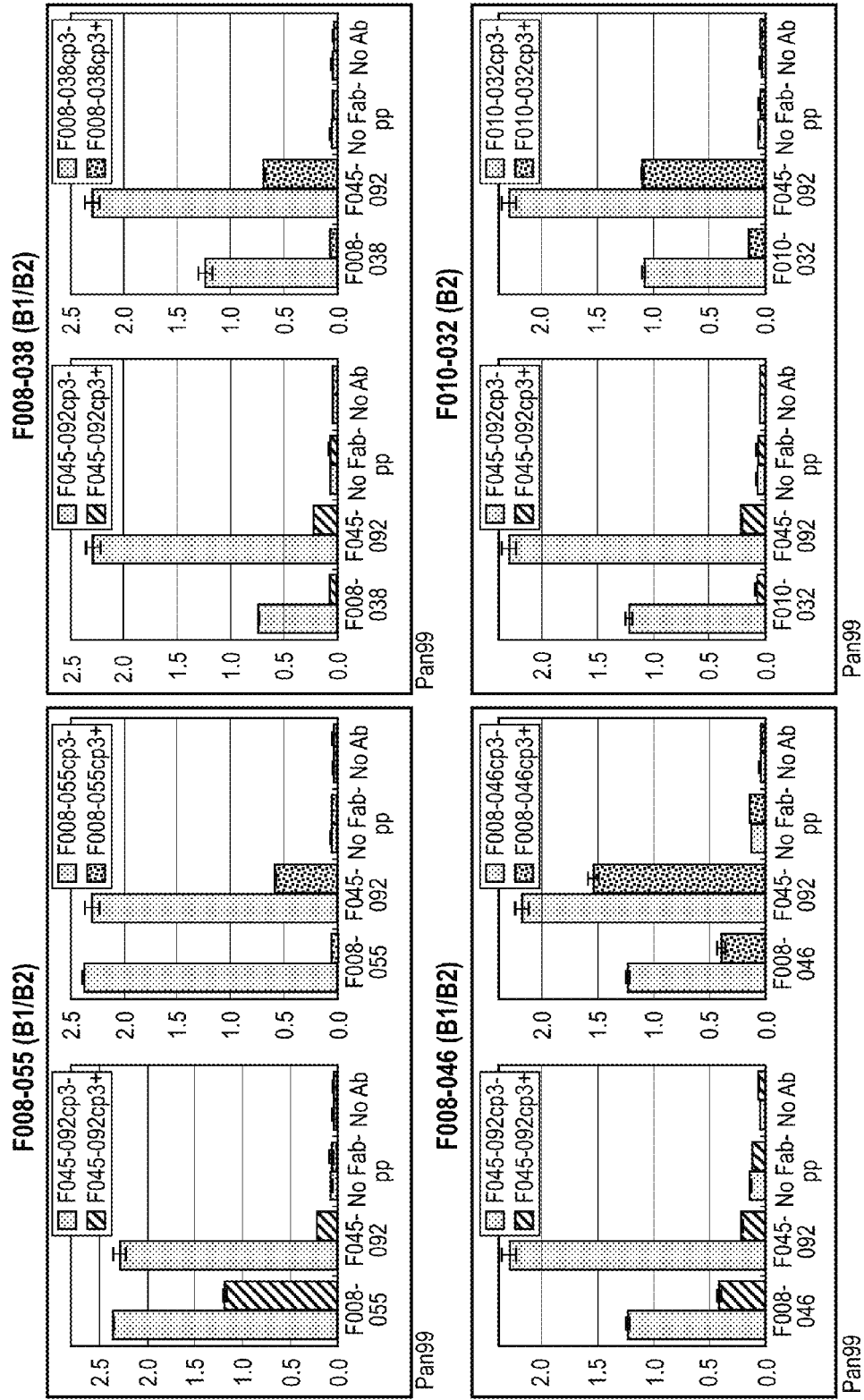

Screening virus strains with which respective antibody clones classified as Group 11 were isolated, and the isolated number on the screening are shown (FIG. 3).

Based on VH sequence of each clone (VL sequence is not taken into consideration), the number of isolated clones having identical VH sequence are shown.

Amino Acid Sequences of Clones Belonging to Group 11

Figures 4, 22:
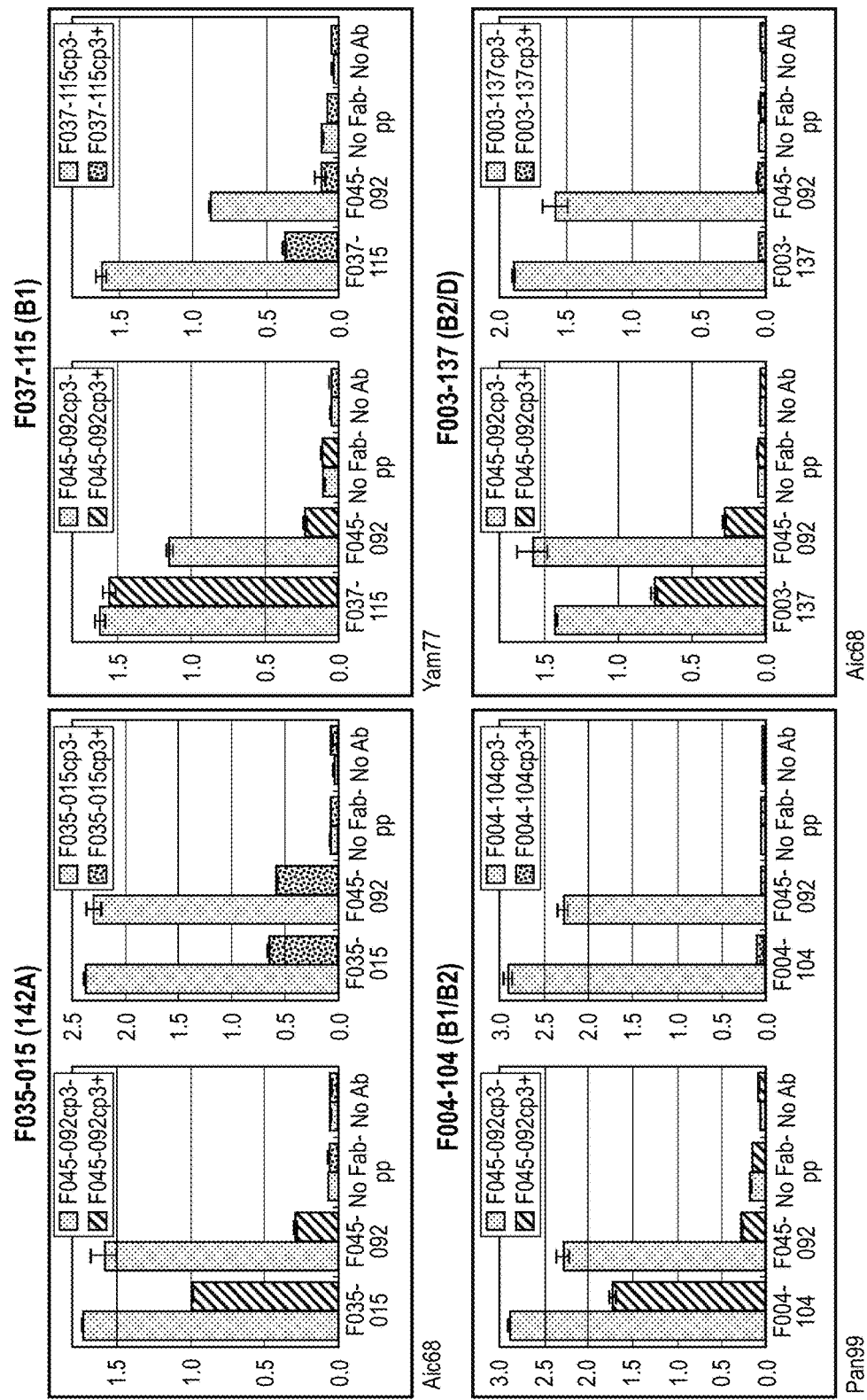

Amino acid sequences of VH and VL of clones classified as Group 11 are shown (FIG. 4).

(1) VH Amino Acid Sequence

The clones belonging to Group 11 were found to have the highest identity with IGHV1-69*01 according to searches for germline with IgBlast of NCBI. Therefore, IGHV1-69*01 were judged as the germline.

From the result, comparisons of VH amino acid sequences were performed between IGHV1-69*01 and the respective clones. "Identity (%) with Germline FR1-FR3" is calculation of identity with the amino acid sequences of FR1 to FR3 of IGHV1-69*01. Parts with different amino acids, as a result of comparison with the amino acid sequence of IGHV1-69*01, are highlighted with a changed color. However, as to CDR3 and FR4, amino acids different among each sequence of the clones are highlighted with changed colors.

(2) VL Amino Acid Sequence

Fifteen clones with the VH amino acid sequence identical with that of F022-360 have been isolated so far. The VL sequences of 12 clones out of these were subjected to sequence analysis, resulting in identification of 7 kinds of VLs. As a result, it was found that the VH sequence possessed by F022-360 has 7 kinds of VH-VL combinations. Of the 7 kinds, the VL sequence highlighted with gray is the combination of F022-360. For clones with other VH sequences, the VL sequence of only the indicated clone has been confirmed, and therefore only the one kind of combination has been confirmed so far. The VL sequence of F026-245 has not been confirmed.

The germline for the amino acid sequence of each VL was determined as one with the highest identity according to searches with IgBlast of NCBI, like for VHs. Since some, 3 kinds of germlines were detected, each sequence of the clones was compared against IGLV1-44*01. Different amino acids are highlighted with a changed color.

Comparison of VH Amino Acid Sequences Between Previously Reported Clones that Neutralize H1 and H5 and are Antibodies Whose Germline is 1-69, and Clones Belonging to Group 11

Figures 5, 22:
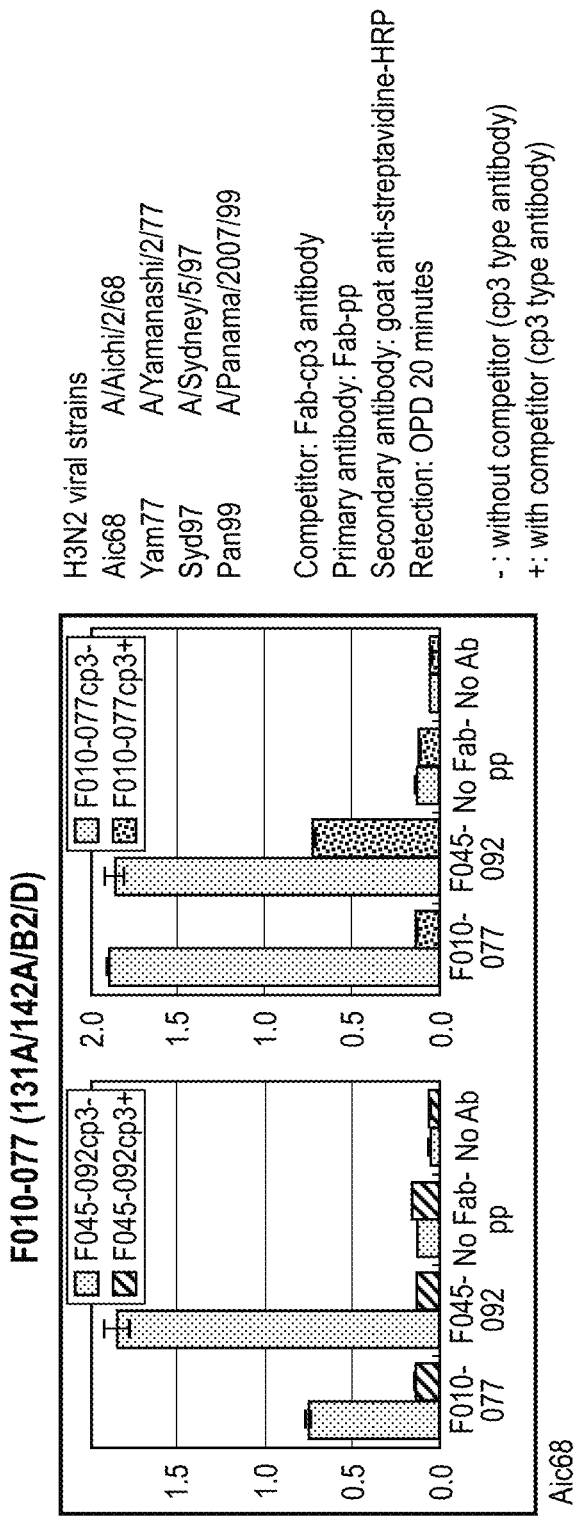

Human antibodies that neutralize both of H1 and H5 strains had been previously reported in 3 articles (exactly, 4 articles), the germline of any of which clones is IGHV1-69. Thus, comparison of amino acid sequences were performed between these clones, and the germline IGHV1-69*01 or the clones classified as Group 11 (FIG. 5).

Amino acids identical with those in IGHV1-69*01 are shown with bars.

Volumes and pages of each of the articles are as follows:
2009 Nat. Struct. Mol. Biol.: Vol. 16 265-273
2009 Science: Vol. 324 246-251 (2008 PLoS One: Vol. 3 e3942 is the article related to isolation of the clone.)
2008 PNAS: Vol. 105 5986-5991

Binding Activities of Clones Belonging to Group 11 Against H3N2 Influenza Virus Strains The binding activities of the clones belonging to Group 11 against 12 kinds of H3 strains and an H1 strain used in the screening were confirmed by the ELISA. Assays for each virus strain were performed in duplicate, and the mean value and standard deviation were calculated (FIG. 6).

Western Blotting of Clones Belonging to Group 11

Figure 7:
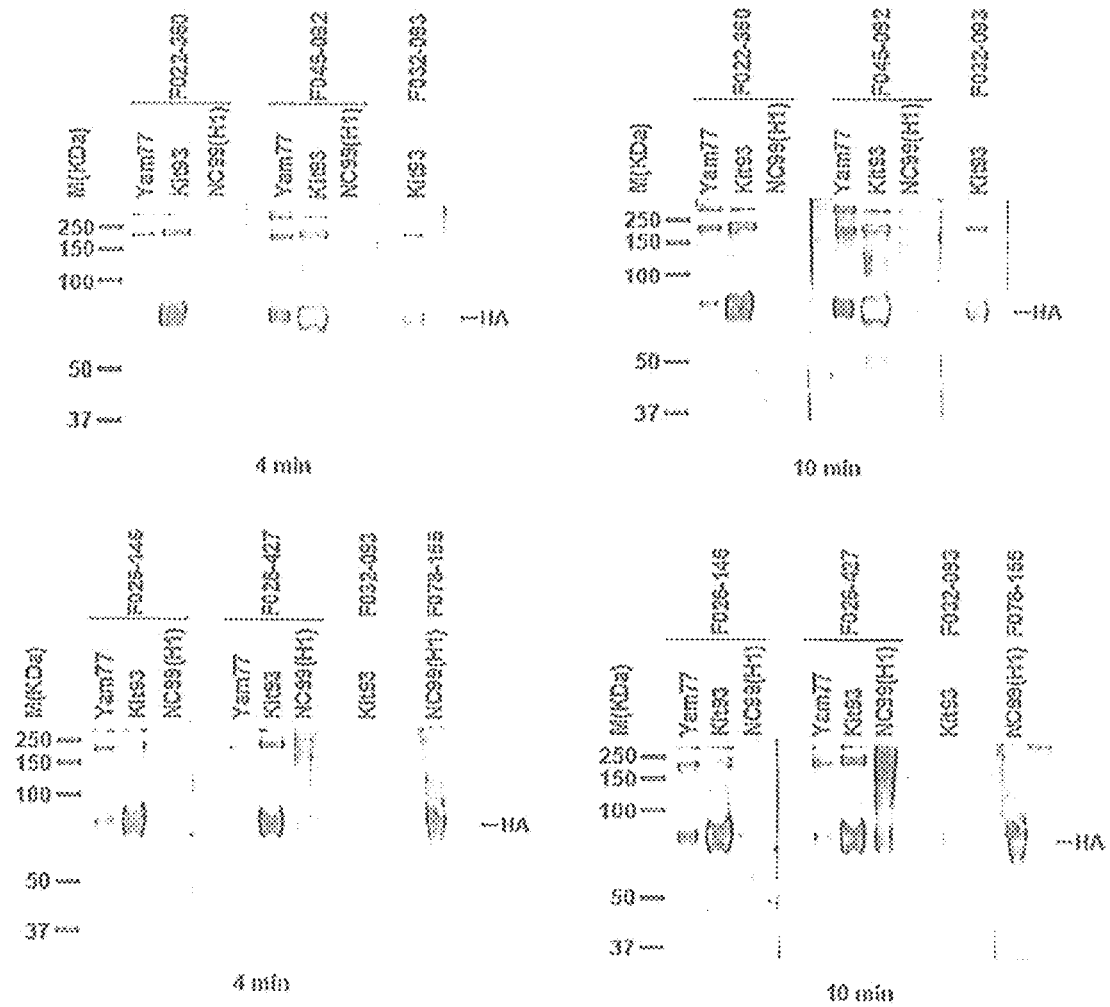
FIG. 7 presents Western blot diagrams showing that clones classified under Group.11 recognize the HAs of both H3 and H1 strains.
Figure 11:
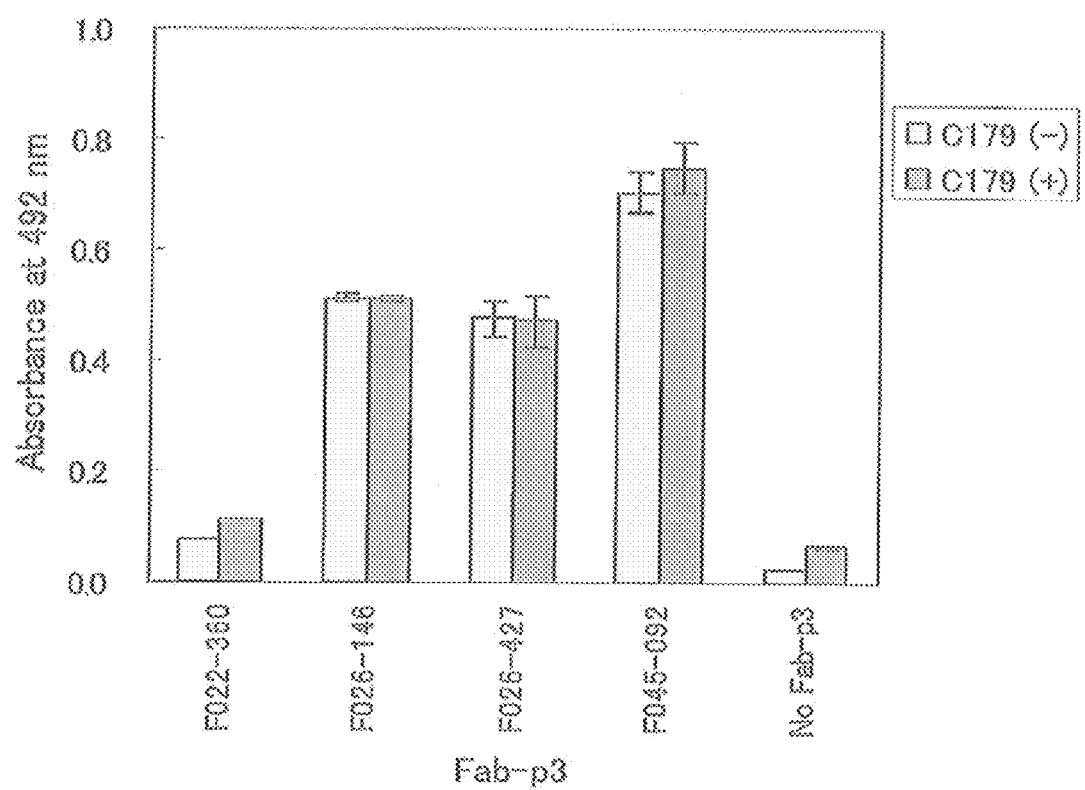
FIG. 11 shows the results of an ELISA determination of whether the mouse monoclonal antibody C179 competitively inhibits the binding activities of clones classified under Group.11 for subtype H3 influenza viruses. ELISA was performed to determine the actions of Fab-p3 antibodies (F022-360, F026-146, F026-427, F045-092) on the influenza A/USSR New Caledonia strain in the presence (C179 (+)) and absence (C179 (−)) of C179.

These are experiments illustrating that the clones belonging to Group 11 recognize HAs of both of H3 and H1 strains (FIG. 7).

All samples were subjected to SDS-PAGE under nonreducing conditions.

Shown in the upper half of FIG. 7 are datas on F022-360 and F045-092, and the datas in the lower half of FIG. 7 are on F026-146 and F026-427. The difference between left and right is of exposure time for data capture.

F032-093 is a positive control for HA of H3 strain A/kitakyushu/159/93, and F078-155 is a positive control for HA of H1 strain A/New Caledonia/20/99.

HI Activities of Clones Belonging to Group 11

Confirmation of whether the clones classified as Group 11 have HI activities was performed (FIG. 8).

The HIU is shown as dilution ratio, wherein the antibodies were diluted from the concentration of 100 μg/ml in 2 fold increments.

Neutralizing Activities by Fab-Pp Type Antibodies

Confirmation of whether the clones classified as Group 11 neutralize H3 and H1 influenza virus strains (FIG. 9).

The inhibition rate of focus formation on the addition of 250 or 100 μg/ml of Fab-pp type antibodies is shown as % Inhibition.

Inhibition of ELISA Activity of C179 by Fab-p3

Mouse monoclonal antibody C179, which neutralizes New Caledonia strain of Sobiet Union type Influenza A, was reacted with an immunoplate to which a vaccine for the strain had been adsorbed, in the presence or absence of Fab-p3 antibodies (F022-360, F026-146, F026-427, F045-092, F005-126; F005-126 is a negative control unreactive with the HA of New Caledonia strain of Sobiet Union type Influenza A). Then, the immunoplate was reacted with an HRP-labeled anti-mouse IgG (manufactured by MBL), and caused to develop color by OPD to detect C179 bound to the vaccine.

No significant difference was observed in values of ELISA between in the presence and absence of Fab-p3 antibodies (F022-360, F026-146, F026-427, F045-092, F005-126)(FIG. 10). Therefore, it was found that the reactivity of C179 against the vaccine is not inhibited by F022-360, F026-146, F026-427 or F045-092. This suggests the difference of recognition epitope between C179 and F022-360, F026-146, F026-427 or F045-092.

Inhibition of ELISA Activity of Fab-p3 by C179

Fab-p3 antibodies (F022-360, F026-146, F026-427, F045-092, F005-126) were reacted with an immunoplate to which a vaccine for New Caledonia strain of Sobiet Union type influenza A had been adsorbed, in the presence or absence of C179. Then, the immunoplate was reacted with a rabbit anti-p3 polyclonal antibody, followed by a reaction with an HRP-labeled anti rabbit IgG (manufactured by MBL), and caused to develop color by OPD to detect Fab-p3 antibodies bound to the vaccine.

No significant difference was observed in values of ELISA between in the presence and absence of C179 (FIG.

11). Therefore, it was found that the reactivity of F022-360, F026-146, F026-427 or F045-092 against the vaccine is not inhibited by C179. This also suggests the difference of recognition epitope between F022-360, F026-146, F026-427 or F045-092 and C179.

Inhibition of ELISA Activity of F005-126 by Fab-p3

Fab-PP type monoclonal antibody F005-126 was reacted with an immunoplate to which a vaccine for Aichi strain of Hong Kong type influenza A had been adsorbed, in the presence or absence of Fab-p3 antibodies (F022-360, F026-146, F026-427, F045-092, F005-126, F019-102; F019-102 is a negative control unreactive with Aichi strain of Hong Kong type influenza A). Then, the immunoplate was reacted with an HRP-labeled rabbit IgG, and caused to develop color by OPD to detect Fab-PP type F005-126 bound to the vaccine.

Figure 12:
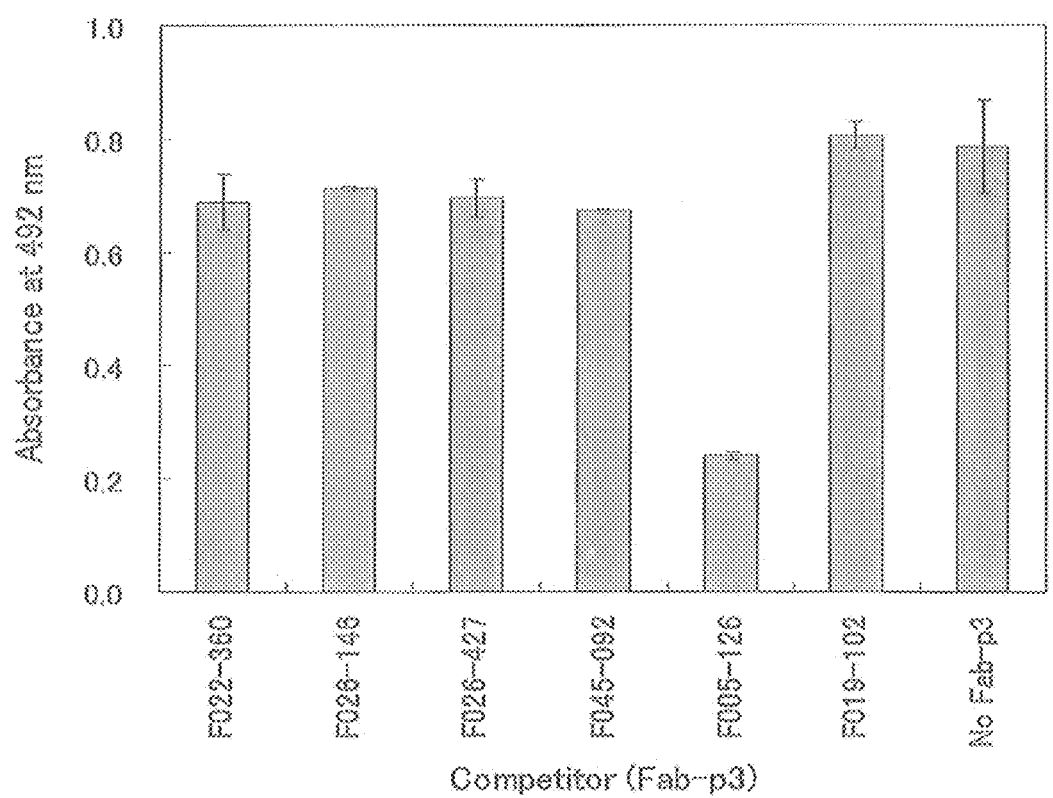
FIG. 12 shows the results of an ELISA determination of whether the antibody clone F005-126 shown in FIG. 2, which possesses a broad range of strain specificity for subtype H3 influenza viruses, and an antibody clone that recognizes both subtype H3 and subtype H1 influenza viruses classified under Group.11 share an epitope. ELISA was performed to determine the action of Fab-PP type F005-126 on the influenza A/Hong Kong Aichi strain in the presence and absence (No Fab-p3) of Fab-p3 antibodies (F022-360, F026-146, F026-427, F045-092, F005-126, F019-102), wherein Fab-p3 type F005-126 served as a positive control for competitive inhibition, and F019-102 as a negative control that does not react to the influenza A/Hong Kong Aichi strain.

F005-126 is an antibody that is not reactive with New Caledonia strain of Sobiet Union type influenza A, but widely reactive with plural strains of Hong Kong type influenza A, and neutralizes them. Because F022-360, F026-146, F026-427 and F045-092 also are widely reactive with plural strains of Hong Kong type influenza A, possible proximity of recognition epitope was conceived. For this reason, competitive inhibitory experiments with F005-126 were performed. When the reactivity of Fab-PP type F005-126 against a vaccine for Aichi strain of Hong Kong type influenza A in the presence and absence of Fab-p3 antibodies (F022-360, F026-146, F026-427, F045-092, F019-102), no significant difference in values of ELISA was observed (FIG. 12). In the presence of Fab-p3 type F005-126 as a positive control, the value of ELISA was significantly decreased. Therefore, it was found that the reactivity of F005-126 against the vaccine is not inhibited by F022-360, F026-146, F026-427 or F045-092. This suggests the difference of recognition epitope between F005-126 and F022-360, F026-146, F026-427 or F045-092.

Reactivity of F026-427 and F045-092 with HA Expressed on 293T Cells

The HA gene of Yamanashi strain of Hong Kong type influenza A was inserted into a cloning site of expression vector pNOW to prepare pNOW-Yam77HA. pNOW-Yam77HA and lipofectamine LTX were mixed, and added to 293T cells to perform transfection. After 24 hrs of cultivation, transfected cells were recovered, followed by blocking with 2.5% BSA-PBS-0.05% Na—$N_3$ at 4° C. for 30 min, and reacted with Fab-p3 antibody (F026-427, F045-092, F008-038) at 4° C. for 30 min (F008-038 is a negative control unreactive with the HA of Yamanashi strain). Then, the cells were reacted with a rabbit anti-p3 polyclonal antibody, then with an Alexa488-labeled anti-rabbit IgG (manufactured by Pierce) to perform FACS analysis. Similarly, as a positive control, the cells were reacted with Hong Kong type influenza A mouse monoclonal antibody F49, then with an Alexa488-labeled anti-mouse IgG (manufactured by Pierce) to perform FACS analysis.

Figure 13:
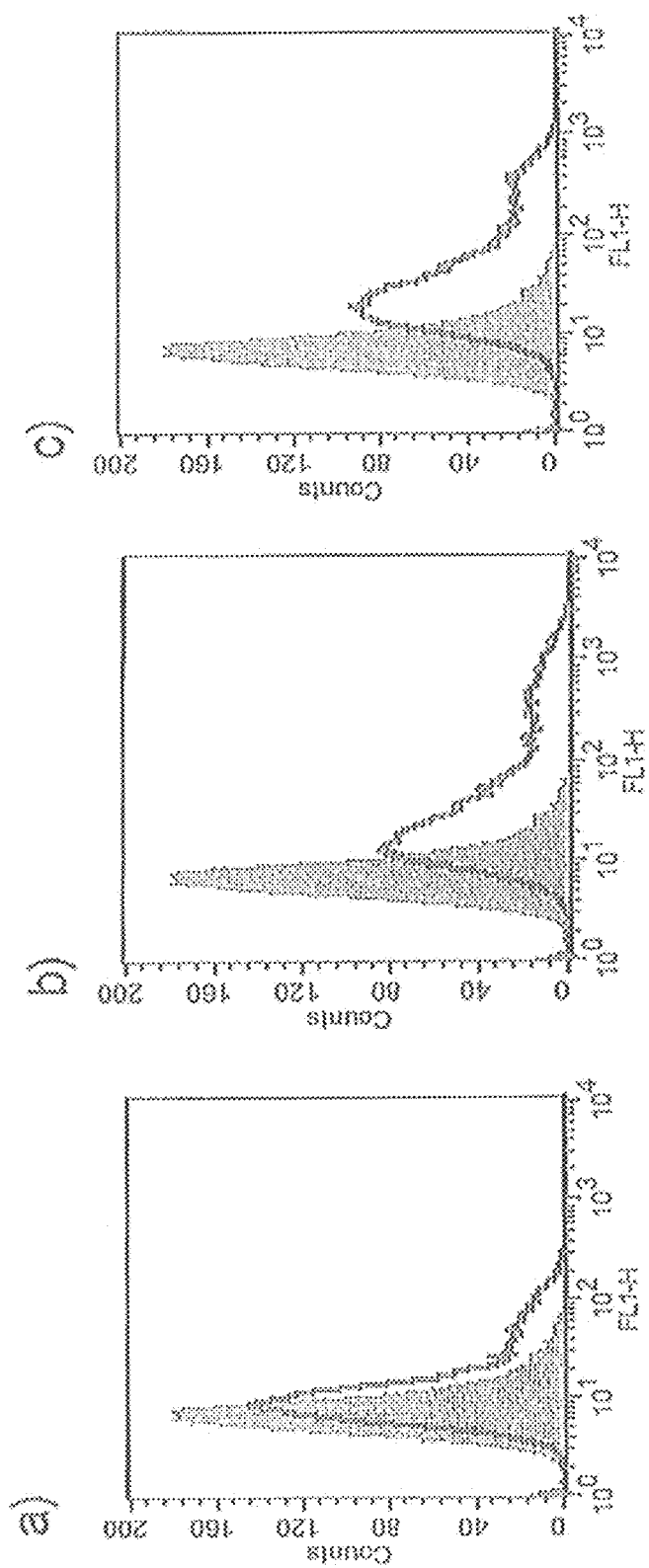
FIG. 13 shows the results of an FACS analysis of the bindabilities of clones classified under Group.11 for cells expressing hemagglutinin derived from subtype H3 influenza viruses, wherein all grey peaks are from negative control F008-038, and the solid-line peaks are from a) F026-427, b) F045-092, and c) F49, respectively.

Compared to the negative control F008-038, which is unreactive with the HA of Yamanashi strain of Hong Kong type influenza A, peak shifts in FACS occurred for F026-427 and F045-092 (FIG. 13). Therefore, F026-427 and F045-092 were considered to be antibodies against the HA of Yamanashi strain.

Measurements of Neutralizing Activities of Complete Human IgGs Against Influenza Viruses

[Samples and Reagents]

1. Purified Complete Human IgG Antibodies
F026-427 (Lot. 100614), F045-092 (Lot.100614)

2. Viruses
The following virus strains were used.
Human H3N2; A/Aichi/2/1968 strain, A/Kitakyusyu/159/1993 strain
Avian H3N8; A/Budgerigar/Aichi/1/1977 strain
Pandemic H1N1; A/Suita/1/2009 pdm strain
Swine H1N1; A/Swine/Hokkaido/2/1981 strain
Human H1N1; A/New Caledonia/20/1999 strain
Human H2N2; A/Okuda/1957 strain
Avian H2N2; A/duck/Hong Kong/273/1978 strain
Avian reassortant H5N1;
A/duck/Mongolia/54/2001(H5N2) strain HA×A/duck/Mongolia/47/2001(H7N1) strain NA×A/duck/Hokkaido/49/98 (H9N2) strain internal
Human H5N1; A/Vietnam/1194/2004 strain
Human H5N1; A/Anhui/1/2005 strain
Human H5N1; A/Indonesia/5/2005 strain 3. Cells and Media
MDCK cells were subcultured in 10% FCS-containing MEM, and for cultivation after neutralization test and virus infection, MEM containing 0.4% BSA but not containing FCS was used.

4. Reagents for PAP Staining
Mouse monoclonal antibody to influenza A NP (C43)
Rabbit anti serum to mouse IgG (whole molecule) cappel 55436
Goat anti serum to rabbit IgG (whole molecule) cappel 55602
Rabbit Peroxidase anti Peroxidase (PAP) cappel 55968
3,3'-Diaminobenzidin Tetrahydrochroride Sigma D5637
Hydrogen peroxide special grade reagent Sigma-Aldrich 13-1910-5

[Experimental Method]

Figure 14:
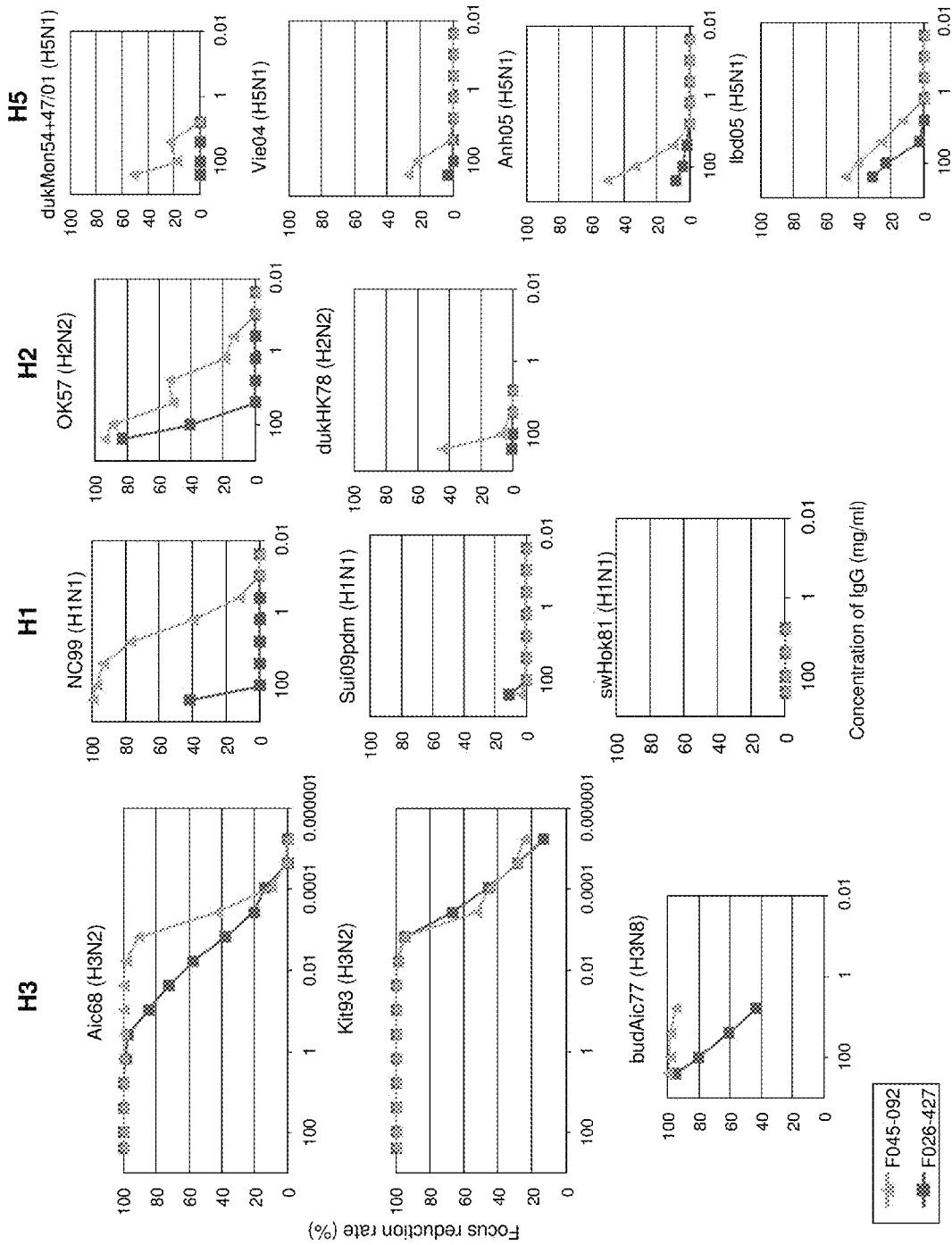
FIG. 14 shows the results of a measurement of the neutralizing activities of each IgG antibody against subtype H3, subtype H5, subtype H2 and subtype H1 influenza viruses, wherein the vertical axis indicates infection suppression rates (%), and the lateral axis indicates antibody concentrations (μg/mL).

Human IgG antibodies with the VH and VL amino acid sequences of respective clones of F026-427 and F045-092 were prepared, and used for neutralization test. Each purified human IgG antibody solution was diluted with 0.4% BSA-containing MEM to 250 μg/mL and 100 μg/mL, and additionally, serially diluted four fold using the 100 μg/mL solution as stock solution. To each of the diluted antibody solutions obtained, an equal amount of influenza virus solution of each subtype adjusted to 100 FFU was added, after which a neutralization reaction was performed at 37° C. for 1 hr. MDCK cells preliminarily subcultured in 10% FCS-containing MEM were subjected to a monolayer culture in a 96-well plate, and after washed with PBS(−), virus was adsorbed thereto at 37° C. for 1 hr using 0.4% BSA-containing MEM supplemented with the reaction solution after the neutralization reaction at 30 μL/well. The neutralization solution was removed, and after washed with PBS(−) once, 0.4% BSA-containing MEM was added at 50 μL/well, and 16 hrs of cultivation was performed at 37° C. in the presence of $CO_2$. After the culture solution was removed, cells were fixed with 100% ethanol, and dried. Subsequently, infected cells were stained by the enzyme antibody technique (PAP method), and the infection inhibitory ratio was calculated by counting the number of infected cells under the microscope. The results are shown in FIG. 14.

F026-427 showed neutralization activity against human H3N2 strain, bird H3N8 strain, human H1N1 strain and human H2N2 strain, as well as slight neutralization activity against human H5N1 strain. On the other hand, F045-092 showed neutralization activity against human H3N2 strain, bird H3N8 strain, human H1N1 strain, human and bird H2N2 strain, as well as weak neutralization activity against human and bird H5N1 strains. From the above results, it was suggested that F026-427 and F045-092 shows the reactivity with human-derived strains and bird-derived strains, with a few exceptions, but no reactivity with pig-derived strains.

Reactivity of F026-427 and F045-092 with HA0 and HA1 Expressed on 293T Cells

HA0 and HA1 genes of influenza A/H3N2 type Aichi strain were inserted into a cloning site of expression vector pDisplay to prepare pDisp-Aic68HA0 and pDisp-Aic68HA1. In the same manner, HA0 and HA1 genes of influenza A/H3N2 type Fukuoka strain were inserted into a cloning site of expression vector pDisplay to prepare pDisp-Fuk85HA0 and pDisp-Fuk85HA1. These 4 kinds of plasmids and lipofectamine LTX were each mixed, and added to 293T cells to perform transfection. Also prepared was a sample in which lipofectamine LTX alone was added to 293T without plasmid, for a negative control (Mock-transfection). After 24 hrs of cultivation, transfected cells were recovered, and blocked with 2.5% BSA-PBS-0.05% Na—$N_3$ at 4° C. for 30 min, followed by a reaction at 4° C. for 30 min with Fab-PP antibody (F026-427PP, F045-092PP), anti-influenza A/H3N2 type antibody F49, or rabbit anti-V5 tag antibody. For positive controls, Fab-PP antibody F003-137PP of anti-influenza A/H3N2 type Aichi strain was reacted at 4° C. for 30 min with cells transfected with pDisp-Aic68HA0 and pDisp-Aic68HA1, and cells of Mock-transfection. Likewise, for positive controls, Fab-PP antibody F019-102PP of influenza A/H3N2 type Fukuoka strain was reacted at 4° C. for 30 min with cells transfected with pDisp-Fuk85HA0 and pDisp-Fuk85HA1, and cells of Mock-transfection. Then, cells reacted with Fab-PP antibody were reacted with an Alexa488-labeled anti-human IgG (manufactured by Pierce), cells reacted with F49 were reacted with an Alexa488-labeled anti-mouse IgG (manufactured by Pierce), and cells reacted with rabbit anti-V5 tag antibody were reacted with an Alexa488-labeled anti-rabbit IgG (manufactured by Pierce), respectively, and FACS analysis was performed.

Compared to the control Mock-transfection cells not expressing HA, F045-092PP reacted to cells expressing HA0 and HA1 of influenza A/H3N2 type Aichi strain and HA0 and HA1 of influenza A/H3N2 type Fukuioka strain, causing a peak shift in FACS (FIG. 15-1). Compared to the control Mock-transfection cells not expressing HA, F026-427PP was slightly reactive to cells expressing HA0 and HA1 of influenza A/H3N2 type Aichi strain, causing a peak shift in FACS (FIG. 15-2). V5 tag antibody, which was an antibody for confirming the expression of HA0 and HAL was shown to be sufficiently expressed in any of HA0 and HA1 expressing cells. Also, F004-137PP and F019-102PP sufficiently reacted to HA0 and HAL respectively. F49 reacted to HA0, but did not react to HAL Because F026-427 and F045-092 reacted to HAL it was considered that epitopes recognized by these antibodies are present on HA1 molecule, and that the recognition epitopes thereof are different from those of F49, which has a wide range of strain specificity, as with F026-427 and F045-092. The recognition epitopes of antibodies derived from VH1-69 germline with a wide range of strain specificity, which has been reported in recent years, are mainly in the HA2 region, and has been considered to have neutralization activity by inhibiting the fusion activity. However, the recognition epitopes of the described F026-427 and F045-092 derived from VH1-69 germline are in the HA1 region, and as is clear from FIG. 8, it is considered that they show the neutralization activity owing to their HI activities. There is no precedent for an antibody with such the property, and hence, these are antibodies with a totally novel property. Furthermore, as is clear from FIG. 16, the recognition epitope of F026-427 and F045-092 were considered to be in the vicinity of epitope B.

Inhibition of ELISA Activity by F004-104

Figure 16:
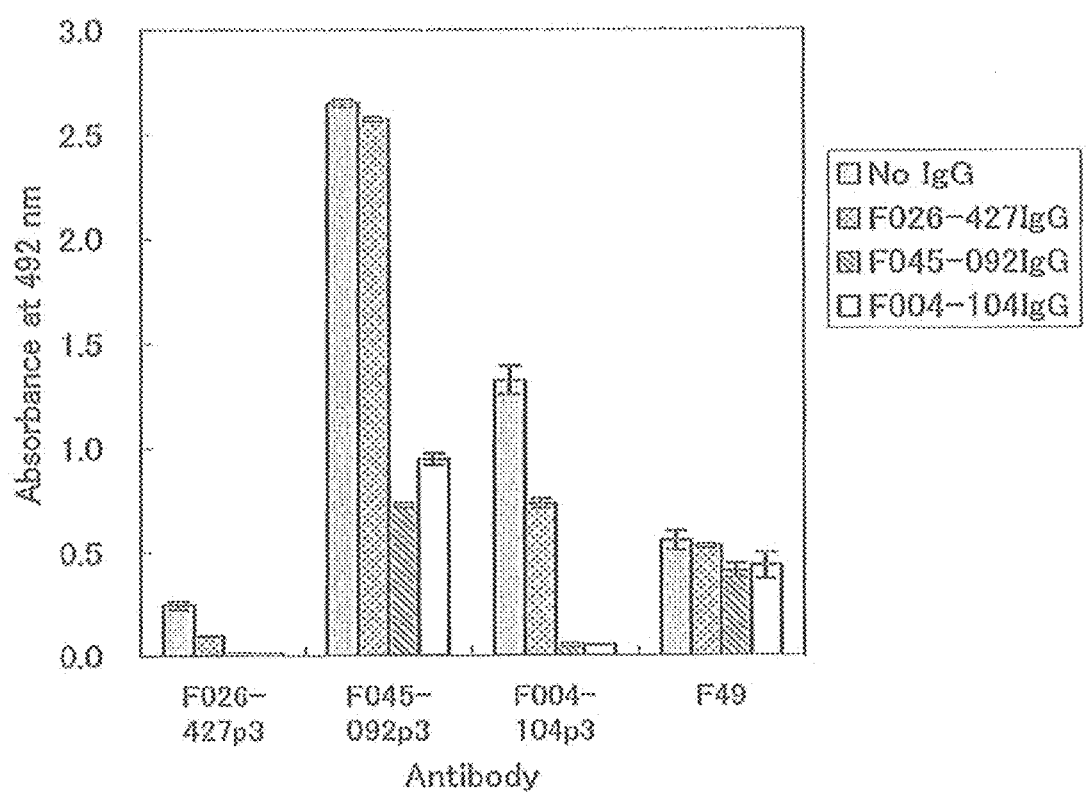
FIG. 16 shows the results of an ELISA determination of whether the antibody F004-104, which recognizes the epitope B on the HA molecule, and antibody clones classified under Group.11 share an epitope. ELISA was performed to determine the actions of the Fab-p3 type monoclonal antibodies F026-427p3, F045-092p3, F004-104p3 and the mouse-derived anti-influenza A/H3N2 antibody F49 on the influenza A/H3N2 Panama strain in the presence and absence (No IgG) of IgG antibodies (F026-427IgG, F045-092IgG, F004-104IgG).

Fab-p3 type monoclonal antibodies, F026-427p3, F045-092p3 and F004-104p3, and mouse-derived anti-influenza A/H3N2 type antibody F49 were reacted with an immunoplate to which a vaccine for influenza A/H3N2 type Panama strain had been adsorbed, in the presence and absence (No IgG) of IgG antibodies (F026-427IgG, F045-092IgG, F004-104IgG). Then, in order to detect Fab-p3 antibodies bound to the vaccine, a rabbit-derived anti-p3 antibody was reacted, followed by a reaction with an HRP-labeled anti-rabbit IgG antibody, and caused to develop color by OPD. In addition, for detecting F49, an HRP-labeled anti-rabbit IgG antibody was reacted, and caused to develop color by OPD. The results are shown in FIG. 16.

Significant inhibitions of the ELISA activities between the same kind of antibodies were entirely observed. F045-092IgG and F004-104IgG inhibited the ELISA activities of any of F026-427p3, F045-092p3 and F004-104p3. Also, F026-427IgG inhibited the ELISA activity of F004-104p3. On the other hand, F026-427IgG did not significantly inhibit F045-092p3, which was considered to be stemmed from a much stronger binding activity of F045-092 as compared to that of F026-427. For F49, no significant inhibition of ELISA activity by the IgG antibodies used was observed.

F004-104 is an antibody whose recognition epitope has been demonstrated, as a result of escape mutant analysis, to be in the vicinity of the amino acid sequence of the 159th and 190th positions on HA1 molecule (FIG. 17-1, FIG. 17-2). The recognition epitopes of F026-427 and F045-092 was considered to be near the recognition epitope of F004-104, as a result of competitive ELISA. Accordingly, the recognition epitopes of F026-427 and F045-092 were assumed to be in the vicinity of the amino acid sequence of the 159th and 190th positions on HA1 moledule.

Reactivities of F045-092 and F026-427 Against Variant of the 136th Amino Acid

The 136th serine residue of HA of Aic68 strain was replaced with threonine (variant Aic68S136T) or alanine (variant Aic68S136A) to prepare variant HAs. These variants and wild-type Aic68 strain Aic68 wt were caused to be expressed on 293T cells, and subjected to a reaction with F026-427, F045-092, F003-137, F035-015 or F033-038, after which the reactivities were examined by the flow cytometry analysis. The results are shown in FIG. 18.

As a result, F035-015 and F033-038 showed no change in the reactivity against the two variants. The reactivity of F045-092 against Aic68S136T was slightly weak than that against Aic68 wt. The reactivity of F045-092 against Aic68S136A was even weaker. Because the mutation of serine residue at 136th position affected the recognition of HA by F045-092, it was assumed that the 136th residue or an amino acid in the vicinity thereof is the HA recognition epitope of F045-092.

FCM Analyses of F045-092 for Chimeric HA 133A and 142A

The amino acid sequence of 142-146th positions of HA of Wyo03 strain was transplanted into the amino acid sequence of 142-146th positions of HA of Aic68 strain to prepare a chimera HA (Aic68_142A). Reversely, the amino acid sequence of 142-146th positions of HA of Aic68 strain was transplanted into the amino acid sequence of 142-146th positions of HA of Wyo03 strain to prepare a chimera HA (Wyo03_142A). On the other hand, the amino acid sequence of 142-146th positions of HA of Aic68 strain was transplanted into the amino acid sequence of 142-146th positions of HA of Fuk85 strain to prepare a chimera HA (Fuk85_142A). Furthermore, the amino acid sequence of 133-137th positions of HA of Wyo03 strain was transplanted into the amino acid sequence of 133-137th positions of HA of Fuk85 strain to prepare a chimera HA (Fuk85_133A). These variants and wild-type Aic68 strain HA (Aic68_Wild), wild-type Wyo03 strain HA (Wyo03_Wild), wild-type Fuk85 strain HA (Fuk85_Wild) were caused to be expressed on 293T cells, followed by reaction with F045-092, after which the reactivities were examined by the flow cytometric analysis (EMAC method [epitope mapping through analysis of chimaeras]; Okada et al, Journal of General Virology, vol. 92, 326-335, 2011). The Results are shown in FIGS. 19 and 20.

F045-092 showed a sufficiently strong reactivity to Aic68_Wild, but slightly reacted with chimera Aic68_142A, into which the amino acid sequence of 142-146th positions of Wyo03 strain had been transplanted. This demonstrated that the amino acid sequence of 142-146th positions of Wyo03 strain inhibits the recognition of HA by F045-092. The amino acid sequence of 142-146th positions of Wyo03 strain has many amino acid residues with relatively high molecular weights, suggesting the possibility of causing steric hindrance when the antibody binds to HA. On the other hand, F045-092 reacts very weakly to Fuk85_Wild, but strongly reacts to chimera Fuk85_133A, into which the amino acid sequence of 133-137th positions of Wyo03 strain HA has been transplanted. In order to effect the recognition of HA by F045-092, it was considered that the amino acid sequence of 133-137th positions is preferably of Wyo03 strain type rather than of Fuk85 strain type. Accordingly, it was assumed that the amino acid sequence of 133-137th positions are the recognition epitope of F045-092, or it is in the vicinity.

HA1 Antigen Recognition Sites of Anti-HA Antibodies Used in Competitive Studies

An X-ray crystal structural analysis file of HA of H3 (1HA0) was downloaded from the Protein Data Bank, and the three dimensional structure of 91-260th amino acid moiety in the HA1 region was constructed with Rasmol 2.7.5 software (FIG. 21). Antigen recognition sites of each H3N2 antibody for each H3N2 influenza virus were preliminarily predicted according to the EMAC method. As to F033-038, for example, the A region and the B region were estimated to be antigen recognition sites for Aic68 strain HA.

Competitive Studies Between Anti-HA Antibodies, which Bind to the Sites A, B, C, D and E of HA1 and F045-092 Antibody Competitive ELISA was performed by the EMAC method between anti-HA antibodies (F041-342, F041-360, F019-102, F004-111, F033-038, F010-073, F010-014, F004-136, F010-077, F008-055, F008-038, F008-046, F010-032, F035-015, F037-115, F004-104, F003-137), whose recognition sites on antigen had been identified, and F045-092 antibody. The results are shown in FIGS. 22-1, 22-2, 22-3, 22-4 and 22-5.

Fab-pp and Fab-cp3 types of each anti-HA antibody were prepared, and the pp type antibody, as well as the cp3 type antibody as a competitor, were added to cause a competition on the antigen, after which the binding activity of the pp type antibody against the antigen was measured. To be specific, H3N2 virus strains inactivated with folmalin were coated onto an immunoplate, which was blocked with 5% BSA. Each 50 µl of an optimal concentration of the Fab-pp antibody, and 20 µg/ml of cp3 type antibody of F045-092, or Fab-cp3 type antibody prepared by 20-fold dilution of *Escherichia coli* culture supernatant, the mixture was added to the immunoplate after completion of the blocking, and incubated at 37° C. for 1 hr. After washed with PBST, a rabbit anti-streptavidin-HRP antibody was added in order to detect pp type antibodies bound to the antigen, and further incubation was performed at 37° C. for 1 hr. After the plate was washed, OPD, which is a substrate for HRP, was added and allowed to react for 20 min, then the reaction was quenched by 2N sulfuric acid, after which the OD of the sample was measured with a wavelength of 492 nm.

H3N2 type virus strains used were as follows:
Aic68: A/Aichi/2/68
Yam77: A/Yamanashi/2/77Syd97: A/Sydney/5/97
Pan99: A/Panama/2007/99

F045-092 antibody did not compete at all with F041-342 and F041-360, which recognize site C, F019-102, which recognizes site E, or F004-111 antibody, which recognizes both of C and E sites, and was considered to not bind sites C and E. On the other hand, anti-HA antibodies (F033-038, F010-073, F010-014, F004-136, F010-077), which recognize both of sites A and B, were highly competitive against F045-092. As to an antibody (F035-015), which recognizes only site A around the receptor binding region, antibodies (F008-055, F008-038, F008-046, F010-032, F037-115, F004-104), which recognize only site B, and an antibody (F003-137), which recognizes site B2/D, although they competed against F045-092 antibody, antibodies other than F008-038 did not provide competitive results comparable with antibodies that recognize both of sites A and B. A possibility was suggested that F045-092 antibody recognizes sites A and B, and a receptor binding region that is between them and has a high preservation level of amino acids over viral types. This is consistent with that F045-092 showed HI activity.

INDUSTRIAL APPLICABILITY

According to the present invention, a human antibody that exhibits neutralizing activity on all subtypes of influenza virus can be screened for. The present invention also makes it possible to determine in advance whether the subject carries an antibody against influenza virus. It is an important task for human being to develop methods for preventing pandemics with new viral strains, for checking the spread of infection if occurring, and for developing a truly effective vaccine to gain time to inoculation to many persons. Measures being currently taken include implementation of a worldwide virus monitoring system, large stockpiling of therapeutic drugs such as Tamiflu, and development, production, and stockpiling of vaccines, but none can tell in which form a new type of virus will emerge until it emerges actually. As a new promising solution, the present invention will contribute enormously to public heath and medicine.

The invention claimed is:

1. An isolated antibody comprising a heavy chain variable region comprising the amino acid sequence set forth in SEQ ID NO:15 and a light chain variable region comprising the amino acid sequence set forth in SEQ ID NO:26, wherein the antibody binds influenza virus HA.

2. A pharmaceutical composition comprising:
   a) an isolated antibody comprising a heavy chain variable region comprising the amino acid sequence set forth in SEQ ID NO:15 and a light chain variable region comprising the amino acid sequence set forth in SEQ ID NO:26, wherein the antibody binds influenza virus HA, and
   b) a pharmacologically acceptable carrier.

* * * * *